US009447257B2

(12) United States Patent
Liu

(10) Patent No.: US 9,447,257 B2
(45) Date of Patent: Sep. 20, 2016

(54) POLYMERS COMBINED WITH CERTAIN ADDITIVES AND DEVICES MADE THEREROM

(71) Applicant: Eastman Chemical Company, Kingsport, TN (US)

(72) Inventor: Yubiao Liu, Johnson City, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 14/615,836

(22) Filed: Feb. 6, 2015

(65) Prior Publication Data

US 2015/0225542 A1   Aug. 13, 2015

Related U.S. Application Data

(60) Provisional application No. 61/938,066, filed on Feb. 10, 2014, provisional application No. 61/938,071, filed on Feb. 10, 2014.

(51) Int. Cl.
*C08L 67/02* (2006.01)
*C08K 5/435* (2006.01)
*A61L 31/06* (2006.01)
*C08G 63/199* (2006.01)

(52) U.S. Cl.
CPC .............. *C08K 5/435* (2013.01); *A61L 31/06* (2013.01); *C08G 63/199* (2013.01); *C08L 67/02* (2013.01)

(58) Field of Classification Search
CPC .............................. C08K 5/435; C08L 67/02
USPC ................................................. 524/168, 605
See application file for complete search history.

(56) References Cited

U.S. PATENT DOCUMENTS

| 3,169,121 | A |   | 2/1965  | Goldberg        |          |
|-----------|---|---|---------|-----------------|----------|
| 3,207,814 | A |   | 9/1965  | Goldberg        |          |
| 3,772,405 | A |   | 11/1973 | Hamb            |          |
| 4,156,069 | A |   | 5/1979  | Prevorsek et al.|          |
| 4,194,038 | A |   | 3/1980  | Baker et al.    |          |
| 4,430,484 | A |   | 2/1984  | Quinn           |          |
| 4,465,820 | A |   | 8/1984  | Miller et al.   |          |
| 4,981,898 | A |   | 1/1991  | Bassett         |          |
| 5,654,347 | A |   | 8/1997  | Khemani et al.  |          |
| 5,696,176 | A |   | 12/1997 | Khemani et al.  |          |
| 6,040,370 | A | * | 3/2000  | Wozny ........... | C08J 3/03 |
|           |   |   |         |                 | 524/394  |
| 6,127,485 | A |   | 10/2000 | Klun et al.     |          |
| 6,127,507 | A |   | 10/2000 | Santerre        |          |
| 2004/0072929 | A1 | * | 4/2004  | De Schryver ........... | C08K 5/03 |
|           |   |   |         |                 | 524/86   |
| 2007/0100122 | A1 |   | 5/2007  | Crawford et al. |          |
| 2007/0224377 | A1 | * | 9/2007  | Leimbacher ............ | C08L 67/02 |
|           |   |   |         |                 | 428/36.92 |
| 2008/0161468 | A1 | * | 7/2008  | Juikar .................... | C08F 14/18 |
|           |   |   |         |                 | 524/423  |
| 2008/0195170 | A1 |   | 8/2008  | Asgari          |          |
| 2008/0246191 | A1 | * | 10/2008 | Agarwal .............. | C08G 63/916 |
|           |   |   |         |                 | 264/500  |
| 2013/0018130 | A1 |   | 1/2013  | Alidedeoglu et al. |       |

OTHER PUBLICATIONS

ASTM D256; Standard Test Method for Determining the Izod Pendulum Impact Resistance of Plastics; Jun. 2010.
ASTM D3418; Standard Test Method for Transition Temperatures and Enthalpies of Fusion and Crystallization of Polymers by Differential Scanning Calorimetry; Jun. 2015.
ASTM D638; "Standard Test Method for Tensile Properties of Plastics"; Mar. 2015.
ASTM D790; "Standard Test Method for Flexural Properties of Unreinforced and Reinforced Plastics and Electrical Insulating Materials"; Apr. 2010.
ASTM D1003; "Standard Test Method for Haze and Luminous Transmittance of Transparent Plastics"; Nov. 2013.
Dunnett, Chalres W.; "A Multiple Comparison Procedure for Comparing Several Treatments with a Control."; J. Am. Statistical Assoc., vol. 50, p. 1096 (1955).
Chandy, Thomas, et al.; "Use of plasma glow for surface-engineering biomolecules to enhance bloodcompatibility of Dacron and PTFE vascular prosthesis." Biomaterials 21, (2000), pp. 699-712.
Massa, T.M., et al.; "Fibrinogen surface distribution correlates to platelet adhesion pattern on fluorinated surface-modified polyetherurethane"; Biomaterials 26, (2005), pp. 7367-7376.
Xiong, Jinsu, et al.; "Synthesis of Fluoroalkyl-Modified Polyester and Its Application in Improving the Hydrophobicity and Oleophobicity of Cured Polyester Coatings"; Journal of Applied Polymer Science; vol. 131, Issue 2, Jun. 12, 2013.

* cited by examiner

*Primary Examiner* — Kelechi Egwim
(74) *Attorney, Agent, or Firm* — Robert C. Morriss

(57) ABSTRACT

This invention relates to polymer compositions comprising: (1) at least one polymer selected from the groups consisting of:
nylon, polyesters, copolyesters, polyethylene, polypropylene, polyamides; polystyrene, polystyrene copolymers, styrene acrylonitrile copolymers, acrylonitrile butadiene styrene copolymers, poly(methylmethacrylate), acrylic copolymers, poly(ether-imides); polyphenylene oxides or poly(phenylene oxide)/polystyrene blends, polystyrene resins; polyphenylene sulfides; polyphenylene sulfide/sulfones; poly(ester-carbonates); polycarbonates; polysulfones; polysulfone ethers; and poly(ether-ketones); or mixtures of any of the other foregoing polymers, and (2) at least one fluoroalkyl derivative.

20 Claims, 1 Drawing Sheet

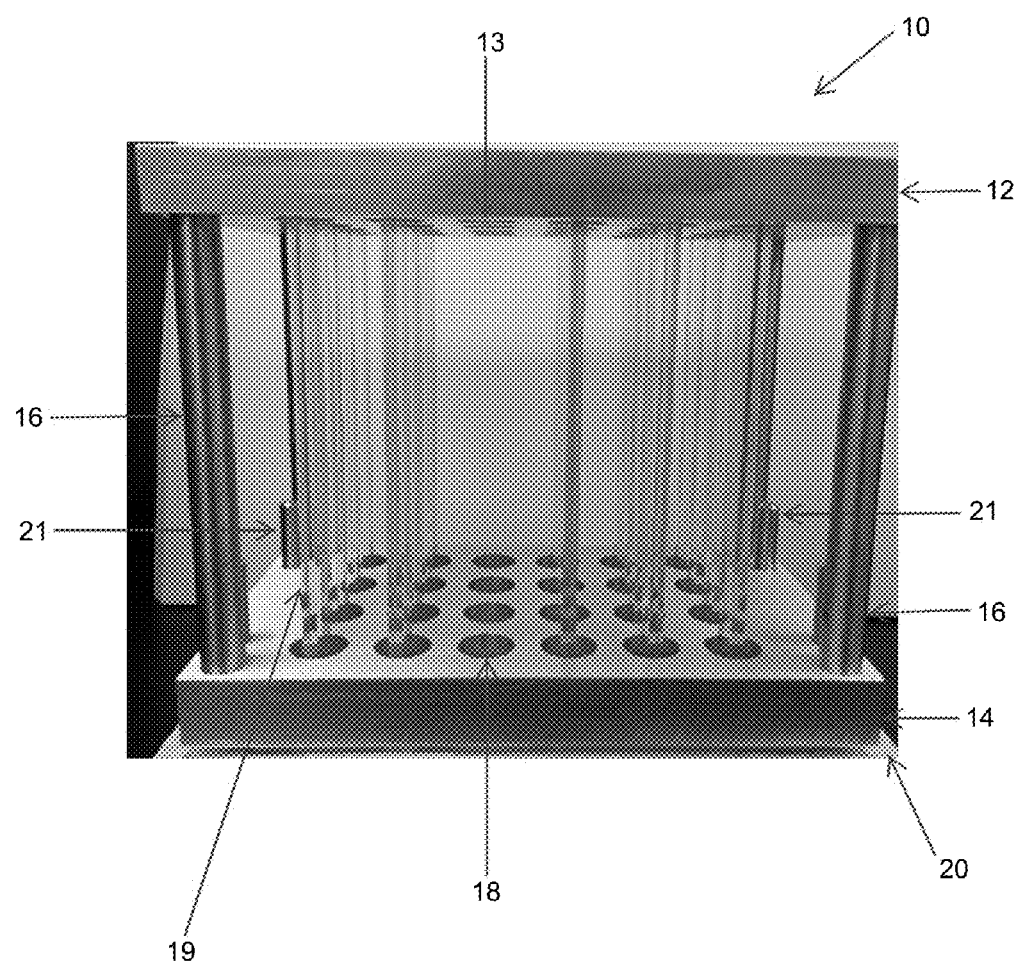

POLYMERS COMBINED WITH CERTAIN ADDITIVES AND DEVICES MADE THEREROM

CROSS-REFERENCE TO RELATED APPLICATIONS

This application claims priority to U.S. Provisional Patent Application No. 61/938,066 filed Feb. 10, 2014 and U.S. Provisional Patent Application No. 61/938,071 filed Feb. 10, 2014, the entireties of which are incorporated herein by reference to the extent not inconsistent with the present disclosure.

FIELD OF THE INVENTION

The present invention generally relates to compositions comprising polymers and fluoroalkyl derivatives, and devices and/or articles made therefrom, for example, medical devices.

BACKGROUND OF THE INVENTION

Polymers such as certain copolyesters, polycarbonates (PC) cellulosics, impact modified acrylic and styrenic, transparent acrylonitrile butadiene styrene (TABS) are widely used in the medical industry, pharmaceutical industry, bioprocessing industry, and the food industry. Each of these polymers has its own advantages and disadvantages.

A combination of any two or more of the following properties can be important in certain industries, for example, in the medical field, the health care field, the pharmaceutical field, the bioprocessing field, and the food container and food processing field: optical clarity, good toughness, good heat resistance, good lubricity (the capacity to reduce friction and/or properties of a lubricant) such as having a low coefficient of friction (COF), good anti-protein binding properties, reduced fibrinogen adsorption, good hydrolytic stability, and good chemical resistance.

Medical devices are widely used in the healthcare industry to diagnose, mitigate, or prevent disease(s) for patients. These devices include but are not limited to components for infusion and intravenous systems, extracorporeal oxygenators, renal dialyzers catheters, and heart assist devices, all of which require contact with blood. For certain of these medical devices, blood compatibility is an important characteristic. It is well known that a material's surface properties can affect the events of blood protein adsorption and platelet adhesion, particularly when the material is used in a medical device. When most foreign surfaces are exposed to blood or other bodily fluids, proteins from the blood and/or bodily fluids adsorb onto them almost immediately, depending on the material's surface properties.

It also has become increasingly important to use a material in the medical industry, food industry, and in certain other industries that the composition(s), article of manufacture and/or medical device contains substantially little to no bisphenol A, the latter being typically associated with polycarbonates. A material with anti-protein binding properties, including but not limited to reduced fibrinogen adsorption, is of particular interest where living matter (human, animal, organisms, enzymes, etc.) or previously living matter may come into contact with the material, for example, the medical industry, health care industry, pharmaceutical industry, bioprocessing industry, food industry, as well as other industries. Bioprocessing refers to treating or preparing a material through a biological process and can generally refer to production of a commercially useful biological material, chemical, food, drink and/or fuel by biological processes such as microbial fermentation or degradation.

Therefore, there is a need in the art for compositions having a combination of at least two of the described properties that are useful in the manufacture of articles of manufacture and/or devices useful in these industries.

SUMMARY OF THE INVENTION

This invention relates to polymer compositions comprising: (1) at least one polymer selected from the groups consisting of:
nylon, polyesters, copolyesters, polyethylene, polypropylene, polyamides; polystyrene, polystyrene copolymers, styrene acrylonitrile copolymers, acrylonitrile butadiene styrene copolymers, poly(methylmethacrylate), acrylic copolymers, poly(ether-imides); polyphenylene oxides or poly(phenylene oxide)/polystyrene blends, polystyrene resins; polyphenylene sulfides; polyphenylene sulfide/sulfones; poly(ester-carbonates); polycarbonates; polysulfones; polysulfone ethers; and poly(ether-ketones); or mixtures of any of the other foregoing polymers, and (2) at least one fluoroalkyl derivative.

In one embodiment, the invention relates to compositions comprising at least one polyester comprising residues of at least one glycol selected from the group consisting of ethylene glycol, 1,4-cyclohexanedimethanol, and 2,2,4,4-tetramethyl-1,3-cyclobutanediol, and at least one fluoroalkyl derivative, and articles of manufacture or devices made therefrom.

In one embodiment, the invention relates to compositions comprising at least one polyester comprising residues of terephthalic acid and/or dimethyl terephthalate and residues of at least one glycol selected from the group consisting of ethylene glycol, 1,4-cyclohexanedimethanol, and 2,2,4,4-tetramethyl-1,3-cyclobutanediol, and at least one fluoroalkyl derivative, and articles of manufacture or devices made therefrom.

In one embodiment, the invention relates to compositions comprising at least one polyester comprising an acid component which comprises residues of terephthalic acid and isophthalic acid and/or esters thereof such as dimethyl terephthalate, and at glycol component comprising residues of at least one glycol selected from the group consisting of ethylene glycol residues, 1,4-cyclohexanedimethanol residues, and 2,2,4,4-tetramethyl-1,3-cyclobutanediol, and at least one fluoroalkyl derivative, and articles of manufacture or devices made therefrom.

In one embodiment, the invention relates to compositions comprising at least one polyester comprising terephthalic acid residues, or an ester thereof, or mixtures thereof, and 1,4-cyclohexanedimethanol residues, and at least one fluoroalkyl derivative, and articles of manufacture or devices made therefrom.

In one embodiment, the invention relates to compositions comprising at least one polyester made from terephthalic acid residues, or an ester thereof, or mixtures thereof, and 1,4-cyclohexanedimethanol residues and/or 2,2,4,4-tetramethyl-1,3-cyclobutanediol residues, and at least one fluoroalkyl derivative, and articles of manufacture or devices made therefrom.

In one embodiment, the invention relates to compositions comprising at least one polyester made from terephthalic acid residues, or an ester thereof, or mixtures thereof, 2,2,4,4-tetramethyl-1,3-cyclobutanediol residues, and 1,4- cyclohexanedimethanol residues, and at least one fluoroalkyl derivative, and articles of manufacture or devices made therefrom.

In one embodiment, the invention relates to compositions comprising at least one polyester made from terephthalic acid residues, or an ester thereof, or mixtures thereof, 2,2,4,4-tetramethyl-1,3-cyclobutanediol residues, and ethylene glycol residues, and at least one fluoroalkyl derivative, and articles of manufacture or devices made therefrom.

In one embodiment, the invention relates to compositions comprising at least one polyester comprising terephthalic acid residues, or an ester thereof, or mixtures thereof, ethylene glycol residues, and 1,4-cyclohexanedimethanol residues, and at least one fluoroalkyl derivative, and articles of manufacture or devices made therefrom.

In some embodiments, the fluoroalkyl derivative(s) may be added prior to and/or during and/or after the polymerization of the polyester. In one embodiment, the fluoroalkyl derivatives useful in all of polyester compositions of the invention can be added to the base polymer through compounding or blending using techniques known in the art prior to the manufacturing of an article. In one embodiment, the fluoroalkyl derivatives(s) is blended with the polymer resulting in the final polymer composition of the invention being a blend. The fluoroalkyl derivative(s) may be added in step by step increments or simultaneously.

In any of the embodiments of the polyester compositions of the invention, articles of manufacture including but not limited to medical devices, for example, intravenous components, made from the polyester compositions are contemplated as part of this invention.

In each embodiment, at least one fluoroalkyl derivative can be used. In each embodiment, at least one fluoroalkyl derivative can be PM-870 additive commercially available from 3M, St. Paul, Minn.

In one aspect, the invention relates to a polyester composition comprising at least one fluoroalkyl derivative and at least one polyester which comprises:
(a) a dicarboxylic acid component comprising:
i) 70 to 100 mole % of terephthalic acid residues;
ii) 0 to 30 mole % of aromatic dicarboxylic acid residues having up to 20 carbon atoms; and
iii) 0 to 10 mole % of aliphatic dicarboxylic acid residues having up to 16 carbon atoms; and
(b) a glycol component comprising:
i) 1 to 99 mole % of glycol residues selected from at least one of 1,4-cyclohexanedimethanol residues, ethylene glycol residues, and 2,2,4,4-tetramethyl-1,3-cyclobutanediol residues;
wherein the total mole % of the dicarboxylic acid component is 100 mole %, the total mole % of the glycol component is 100 mole %; and
wherein the inherent viscosity of the polyester is from 0.1 to 1.2 dL/g as determined in 60/40 (wt/wt) phenol tetrachloroethane at a concentration of 0.5 g/100 ml at 25° C.; and
wherein the polyester has a Tg of from 80 to 200° C.; and at least one fluoroalkyl derivative.

In one aspect, the invention relates to a polyester composition comprising at least one fluoroalkyl derivative and at least one polyester which comprises:
(a) a dicarboxylic acid component comprising:
i) 50 to 100 mole % of terephthalic acid residues;
ii) 0 to 50 mole % of aromatic dicarboxylic acid residues having up to 20 carbon atoms; and
iii) 0 to 10 mole % of aliphatic dicarboxylic acid residues having up to 16 carbon atoms; and
(b) a glycol component comprising from 1 to 100 mole % of 1,4-cyclohexanedimethanol residues,
wherein the total mole % of the dicarboxylic acid component is 100 mole %, the total mole % of the glycol component is 100 mole %; and
wherein the inherent viscosity of the polyester is from 0.1 to 1.2 dL/g as determined in 60/40 (wt/wt) phenol tetrachloroethane at a concentration of 0.5 g/100 ml at 25° C.; and
wherein the polyester has a Tg of from 80 to 200° C.; and at least one fluoroalkyl derivative.

In one aspect, the invention relates to a polyester composition comprising at least one fluoroalkyl derivative and at least one polyester which comprises:
(a) a dicarboxylic acid component comprising:
i) 50 to 99 mole % of terephthalic acid residues;
ii) 1 to 50 mole % of isophthalic acid residues;
ii) 0 to 49 mole % of aromatic dicarboxylic acid residues having up to 20 carbon atoms; and
iii) 0 to 10 mole % of aliphatic dicarboxylic acid residues having up to 16 carbon atoms; and
(b) a glycol component comprising from 1 to 100 mole % of 1,4-cyclohexanedimethanol residues,
wherein the total mole % of the dicarboxylic acid component is 100 mole %, the total mole % of the glycol component is 100 mole %; and
wherein the inherent viscosity of the polyester is from 0.1 to 1.2 dL/g as determined in 60/40 (wt/wt) phenol tetrachloroethane at a concentration of 0.5 g/100 ml at 25° C.; and
wherein the polyester has a Tg of from 80 to 200° C.; and at least one fluoroalkyl derivative.

In one aspect, the invention relates to a polyester composition comprising at least one fluoroalkyl derivative and at least one polyester which comprises:
(a) a dicarboxylic acid component comprising:
i) 55 to 75 mole % of terephthalic acid residues;
ii) 25 to 45 mole % of isophthalic acid residues;
ii) 0 to 49 mole % of aromatic dicarboxylic acid residues having up to 20 carbon atoms; and
iii) 0 to 10 mole % of aliphatic dicarboxylic acid residues having up to 16 carbon atoms; and
(b) a glycol component comprising from 80 to 100 mole % of 1,4-cyclohexanedimethanol residues,
wherein the total mole % of the dicarboxylic acid component is 100 mole %, the total mole % of the glycol component is 100 mole %; and
wherein the inherent viscosity of the polyester is from 0.1 to 1.2 dL/g as determined in 60/40 (wt/wt) phenol tetrachloroethane at a concentration of 0.5 g/100 ml at 25° C.; and
wherein the polyester has a Tg of from 80 to 200° C.; and at least one fluoroalkyl derivative.

In one aspect, the invention relates to a polyester composition comprising at least one fluoroalkyl derivative and at least one polyester which comprises:
(a) a dicarboxylic acid component comprising:
i) 70 to 100 mole % of terephthalic acid residues;
ii) 0 to 30 mole % of aromatic dicarboxylic acid residues having up to 20 carbon atoms; and
iii) 0 to 10 mole % of aliphatic dicarboxylic acid residues having up to 16 carbon atoms; and
(b) a glycol component comprising from 1 to 99 mole % of 1,4-cyclohexanedimethanol residues,
wherein the total mole % of the dicarboxylic acid component is 100 mole %, the total mole % of the glycol component is 100 mole %; and
wherein the inherent viscosity of the polyester is from 0.1 to 1.2 dL/g as determined in 60/40 (wt/wt) phenol tetrachloroethane at a concentration of 0.5 g/100 ml at 25° C.; and wherein the polyester has a Tg of from 80 to 200° C.; and at least one fluoroalkyl derivative.

In one aspect, the invention relates to a polyester composition comprising at least one fluoroalkyl derivative and at least one polyester which comprises:
(a) a dicarboxylic acid component comprising:
i) 70 to 100 mole % of terephthalic acid residues;
ii) 0 to 30 mole % of aromatic dicarboxylic acid residues having up to 20 carbon atoms; and
iii) 0 to 10 mole % of aliphatic dicarboxylic acid residues having up to 16 carbon atoms; and
(b) a glycol component comprising:
i) 1 to 99 mole % of 2,2,4,4-tetramethyl-1,3-cyclobutanediol residues; and
ii) 1 to 99 mole % of 1,4-cyclohexanedimethanol residues, wherein the total mole % of the dicarboxylic acid component is 100 mole %, the total mole % of the glycol component is 100 mole %; and wherein the inherent viscosity of the polyester is from 0.1 to 1.2 dL/g as determined in 60/40 (wt/wt) phenol tetrachloroethane at a concentration of 0.5 g/100 ml at 25° C.; and wherein the polyester has a Tg of from 80 to 200° C.; and at least one fluoroalkyl derivative.

In one aspect, the relates to a polyester composition comprising at least one fluoroalkyl derivative and at least one polyester which comprises:
(a) a dicarboxylic acid component comprising:
i) 70 to 100 mole % of terephthalic acid residues;
ii) 0 to 30 mole % of aromatic dicarboxylic acid residues having up to 20 carbon atoms; and
iii) 0 to 10 mole % of aliphatic dicarboxylic acid residues having up to 16 carbon atoms; and
(b) a glycol component comprising:
i) 10 to 99 mole % of 2,2,4,4-tetramethyl-1,3-cyclobutanediol residues; and
ii) 1 to 90 mole % of 1,4-cyclohexanedimethanol residues, wherein the total mole % of the dicarboxylic acid component is 100 mole %, the total mole % of the glycol component is 100 mole %; and wherein the inherent viscosity of the polyester is from 0.1 to 1.2 dL/g as determined in 60/40 (wt/wt) phenol tetrachloroethane at a concentration of 0.5 g/100 ml at 25° C.; and wherein the polyester has a Tg of from 80 to 200° C. comprising at least one fluoroalkyl derivative and at least one polyester composition.

In one aspect, the invention relates to a polyester composition comprising at least one polyester and at least one fluoroalkyl derivative, which polyester comprises:
(a) a dicarboxylic acid component comprising:
i) 70 to 100 mole % of terephthalic acid residues;
ii) 0 to 30 mole % of aromatic dicarboxylic acid residues having up to 20 carbon atoms; and
iii) 0 to 10 mole % of aliphatic dicarboxylic acid residues having up to 16 carbon atoms; and
(b) a glycol component comprising:
i) 10 to 30 mole % of 2,2,4,4-tetramethyl-1,3-cyclobutanediol residues; and
ii) 70 to 90 mole % of 1,4-cyclohexanedimethanol residues, wherein the total mole % of the dicarboxylic acid component is 100 mole %, the total mole % of the glycol component is 100 mole %; and wherein the inherent viscosity of the polyester is from 0.35 to 1.2 dL/g as determined in 60/40 (wt/wt) phenol tetrachloroethane at a concentration of 0.5 g/100 ml at 25° C.; and wherein the polyester has a Tg of from 90 to 130° C.

In one aspect, the invention relates to a polyester composition comprising at least one fluoroalkyl derivative and at least one polyester, which polyester comprises:
(a) a dicarboxylic acid component comprising:
i) 70 to 100 mole % of terephthalic acid residues;
ii) 0 to 30 mole % of aromatic dicarboxylic acid residues having up to 20 carbon atoms; and
iii) 0 to 10 mole % of aliphatic dicarboxylic acid residues having up to 16 carbon atoms; and
(b) a glycol component comprising:
i) 15 to 30 mole % of 2,2,4,4-tetramethyl-1,3-cyclobutanediol residues; and
ii) 70 to 85 mole % of 1,4-cyclohexanedimethanol residues, wherein the total mole % of the dicarboxylic acid component is 100 mole %, the total mole % of the glycol component is 100 mole %; and wherein the inherent viscosity of the polyester is from 0.35 to 0.75 dL/g as determined in 60/40 (wt/wt) phenol tetrachloroethane at a concentration of 0.5 g/100 ml at 25° C.; and wherein the polyester has a Tg of from 80 to 130° C.

In one aspect, the invention relates to a polyester composition comprising at least one fluoroalkyl derivative and at least one polyester which comprises:
(a) a dicarboxylic acid component comprising:
i) 70 to 100 mole % of terephthalic acid residues;
ii) 0 to 30 mole % of aromatic dicarboxylic acid residues having up to 20 carbon atoms; and
iii) 0 to 10 mole % of aliphatic dicarboxylic acid residues having up to 16 carbon atoms; and
(b) a glycol component comprising:
i) 15 to 40 mole % of 2,2,4,4-tetramethyl-1,3-cyclobutanediol residues; and
ii) 60 to 85 mole % of 1,4-cyclohexanedimethanol residues, wherein the total mole % of the dicarboxylic acid component is 100 mole %, the total mole % of the glycol component is 100 mole %; and wherein the inherent viscosity of the polyester is from 0.35 to 1.0 dL/g as determined in 60/40 (wt/wt) phenol tetrachloroethane at a concentration of 0.5 g/100 ml at 25° C.

In one aspect, the invention relates to a polyester composition comprising at least one fluoroalkyl derivative and at least one polyester which comprises:
(a) a dicarboxylic acid component comprising:
i) 70 to 100 mole % of terephthalic acid residues;
ii) 0 to 30 mole % of aromatic dicarboxylic acid residues having up to 20 carbon atoms; and
iii) 0 to 10 mole % of aliphatic dicarboxylic acid residues having up to 16 carbon atoms; and
(b) a glycol component comprising:
i) 30 to 40 mole % of 2,2,4,4-tetramethyl-1,3-cyclobutanediol residues; and
ii) 60 to 70 mole % of 1,4-cyclohexanedimethanol residues, wherein the total mole % of the dicarboxylic acid component is 100 mole %, the total mole % of the glycol component is 100 mole %; and wherein the inherent viscosity of the polyester is from 0.1 to 1.2 dL/g as determined in 60/40 (wt/wt) phenol tetrachloroethane at a concentration of 0.5 g/100 ml at 25° C.

In one aspect, the invention relates to a polyester composition comprising at least one fluoroalkyl derivative and at least one polyester which comprises:
 (a) a dicarboxylic acid component comprising:
 i) 70 to 100 mole % of terephthalic acid residues;
 ii) 0 to 30 mole % of aromatic dicarboxylic acid residues having up to 20 carbon atoms; and
 iii) 0 to 10 mole % of aliphatic dicarboxylic acid residues having up to 16 carbon atoms; and
 (b) a glycol component comprising:
 i) 1 to 100 mole % of ethylene glycol residues; and
wherein the total mole % of the dicarboxylic acid component is 100 mole %, the total mole % of the glycol component is 100 mole %; and
wherein the inherent viscosity of the polyester is from 0.1 to 1.2 dL/g as determined in 60/40 (wt/wt) phenol tetrachloroethane at a concentration of 0.5 g/100 ml at 25° C.

The invention relates to a polyester composition comprising at least one fluoroalkyl derivative and at least one polyester which comprises:
 (a) a dicarboxylic acid component comprising:
 i) 70 to 100 mole % of terephthalic acid residues;
 ii) 0 to 30 mole % of aromatic dicarboxylic acid residues having up to 20 carbon atoms; and
 iii) 0 to 10 mole % of aliphatic dicarboxylic acid residues having up to 16 carbon atoms; and
 (b) a glycol component comprising:
 comprising:
 i) 1 to 99 mole % of ethylene glycol residues; and
 ii) 1 to 99 mole % of 2,2,4,4-tetramethyl-1,3-cyclobutanediol residues, and
wherein the total mole % of the dicarboxylic acid component is 100 mole %, the total mole % of the glycol component is 100 mole %; and
wherein the inherent viscosity of the polyester is from 0.1 to 1.2 dL/g as determined in 60/40 (wt/wt) phenol tetrachloroethane at a concentration of 0.5 g/100 ml at 25° C.

In one aspect, the invention relates to a polyester composition comprising at least one fluoroalkyl derivative and at least one polyester which comprises:
 (a) a dicarboxylic acid component comprising:
 i) 70 to 100 mole % of terephthalic acid residues;
 ii) 0 to 30 mole % of aromatic dicarboxylic acid residues having up to 20 carbon atoms; and
 iii) 0 to 10 mole % of aliphatic dicarboxylic acid residues having up to 16 carbon atoms; and
 (b) a glycol component comprising:
 i) 1 to 99 mole % of ethylene glycol residues; and
 ii) 1 to 99 mole % of 1,4-cyclohexanedimethanol residues,
wherein the total mole % of the dicarboxylic acid component is 100 mole %, the total mole % of the glycol component is 100 mole %; and
wherein the inherent viscosity of the polyester is from 0.1 to 1.2 dL/g as determined in 60/40 (wt/wt) phenol tetrachloroethane at a concentration of 0.5 g/100 ml at 25° C.

In one aspect, the invention relates to a polyester composition comprising at least one fluoroalkyl derivative and at least one polyester which comprises:
 (a) a dicarboxylic acid component comprising:
 i) 70 to 100 mole % of terephthalic acid residues;
 ii) 0 to 30 mole % of aromatic dicarboxylic acid residues having up to 20 carbon atoms; and
 iii) 0 to 10 mole % of aliphatic dicarboxylic acid residues having up to 16 carbon atoms; and
 (b) a glycol component comprising:
 i) 10 to 99 mole % of ethylene glycol residues; and
 ii) 1 to 90 mole % of 1,4-cyclohexanedimethanol residues,
wherein the total mole % of the dicarboxylic acid component is 100 mole %, the total mole % of the glycol component is 100 mole %; and
wherein the inherent viscosity of the polyester is from 0.1 to 1.2 dL/g as determined in 60/40 (wt/wt) phenol tetrachloroethane at a concentration of 0.5 g/100 ml at 25° C.

The invention relates to a polyester composition comprising at least one fluoroalkyl derivative and at least one polyester which comprises:
 (a) a dicarboxylic acid component comprising:
 i) 70 to 100 mole % of terephthalic acid residues;
 ii) 0 to 30 mole % of aromatic dicarboxylic acid residues having up to 20 carbon atoms; and
 iii) 0 to 10 mole % of aliphatic dicarboxylic acid residues having up to 16 carbon atoms; and
 (b) a glycol component comprising:
 i) 25 to 45 mole % of 1,4-cyclohexanedimethanol residues; and
 ii) 55 to 75 mole % of ethylene glycol residues,
wherein the total mole % of the dicarboxylic acid component is 100 mole %, the total mole % of the glycol component is 100 mole %; and
wherein the inherent viscosity of the polyester is from 0.1 to 1.2 dL/g as determined in 60/40 (wt/wt) phenol tetrachloroethane at a concentration of 0.5 g/100 ml at 25° C.

In one aspect, the invention relates to a polyester composition comprising at least one fluoroalkyl derivative and at least one polyester which comprises:
 (a) a dicarboxylic acid component comprising:
 i) 70 to 100 mole % of terephthalic acid residues;
 ii) 0 to 30 mole % of aromatic dicarboxylic acid residues having up to 20 carbon atoms; and
 iii) 0 to 10 mole % of aliphatic dicarboxylic acid residues having up to 16 carbon atoms; and
 (b) a glycol component comprising:
 i) 50 to 75 mole % of 1,4-cyclohexanedimethanol residues; and
 ii) 25 to 50 mole % of ethylene glycol residues,
wherein the total mole % of the dicarboxylic acid component is 100 mole %, the total mole % of the glycol component is 100 mole %; and
wherein the inherent viscosity of the polyester is from 0.1 to 1.2 dL/g as determined in 60/40 (wt/wt) phenol tetrachloroethane at a concentration of 0.5 g/100 ml at 25° C. In this embodiment, the polyester composition can adsorb from 5% to 20% less fibrinogen compared to the polyester alone (i.e., without the fluoroalkyl additive) according to the fibrinogen ELISA protocol described herein.

In one aspect, the polyesters useful in the invention contain less than 15 mole % ethylene glycol residues, such as, for example, 0.01 to less than 15 mole % ethylene glycol residues.

In one aspect, the polyesters useful in the invention can contain no ethylene glycol residues.

In one aspect, the polyesters useful in the invention contain no branching agent, or alternatively, at least one branching agent is added either prior to or during polymerization of the polyester.

In one aspect, the polyesters useful in the invention contain at least one branching agent without regard to the method or sequence in which it is added.

In one aspect of the invention, the mole % of cis-2,2,4,4-tetramethyl-1,3-cyclobutanediol residues useful in certain polyesters useful in the invention is greater than 50 mole % or greater than 55 mole % of cis-2,2,4,4-tetramethyl-1,3-cyclobutanediol residues or greater than 70 mole % of cis-2,2,4,4-tetramethyl-1,3-cyclobutanediol residues; wherein the total mole percentage of cis-2,2,4,4-tetramethyl-1,3-cyclobutanediol residues and trans-2,2,4,4-tetramethyl-1,3-cyclobutanediol residues is equal to a total of 100 mole %.

In one aspect of the invention, the mole % of the isomers of 2,2,4,4-tetramethyl-1,3-cyclobutanediol residues useful in certain polyesters useful in the invention is from 30 to 70 mole % of cis-2,2,4,4-tetramethyl-1,3-cyclobutanediol residues or from 30 to 70 mole % of trans-2,2,4,4-tetramethyl-1,3-cyclobutanediol residues, or from 40 to 60 mole % of cis-2,2,4,4-tetramethyl-1,3-cyclobutanediol residues or from 40 to 60 mole % of trans-2,2,4,4-tetramethyl-1,3-cyclobutanediol residues, wherein the total mole percentage of cis-2,2,4,4-tetramethyl-1,3-cyclobutanediol residues and trans-2,2,4,4-tetramethyl-1,3-cyclobutanediol residues is equal to a total of 100 mole %.

In one embodiment, the article of manufacture of the invention can be any device known in the art in which one or more of the physical characteristics are useful including but not limited to medical devices, containers, bottles, trays, film or sheet, etc.

Specific potential articles of manufacture and/or packaging can include, for example, medical packaging and/or articles, pharmaceutical packaging and/or articles, other health care packaging and/or articles, packaging and/or articles for bioprocessing, food packaging and/or articles, or devices made therefrom, for example, medical devices such as thermoformed trays, sterile or non-sterile packaging, steam sterilization bags or pouches, blood bags, tubing, catheters, glucose sensor strips.

The medical devices can include but are not limited to components for infusion and intravenous systems, extracorporeal oxygenators, renal dialyzers catheters, and heart assist devices In one embodiment, the medical device can be an intravenous device or component. In one embodiment, the intravenous device or component can be a stopcock. In one embodiment, a stopcock can be an externally operated valve regulating the flow of a liquid or gas through a pipe or tube. In one embodiment, a stopcock can regulate the flow of intravenous fluids into a human being.

In one embodiment, two-port, three-port and four-port stopcocks are contemplated.

In one embodiment, the compositions of the invention and/or the articles or devices made therefrom, have a combination of any two or more of the following properties: good optical clarity, good toughness, good heat resistance, good lubricity (the capacity to reduce friction and/or properties of a lubricant) such as having a low coefficient of friction (COF), good anti-protein binding properties, reduced fibrinogen adsorption, hydrolytic stability, and good chemical resistance.

In one embodiment, the compositions of the invention and/or the articles or devices made therefrom, have a combination of any two or more of the following properties: good optical clarity, good anti-protein binding properties such as reduced fibrinogen adsorption, and good lubricity (the capacity to reduce friction and/or properties of a lubricant) such as having a low coefficient of friction (COF).

In one embodiment, the compositions of the invention and/or the articles or devices made therefrom, have a combination of any two or more of the following properties: good optical clarity, improved chemical resistance, and good lubricity, for example, a low coefficient of friction.

In one embodiment, the compositions of the invention and/or the articles or devices made therefrom, have a combination of good anti-protein binding properties such as reduced fibrinogen adsorption and good lubricity, for example, a low coefficient of friction.

In one embodiment, the compositions of the invention and/or the articles or devices made therefrom, have a combination of good optical clarity and good anti-protein binding properties such as reduced fibrinogen adsorption.

In one embodiment, the compositions of the invention and/or the articles or devices made therefrom are optically clear and have good chemical resistance.

In another embodiment, the fluoroalkyl derivative(s) serves to lower the coefficient of friction for the polyester, in some cases, substantially lower.

In another embodiment, the compositions of the invention and/or the articles or devices made therefrom can have anti-protein binding properties. Anti-protein binding properties are defined herein as stopping, preventing, or reducing the frequency and/or extent of protein binding.

In one embodiment, the compositions of the invention and/or the articles or devices made therefrom can have good lubricity.

In one embodiment, the compositions of the invention and/or the articles or devices made therefrom can have a low coefficient of friction and good anti-protein binding properties such as reduced fibrinogen adsorption.

In one embodiment, the compositions of the invention and/or the articles or devices made therefrom can have at least two of the following properties: optical clarity, chemically resistant, good anti-protein binding properties such as reduced fibrinogen adsorption, and a low coefficient of friction.

In one embodiment, the polyester compositions according to the invention can adsorb at least 5% less fibrinogen compared to the polyester alone (i.e., without the fluoroalkyl additive) according to the fibrinogen ELISA protocol described herein.

In one embodiment, the polyester compositions according to the invention can adsorb from 5% to 50% less fibrinogen compared to the polyester alone (i.e., without the fluoroalkyl additive) according to the fibrinogen ELISA protocol described herein.

In one embodiment, the polyester compositions according to the invention can adsorb from 5% to 45% less fibrinogen compared to the polyester alone (i.e., without the fluoroalkyl additive) according to the fibrinogen ELISA protocol described herein.

In one embodiment, the polyester compositions according to the invention can adsorb from 5% to 40% less fibrinogen compared to the polyester alone (i.e., without the fluoroalkyl additive) according to the fibrinogen ELISA protocol described herein.

In one embodiment, the polyester compositions according to the invention can adsorb from 10% to 40% less fibrinogen compared to the polyester alone (i.e., without the fluoroalkyl additive) according to the fibrinogen ELISA protocol described herein.

In one embodiment, the polyester compositions according to the invention can adsorb from 15% to 45% less fibrinogen compared to the polyester alone (i.e., without the fluoroalkyl additive) according to the fibrinogen ELISA protocol described herein.

In one embodiment, certain polyester compositions according to the invention can adsorb from 5% to 20% less fibrinogen compared to the polyester alone (i.e., without the fluoroalkyl additive) according to the fibrinogen ELISA protocol described herein.

The definition of coefficient of friction (COF) is well known in the art and is as follows:

$$\mu = \frac{f_x}{F_z}.$$

In certain embodiments, the compositions according to the invention have a coefficient of friction (COF) of less than 0.50 as measured with a Bruker™ tribometer using a 1"×1"×0.125" plaque on a 4"×4"×0.125" plaque under a 3 N normal load at 1.2 mm/second.

In certain embodiments, the compositions according to the invention have a coefficient of friction (COF) of 0.10 to 0.50 as measured with a Bruker™ tribometer using a 1"×1"×0.125" plaque on a 4"×4"×0.125" plaque under a 3 N normal load at 1.2 mm/second.

In certain embodiments, the compositions according to the invention have a coefficient of friction (COF) of 0.15 to 0.50 as measured with a Bruker™ tribometer using a 1"×1"×0.125" plaque on a 4"×4"×0.125" plaque under a 3 N normal load at 1.2 mm/second.

In certain embodiments, the compositions according to the invention have a coefficient of friction (COF) of 0.15 to 0.40 as measured with a Bruker™ tribometer using a 1"×1"×0.125" plaque on a 4"×4"×0.125" plaque under a 3 N normal load at 1.2 mm/second.

In certain embodiments, the compositions according to the invention have a coefficient of friction (COF) of 0.15 to 0.35 as measured with a Bruker™ tribometer using a 1"×1"×0.125" plaque on a 4"×4"×0.125" plaque under a 3 N normal load at 1.2 mm/second.

In one embodiment, the polyester compositions according to the invention can adsorb at least 5% less fibrinogen compared to the polyester alone (i.e., without the fluoroalkyl additive) according to the fibrinogen ELISA protocol described herein and a coefficient of friction (COF) of less than 0.50 as measured with a Bruker™ tribometer using a 1"×1"×0.125" plaque on a 4"×4"×0.125" plaque under a 3 N normal load at 1.2 mm/second.

BRIEF DESCRIPTION OF THE DRAWING

The FIGURE is a photograph of the test fixture used in the examples for fibrinogen ELISA (enzyme-linked immunosorbent assay).

DETAILED DESCRIPTION OF THE INVENTION

The invention generally relates to polymer compositions comprising at least one polymer selected from the groups consisting of:

nylon, polyesters, copolyesters, polyethylene, polypropylene, polyamides such as ZYTEL® from DuPont; polystyrene, polystyrene copolymers, styrene acrylonitrile copolymers, acrylonitrile butadiene styrene copolymers, poly (methylmethacrylate), acrylic copolymers, poly(etherimides) such as ULTEM® (a poly(ether-imide) from General Electric); polyphenylene oxides such as poly(2,6-dimethylphenylene oxide) or poly(phenylene oxide)/polystyrene blends such as NORYL 1000® (a blend of poly(2,6-dimethylphenylene oxide) and polystyrene resins from General Electric); polyphenylene sulfides; polyphenylene sulfidesulfones; poly(ester-carbonates); polycarbonates, for example, LEXAN® (a polycarbonate from General Electric); polysulfones; polysulfone ethers; and poly(ether-ketones) of aromatic dihydroxy compounds; or mixtures of any of the other foregoing polymers, and at least one fluoroalkyl derivative.

In one embodiment, the invention relates to compositions comprising at least one polyester comprising residues of at least one glycol selected from the group consisting of ethylene glycol, 1,4-cyclohexanedimethanol, and 2,2,4,4-tetramethyl-1,3-cyclobutanediol, and at least one fluoroalkyl derivative, and articles of manufacture or devices made therefrom.

In one embodiment, the invention relates to compositions comprising at least one polyester comprising residues of terephthalic acid and/or dimethyl terephthalate and residues of at least one glycol selected from the group consisting of ethylene glycol, 1,4-cyclohexanedimethanol, and 2,2,4,4-tetramethyl-1,3-cyclobutanediol, and at least one fluoroalkyl derivative, and articles of manufacture or devices made therefrom.

In one embodiment, the invention relates to compositions comprising at least one polyester comprising an acid component which comprises residues of terephthalic acid and isophthalic acid and/or esters thereof such as dimethyl terephthalate, and at glycol component comprising residues of at least one glycol selected from the group consisting of ethylene glycol residues, 1,4-cyclohexanedimethanol residues, and 2,2,4,4-tetramethyl-1,3-cyclobutanediol, and at least one fluoroalkyl derivative, and articles of manufacture or devices made therefrom.

In one embodiment, the invention relates to compositions comprising at least one polyester comprising terephthalic acid residues, or an ester thereof, or mixtures thereof, and 1,4-cyclohexanedimethanol residues, and at least one fluoroalkyl derivative, and articles of manufacture or devices made therefrom.

In one embodiment, the invention relates to compositions comprising at least one polyester made from terephthalic acid residues, or an ester thereof, or mixtures thereof, and 1,4-cyclohexanedimethanol residues and/or 2,2,4,4-tetramethyl-1,3-cyclobutanediol residues, and at least one fluoroalkyl derivative, and articles of manufacture or devices made therefrom.

In one embodiment, the invention relates to compositions comprising at least one polyester made from terephthalic acid residues, or an ester thereof, or mixtures thereof, 2,2,4,4-tetramethyl-1,3-cyclobutanediol residues, and 1,4-cyclohexanedimethanol residues, and at least one fluoroalkyl derivative, and articles of manufacture or devices made therefrom.

In one embodiment, the invention relates to compositions comprising at least one polyester made from terephthalic acid residues, or an ester thereof, or mixtures thereof, 2,2,4,4-tetramethyl-1,3-cyclobutanediol residues, and ethylene glycol residues, and at least one fluoroalkyl derivative, and articles of manufacture or devices made therefrom.

In one embodiment, the invention relates to compositions comprising at least one polyester comprising terephthalic acid residues, or an ester thereof, or mixtures thereof, ethylene glycol residues, and 1,4-cyclohexanedimethanol residues, and at least one fluoroalkyl derivative, and articles of manufacture or devices made therefrom.

In one embodiment, the invention relates to compositions comprising at least one polyester made from terephthalic acid residues, or an ester thereof, or mixtures thereof, and 1,4-cyclohexanedimethanol residues and/or 2,2,4,4-tetramethyl-1,3-cyclobutanediol residues and at least one fluoroalkyl derivative, and articles of manufacture or devices made therefrom.

The term "polyester", as used herein, is intended to include "copolyesters" and is understood to mean a synthetic polymer prepared by the reaction of one or more difunctional carboxylic acids and/or multifunctional carboxylic acids with one or more difunctional hydroxyl compounds and/or multifunctional hydroxyl compounds. Typically the difunctional carboxylic acid can be a dicarboxylic acid and the difunctional hydroxyl compound can be a dihydric alcohol such as, for example, glycols. Furthermore, as used in this application, the term "diacid" or "dicarboxylic acid" includes multifunctional acids, such as branching agents. The term "glycol" as used in this application includes, but is not limited to, diols, glycols, and/or multifunctional hydroxyl compounds. Alternatively, the difunctional carboxylic acid may be a hydroxy carboxylic acid such as, for example, p-hydroxybenzoic acid, and the difunctional hydroxyl compound may be an aromatic nucleus bearing 2 hydroxyl substituents such as, for example, hydroquinone. The term "residue", as used herein, means any organic structure incorporated into a polymer through a polycondensation and/or an esterification reaction from the corresponding monomer. The term "repeating unit", as used herein, means an organic structure having a dicarboxylic acid residue and a diol residue bonded through a carbonyloxy group. Thus, for example, the dicarboxylic acid residues may be derived from a dicarboxylic acid monomer or its associated acid halides, esters, salts, anhydrides, or mixtures thereof. As used herein, therefore, the term dicarboxylic acid is intended to include dicarboxylic acids and any derivative of a dicarboxylic acid, including its associated acid halides, esters, half-esters, salts, half-salts, anhydrides, mixed anhydrides, or mixtures thereof, useful in a reaction process with a diol to make polyester. As used herein, the term "terephthalic acid" is intended to include terephthalic acid itself and residues thereof as well as any derivative of terephthalic acid, including its associated acid halides, esters, half-esters, salts, half-salts, anhydrides, mixed anhydrides, or mixtures thereof or residues thereof useful in a reaction process with a diol to make polyester.

In one embodiment, terephthalic acid may be used as the starting material. In another embodiment, dimethyl terephthalate may be used as the starting material. In another embodiment, mixtures of terephthalic acid and dimethyl terephthalate may be used as the starting material and/or as an intermediate material.

The polyesters used in the present invention typically can be prepared from dicarboxylic acids and diols which react in substantially equal proportions and are incorporated into the polyester polymer as their corresponding residues. The polyesters of the present invention, therefore, can contain substantially equal molar proportions of acid residues (100 mole %) and diol (and/or multifunctional hydroxyl compounds) residues (100 mole %) such that the total moles of repeating units is equal to 100 mole %. The mole percentages provided in the present disclosure, therefore, may be based on the total moles of acid residues, the total moles of diol residues, or the total moles of repeating units. For example, a polyester containing 30 mole % isophthalic acid, based on the total acid residues, means the polyester contains 30 mole % isophthalic acid residues out of a total of 100 mole % acid residues. Thus, there are 30 moles of isophthalic acid residues among every 100 moles of acid residues. In another example, a polyester containing 30 mole % 2,2,4,4-tetramethyl-1,3-cyclobutanediol residues, based on the total diol residues, means the polyester contains 30 mole % 2,2,4,4-tetramethyl-1,3-cyclobutanediol residues out of a total of 100 mole % diol residues. Thus, there are 30 moles of 2,2,4,4-tetramethyl-1,3-cyclobutanediol residues among every 100 moles of diol residues.

In other aspects of the invention, the Tg of the polyesters useful in the invention can be at least one of the following ranges: 50 to 200° C.; 60 to 200° C.; 70 to 200° C.; 80 to 200° C.; 90 to 200° C.; 90 to 190° C.; 90 to 180° C.; 90 to 170° C.; 90 to 160° C.; 90 to 155° C.; 90 to 150° C.; 90 to 145° C.; 90 to 140° C.; 90 to 138° C.; 90 to 135° C.; 90 to 130° C.; 90 to 125° C.; 90 to 120° C.; 90 to 115° C.; 90 to 110° C.; 90 to 105° C.; 90 to 100° C.; 90 to 95° C.; 95 to 200° C.; 95 to 190° C.; 95 to 180° C.; 95 to 170° C.; 95 to 160° C.; 95 to 155° C.; 95 to 150° C.; 95 to 145° C.; 95 to 140° C.; 95 to 138° C.; 95 to 135° C.; 95 to 130° C.; 95 to 125° C.; 95 to 120° C.; 95 to 115° C.; 95 to 110° C.; 95 to 105° C.; 95 to less than 105° C.; 95 to 100° C.; 100 to 200° C.; 100 to 190° C.; 100 to 180° C.; 100 to 170° C.; 100 to 160° C.; 100 to 155° C.; 100 to 150° C.; 100 to 145° C.; 100 to 140° C.; 100 to 138° C.; 100 to 135° C.; 100 to 130° C.; 100 to 125° C.; 100 to 120° C.; 100 to 115° C.; 100 to 110° C.; 105 to 200° C.; 105 to 190° C.; 105 to 180° C.; 105 to 170° C.; 105 to 160° C.; 105 to 155° C.; 105 to 150° C.; 105 to 145° C.; 105 to 140° C.; 105 to 138° C.; 105 to 135° C.; 105 to 130° C.; 105 to 125° C.; 105 to 120° C.; 105 to 115° C.; 105 to 110° C.; greater than 105 to 125° C.; greater than 105 to 120° C.; greater than 105 to 115° C.; greater than 105 to 110° C.; 110 to 200° C.; 110 to 190° C.; 110 to 180° C.; 110 to 170° C.; 110 to 160° C.; 110 to 155° C.; 110 to 150° C.; 110 to 145° C.; 110 to 140° C.; 110 to 138° C.; 110 to 135° C.; 110 to 130° C.; 110 to 125° C.; 110 to 120° C.; 110 to 115° C.; 115 to 200° C.; 115 to 190° C.; 115 to 180° C.; 115 to 170° C.; 115 to 160° C.; 115 to 155° C.; 115 to 150° C.; 115 to 145° C.; 115 to 140° C.; 115 to 138° C.; 115 to 135° C.; 110 to 130° C.; 115 to 125° C.; 115 to 120° C.; 120 to 200° C.; 120 to 190° C.; 120 to 180° C.; 120 to 170° C.; 120 to 160° C.; 120 to 155° C.; 120 to 150° C.; 120 to 145° C.; 120 to 140° C.; 120 to 138° C.; 120 to 135° C.; 120 to 130° C.; 125 to 200° C.; 125 to 190° C.; 125 to 180° C.; 125 to 170° C.; 125 to 160° C.; 125 to 155° C.; 125 to 150° C.; 125 to 145° C.; 125 to 140° C.; 125 to 138° C.; 125 to 135° C.; 127 to 200° C.; 127 to 190° C.; 127 to 180° C.; 127 to 170° C.; 127 to 160° C.; 127 to 150° C.; 127 to 145° C.; 127 to 140° C.; 127 to 138° C.; 127 to 135° C.; 130 to 200° C.; 130 to 190° C.; 130 to 180° C.; 130 to 170° C.; 130 to 160° C.; 130 to 155° C.; 130 to 150° C.; 130 to 145° C.; 130 to 140° C.; 130 to 138° C.; 130 to 135° C.; 135 to 200° C.; 135 to 190° C.; 135 to 180° C.; 135 to 170° C.; 135 to 160° C.; 135 to 155° C.; 135 to 150° C.; 135 to 145° C.; 135 to 140° C.; 140 to 200° C.; 140 to 190° C.; 140 to 180° C.; 140 to 170° C.; 140 to 160° C.; 140 to 155° C.; 140 to 150° C.; 140 to 145° C.; 148 to 200° C.; 148 to 190° C.; 148 to 180° C.; 148 to 170° C.; 148 to 160° C.; 148 to 155° C.; 148 to 150° C.; 150 to 200° C.; 150 to 190° C.; 150 to 180° C.; 150 to 170° C.; 150 to 160° C.; 155 to 190° C.; 155 to 180° C.; 155 to 170° C.; and 155 to 165° C.

In other aspects of the invention, the glycol component for the polyesters useful in the invention include but are not limited to at least one of the following ranges: 0.01 to 99 mole % 1,4-cyclohexanedimethanol residues and 1 to 99.99 mole % residues of at least one modifying glycol; 1 to 99 mole % 1,4-cyclohexanedimethanol residues and 1 to 99 mole % residues of at least one modifying glycol; 5 to 99 mole % 1,4-cyclohexanedimethanol residues and 1 to 95 mole % at least one modifying glycol; 10 to 99 mole % 1,4-cyclohexanedimethanol residues and 1 to 90 mole % residues of at least one modifying glycol; 15 to 99 mole % 1,4-cyclohexanedimethanol residues and 1 to 85 mole % residues of at least one modifying glycol; 20 to 99 mole % 1,4-cyclohexanedimethanol residues and 1 to 80 mole % residues of at least one modifying glycol; 25 to 99 mole % 1,4-cyclohexanedimethanol residues and 1 to 75 mole % residues of at least one modifying glycol; 30 to 99 mole % 1,4-cyclohexanedimethanol residues and 1 to 70 mole % residues of at least one modifying glycol; 35 to 99 mole % 1,4-cyclohexanedimethanol residues and 1 to 65 mole % residues of at least one modifying glycol; 40 to 99 mole % 1,4-cyclohexanedimethanol residues and 1 to 60 mole % residues of at least one modifying glycol; 45 to 99 mole % 1,4-cyclohexanedimethanol residues and 1 to 55 mole % residues of at least one modifying glycol; 50 to 99 mole % 1,4-cyclohexanedimethanol residues and 1 to 50 mole % residues of at least one modifying glycol; 55 to 99 mole % 1,4-cyclohexanedimethanol residues and 1 to 45 mole % residues of at least one modifying glycol; 60 to 99 mole % 1,4-cyclohexanedimethanol residues and 1 to 40 mole % residues of at least one modifying glycol; 65 to 99 mole % 1,4-cyclohexanedimethanol residues and 1 to 35 mole % residues of at least one modifying glycol; 70 to 99 mole % 1,4-cyclohexanedimethanol residues and 1 to 30 mole % residues of at least one modifying glycol; 75 to 99 mole % 1,4-cyclohexanedimethanol residues and 1 to 25 mole % residues of at least one modifying glycol; 80 to 99 mole % 1,4-cyclohexanedimethanol residues and 1 to 20 mole % residues of at least one modifying glycol; 85 to 99 mole % 1,4-cyclohexanedimethanol residues and 1 to 15 mole % residues of at least one modifying glycol; 90 to 99 mole % 1,4-cyclohexanedimethanol residues and 1 to 10 mole % residues of at least one modifying glycol.

In other aspects of the invention, the glycol component for the polyesters useful in the invention include but are not limited to at least one of the following ranges: 0.01 to 95 mole % 1,4-cyclohexanedimethanol residues and 5 to 99.99 mole % residues of at least one modifying glycol; 1 to 95 mole % 1,4-cyclohexanedimethanol residues and 5 to 99 mole % residues of at least one modifying glycol; 5 to 95 mole % 1,4-cyclohexanedimethanol residues and 5 to 95 mole % residues of at least one modifying glycol; 10 to 95 mole % 1,4-cyclohexanedimethanol residues and 5 to 90 mole % residues of at least one modifying glycol; 15 to 95 mole % 1,4-cyclohexanedimethanol residues and 5 to 85 mole % residues of at least one modifying glycol; 20 to 95 mole % 1,4-cyclohexanedimethanol residues and 5 to 80 mole % residues of at least one modifying glycol; 25 to 95 mole % 1,4-cyclohexanedimethanol residues and 5 to 75 mole % residues of at least one modifying glycol; 30 to 95 mole % 1,4-cyclohexanedimethanol residues and 5 to 70 mole % residues of at least one modifying glycol; 35 to 95 mole % 1,4-cyclohexanedimethanol residues and 5 to 65 mole % residues of at least one modifying glycol; 40 to 95 mole % 1,4-cyclohexanedimethanol residues and 5 to 60 mole % residues of at least one modifying glycol; 45 to 95 mole % 1,4-cyclohexanedimethanol residues and 6 to 55 mole % residues of at least one modifying glycol; 50 to 95 mole % 1,4-cyclohexanedimethanol residues and 5 to 50 mole % residues of at least one modifying glycol; 55 to 95 mole % 1,4-cyclohexanedimethanol residues and 5 to 45 mole % residues of at least one modifying glycol; 60 to 95 mole % 1,4-cyclohexanedimethanol residues and 5 to 40 mole % residues of at least one modifying glycol; 65 to 95 mole % 1,4-cyclohexanedimethanol residues and 5 to 35 mole % residues of at least one modifying glycol; 70 to 95 mole % 1,4-cyclohexanedimethanol residues and 5 to 30 mole % residues of at least one modifying glycol; 75 to 95 mole % 1,4-cyclohexanedimethanol residues and 5 to 25 mole % residues of at least one modifying glycol; 80 to 95 mole % 1,4-cyclohexanedimethanol residues and 5 to 20 mole % residues of at least one modifying glycol; 85 to 95 mole % 1,4-cyclohexanedimethanol residues and 5 to 15 mole % residues of at least one modifying glycol; 90 to 95 mole % 1,4-cyclohexanedimethanol residues and 5 to 10 mole % residues of at least one modifying glycol.

In other aspects of the invention, the glycol component for the polyesters useful in the invention include but are not limited to at least one of the following ranges: 0.01 to 90 mole % 1,4-cyclohexanedimethanol residues and 10 to 99.99 mole % residues of at least one modifying glycol; 1 to 90 mole % 1,4-cyclohexanedimethanol residues and 10 to 99 mole % residues of at least one modifying glycol; 5 to 90 mole % 1,4-cyclohexanedimethanol residues and 10 to 95 mole % residues of at least one modifying glycol; 10 to 90 mole % 1,4-cyclohexanedimethanol residues and 10 to 90 mole % residues of at least one modifying glycol; 15 to 90 mole % 1,4-cyclohexanedimethanol residues and 10 to 85 mole % residues of at least one modifying glycol; 20 to 90 mole % 1,4-cyclohexanedimethanol residues and 10 to 80 mole % residues of at least one modifying glycol, 25 to 90 mole % 1,4-cyclohexanedimethanol residues and 10 to 75 mole % residues of at least one modifying glycol; 30 to 90 mole % 1,4-cyclohexanedimethanol residues and 10 to 70 mole % residues of at least one modifying glycol; 35 to 90 mole % 1,4-cyclohexanedimethanol residues and 10 to 65 mole % residues of at least one modifying glycol; 40 to 90 mole % 1,4-cyclohexanedimethanol residues and 10 to 60 mole % residues of at least one modifying glycol; 45 to 90 mole % 1,4-cyclohexanedimethanol residues and 10 to 55 mole % residues of at least one modifying glycol; 50 to 90 mole % 1,4-cyclohexanedimethanol residues and 10 to 50 mole % residues of at least one modifying glycol.

In other aspects of the invention, the glycol component for the polyesters useful in the invention include but are not limited to at least one of the following ranges: 55 to 90 mole % 1,4-cyclohexanedimetha60 to 90 mole % 1,4-cyclohexanedimethanol residues and 10 to 40 mole % residues of at least one modifying glycol; 65 to 90 mole % 1,4-cyclohexanedimethanol residues and 10 to 35 mole % residues of at least one modifying glycol; 70 to 90 mole % 1,4-cyclohexanedimethanol residues and 10 to 30 mole % residues of at least one modifying glycol; 75 to 90 mole % 1,4-cyclohexanedimethanol residues and 10 to 25 mole % residues of at least one modifying glycol; 80 to 90 mole % 1,4-cyclohexanedimethanol residues and 10 to 20 mole % residues of at least one modifying glycol; 85 to 90 mole % 1,4-cyclohexanedimethanol residues and 10 to 15 mole % residues of at least one modifying glycol.

In other aspects of the invention, the glycol component for the polyesters useful in the invention include but are not limited to at least one of the following ranges: 0.01 to 85 mole % 1,4-cyclohexanedimethanol residues and 15 to 99.99 mole % residues of at least one modifying glycol; 1 to 85 mole % 1,4-cyclohexanedimethanol residues and 15 to 99 mole % residues of at least one modifying glycol; 5 to 85 mole % 1,4-cyclohexanedimethanol residues and 15 to 95 mole % residues of at least one modifying glycol; 10 to 85 mole % 1,4-cyclohexanedimethanol residues and 15 to 90 mole % residues of at least one modifying glycol; 15 to 85 mole % 1,4-cyclohexanedimethanol residues and 15 to 85 mole % residues of at least one modifying glycol; 20 to 85 mole % 1,4-cyclohexanedimethanol residues and 15 to 80 mole % residues of at least one modifying glycol; 25 to 85 mole % 1,4-cyclohexanedimethanol residues and 15 to 75 mole % residues of at least one modifying glycol; 30 to 85 mole % 1,4-cyclohexanedimethanol residues and 15 to 70 mole % residues of at least one modifying glycol; 35 to 85 mole % 1,4-cyclohexanedimethanol residues and 15 to 65 mole % residues of at least one modifying glycol; 40 to 85 mole % 1,4-cyclohexanedimethanol residues and 15 to 60 mole % residues of at least one modifying glycol; 45 to 85 mole % 1,4-cyclohexanedimethanol residues 15 to 55 mole % residues of at least one modifying glycol; 50 to 85 mole % 1,4-cyclohexanedimethanol residues and 15 to 50 mole % residues of at least one modifying glycol.

In other aspects of the invention, the glycol component for the polyesters useful in the invention include but are not limited to at least one of the following ranges: 55 to 85 mole % 1,4-cyclohexanedimethanol residues and 15 to 45 mole % residues of at least one modifying glycol; 60 to 85 mole % 1,4-cyclohexanedimethanol residues and 15 to 40 mole % residues of at least one modifying glycol; 65 to 85 mole % 1,4-cyclohexanedimethanol residues and 15 to 35 mole % residues of at least one modifying glycol; 70 to 85 mole % 1,4-cyclohexanedimethanol residues and 15 to 30 mole % residues of at least one modifying glycol; 75 to 85 mole % 1,4-cyclohexanedimethanol residues and 15 to 25 mole % residues of at least one modifying glycol; 80 to 85 mole % 1,4-cyclohexanedimethanol residues and 15 to 20 mole % residues of at least one modifying glycol.

In other aspects of the invention, the glycol component for the polyesters useful in the invention include but are not limited to at least one of the following ranges: 0.01 to 80 mole % 1,4-cyclohexanedimethanol residues and 20 to 99.99 mole % residues of at least one modifying glycol; 1 to 80 mole % 1,4-cyclohexanedimethanol residues and 20 to 99 mole % residues of at least one modifying glycol; 5 to 80 mole % 1,4-cyclohexanedimethanol residues and 20 to 95 mole % residues of at least one modifying glycol; 10 to 80 mole % 1,4-cyclohexanedimethanol residues and 20 to 90 mole % residues of at least one modifying glycol; 15 to 80 mole % 1,4-cyclohexanedimethanol residues and 20 to 85 mole % residues of at least one modifying glycol; 20 to 80 mole % residues of at least one modifying glycol; 25 to 80 mole % 1,4-cyclohexanedimethanol residues and 20 to 75 mole % residues of at least one modifying glycol; 30 to 80 mole % 1,4-cyclohexanedimethanol residues and 20 to 70 mole % residues of at least one modifying glycol; 35 to 80 mole % 1,4-cyclohexanedimethanol residues and 20 to 65 mole % residues of at least one modifying glycol; 40 to 80 mole % 1,4-cyclohexanedimethanol residues and 20 to 60 mole % residues of at least one modifying glycol; 45 to 80 mole % 1,4-cyclohexanedimethanol residues and 20 to 55 mole % residues of at least one modifying glycol; 50 to 80 mole % 1,4-cyclohexanedimethanol residues and 20 to 50 mole % residues of at least one modifying glycol; 55 to 80 mole % 1,4-cyclohexanedimethanol residues and 20 to 45 mole % residues of at least one modifying glycol; 60 to 80 mole % 1,4-cyclohexanedimethanol residues and 20 to 40 mole % residues of at least one modifying glycol; 65 to 80 mole % 1,4-cyclohexanedimethanol residues and 20 to 35 mole % residues of at least one modifying glycol; 70 to 80 mole % 1,4-cyclohexanedimethanol residues and 20 to 30 mole % residues of at least one modifying glycol; and 75 to 80 mole % 1,4-cyclohexanedimethanol residues and 20 to 25 mole % residues of at least one modifying glycol.

In other aspects of the invention, the glycol component for the polyesters useful in the invention include but are not limited to at least one of the following ranges: 0.01 to 75 mole % 1,4-cyclohexanedimethanol residues and 25 to 99.99 mole % residues of at least one modifying glycol; 1 to 75 mole % 1,4-cyclohexanedimethanol residues and 25 to 99 mole % residues of at least one modifying glycol; 5 to 75 mole % 1,4-cyclohexanedimethanol residues and 25 to 95 mole % residues of at least one modifying glycol; 10 to 75 mole % 1,4-cyclohexanedimethanol residues and 25 to 90 mole % residues of at least one modifying glycol; 15 to 75 mole % 1,4-cyclohexanedimethanol residues and 25 to 85 mole % residues of at least one modifying glycol; 20 to 75 mole % 1,4-cyclohexanedimethanol residues and 25 to 80 mole % residues of at least one modifying glycol; 25 to 75 mole % 1,4-cyclohexanedimethanol residues and 25 to 75 mole % residues of at least one modifying glycol; 30 to 75 mole % 1,4-cyclohexanedimethanol residues and 25 to 70 mole % residues of at least one modifying glycol; 35 to 75 mole % % 1,4-cyclohexanedimethanol residues and 25 to 65 mole % residues of at least one modifying glycol; 40 to 75 mole % 1,4-cyclohexanedimethanol residues and 25 to 60 mole % residues of at least one modifying glycol; 45 to 75 mole % 1,4-cyclohexanedimethanol residues and 25 to 55 mole % residues of at least one modifying glycol; 50 to 75 mole % 1,4-cyclohexanedimethanol residues and 25 to 50 mole % residues of at least one modifying glycol; 55 to 75 mole % 1,4-cyclohexanedimethanol residues and 25 to 45 mole % residues of at least one modifying glycol; 60 to 75 mole % 1,4-cyclohexanedimethanol residues and 25 to 40 mole % residues of at least one modifying glycol; 65 to 75 mole % 1,4-cyclohexanedimethanol residues and 25 to 35 mole % residues of at least one modifying glycol; and 70 to 75 mole % 1,4-cyclohexanedimethanol residues and 25 to 30 mole % residues of at least one modifying glycol.

In other aspects of the invention, the glycol component for the polyesters useful in the invention include but are not limited to at least one of the following ranges: 0.01 to 65 mole % 1,4-cyclohexanedimethanol residues and 35 to 99.99 mole % residues of at least one modifying glycol; 1 to 65 mole % 1,4-cyclohexanedimethanol residues and 35 to 99 mole % residues of at least one modifying glycol; 5 to 65 mole % 1,4-cyclohexanedimethanol residues and 35 to 95 mole % residues of at least one modifying glycol; 10 to 65 mole % 1,4-cyclohexanedimethanol residues and 35 to 90 mole % residues of at least one modifying glycol; 15 to 65 mole % 1,4-cyclohexanedimethanol residues and 35 to 85 mole % residues of at least one modifying glycol; 20 to 65 mole % 1,4-cyclohexanedimethanol residues and 35 to 80 mole % residues of at least one modifying glycol, 25 to 65 mole % 1,4-cyclohexanedimethanol residues and 35 to 75 mole % residues of at least one modifying glycol; 30 to 65 mole % 1,4-cyclohexanedimethanol residues and 35 to 70 mole % residues of at least one modifying glycol; 35 to 65 mole % 1,4-cyclohexanedimethanol residues and 35 to 65 mole % residues of at least one modifying glycol; 40 to 65 mole % 1,4-cyclohexanedimethanol residues and 35 to 60 mole % residues of at least one modifying glycol; 45 to 65 mole % 1,4-cyclohexanedimethanol residues and 35 to 55 mole % residues of at least one modifying glycol; 50 to 65 mole % 1,4-cyclohexanedimethanol residues and 35 to 50 mole % residues of at least one modifying glycol; 55 to 65 mole % 1,4-cyclohexanedimethanol residues and 35 to 45 mole % residues of at least one modifying glycol; and 60 to 65 mole % 1,4-cyclohexanedimethanol residues and 35 to 40 mole % residues of at least one modifying glycol.

In other aspects of the invention, the glycol component for the polyesters useful in the invention include but are not limited to at least one of the following ranges: 0.01 to 60 mole % 1,4-cyclohexanedimethanol residues and 40 to 99.99 mole % residues of at least one modifying glycol; 1 to 60 mole % 1,4-cyclohexanedimethanol residues and 40 to 99 mole % residues of at least one modifying glycol; 5 to 60 mole % 1,4-cyclohexanedimethanol residues and 40 to 95 mole % residues of at least one modifying glycol; 10 to 60 mole % 1,4-cyclohexanedimethanol residues and 40 to 90 mole % residues of at least one modifying glycol; 15 to 60 mole % 1,4-cyclohexanedimethanol residues and 40 to 85 mole % residues of at least one modifying glycol; 20 to 60 mole % 1,4-cyclohexanedimethanol residues and 40 to 80 mole % residues of at least one modifying glycol; 25 to 60 mole % 1,4-cyclohexanedimethanol residues and 40 to 75 mole % residues of at least one modifying glycol; 30 to 60 mole % 1,4-cyclohexanedimethanol residues and 40 to 70 mole % residues of at least one modifying glycol; 35 to 60 mole % 1,4-cyclohexanedimethanol residues and 40 to 65 mole % residues of at least one modifying glycol; 40 to 60 mole % 1,4-cyclohexanedimethanol residues and 40 to 60 mole % residues of at least one modifying glycol; 45 to 60 mole % 1,4-cyclohexanedimethanol residues and 40 to 55 mole % residues of at least one modifying glycol; 50 to 60 mole % 1,4-cyclohexanedimethanol residues and 40 to 50 mole % residues of at least one modifying glycol; 55 to 60 mole % 1,4-cyclohexanedimethanol residues and 40 to 45 mole % residues of at least one modifying glycol.

In other aspects of the invention, the glycol component for the polyesters useful in the invention include but are not limited to at least one of the following ranges: 0.01 to 55 mole % 1,4-cyclohexanedimethanol residues and 45 to 99.99 mole % residues of at least one modifying glycol; 1 to 55 mole % 1,4-cyclohexanedimethanol residues and 45 to 99 mole % residues of at least one modifying glycol; 5 to 55 mole % 1,4-cyclohexanedimethanol residues and 45 to 95 mole % residues of at least one modifying glycol; 10 to 55 mole % 1,4-cyclohexanedimethanol residues and 45 to 90 mole % residues of at least one modifying glycol; 15 to 55 mole % 1,4-cyclohexanedimethanol residues and 45 to 85 mole % residues of at least one modifying glycol; 20 to 55 mole % 1,4-cyclohexanedimethanol residues and 45 to 80 mole % residues of at least one modifying glycol; 25 to 55 mole % 1,4-cyclohexanedimethanol residues and 45 to 75 mole % residues of at least one modifying glycol; 30 to 55 mole % 1,4-cyclohexanedimethanol residues and 45 to 70 mole % residues of at least one modifying glycol; 35 to 55 mole % 1,4-cyclohexanedimethanol residues and 45 to 65 mole % residues of at least one modifying glycol; 40 to 55 mole % 1,4-cyclohexanedimethanol residues and 45 to 60 mole % residues of at least one modifying glycol; 45 to 55 mole % 1,4-cyclohexanedimethanol residues and 45 to 55 mole % residues of at least one modifying glycol; and 50 to 55 mole % 1,4-cyclohexanedimethanol residues and 45 to 50 mole % residues of at least one modifying glycol.

In other aspects of the invention, the glycol component for the polyesters useful in the invention include but are not limited to at least one of the following ranges: 0.01 to 50 mole % 1,4-cyclohexanedimethanol residues and 50 to 99.99 mole % residues of at least one modifying glycol; 1 to 50 mole % 1,4-cyclohexanedimethanol residues and 50 to 99 mole % residues of at least one modifying glycol; 5 to 50 mole % 1,4-cyclohexanedimethanol residues and 50 to 95 mole % residues of at least one modifying glycol; 10 to 50 mole % 1,4-cyclohexanedimethanol residues and 50 to 90 mole % residues of at least one modifying glycol; 15 to 50 mole % 1,4-cyclohexanedimethanol residues and 50 to 85 mole % residues of at least one modifying glycol; 20 to 50 mole % 1,4-cyclohexanedimethanol residues and 50 to 80 mole % residues of at least one modifying glycol 25 to 50 mole % 1,4-cyclohexanedimethanol residues and 50 to 75 mole % residues of at least one modifying glycol; 30 to 50 mole % 1,4-cyclohexanedimethanol residues and 50 to 70 mole % residues of at least one modifying glycol; 35 to 50 mole % 1,4-cyclohexanedimethanol residues and 50 to 65 mole % residues of at least one modifying glycol; 40 to 50 mole % 1,4-cyclohexanedimethanol residues and 50 to 60 mole % residues of at least one modifying glycol; and 45 to 50 mole % 1,4-cyclohexanedimethanol residues and 50 to 55 mole % residues of at least one modifying glycol.

In other aspects of the invention, the glycol component for the polyesters useful in the invention include but are not limited to at least one of the following ranges: 0.01 to 45 mole % 1,4-cyclohexanedimethanol residues and 55 to 99.99 mole % residues of at least one modifying glycol; 1 to 45 mole % 1,4-cyclohexanedimethanol residues and 55 to 99 mole % residues of at least one modifying glycol; 5 to 45 mole % 1,4-cyclohexanedimethanol residues and 50 to 95 mole % residues of at least one modifying glycol; 10 to 45 and 55 to 95 mole % residues of at least one modifying glycol mole % 1,4-cyclohexanedimethanol residues; 15 to 45 mole % 1,4-cyclohexanedimethanol residues and 55 to 85 mole % residues of at least one modifying glycol; 20 to 45 mole % 1,4-cyclohexanedimethanol residues and 55 to 80 mole % residues of at least one modifying glycol; 25 to 45 mole % 1,4-cyclohexanedimethanol residues and 55 to 75 mole % residues of at least one modifying glycol; 30 to 45 mole % 1,4-cyclohexanedimethanol residues and 55 to 65 mole % residues of at least one modifying glycol; 35 to 45 mole % 1,4-cyclohexanedimethanol residues and 55 to 65 mole % residues of at least one modifying glycol; 40 to 45 mole % 1,4-cyclohexanedimethanol residues and 55 to 60 mole % residues of at least one modifying glycol.

In other aspects of the invention, the glycol component for the polyesters useful in the invention include but are not limited to at least one of the following ranges: 0.01 to 40 mole % 1,4-cyclohexanedimethanol residues and 60 to 99.99 mole % residues of at least one modifying glycol; 1 to 40 mole % 1,4-cyclohexanedimethanol residues and 60 to 99 mole % residues of at least one modifying glycol; 5 to 40 mole % 1,4-cyclohexanedimethanol residues and 60 to 95 mole % residues of at least one modifying glycol; 10 to 40 mole % 1,4-cyclohexanedimethanol residues and 60 to 90 mole % residues of at least one modifying glycol; 15 to 40 mole % 1,4-cyclohexanedimethanol residues and 60 to 85 mole % residues of at least one modifying glycol; 20 to 40 mole % 1,4-cyclohexanedimethanol residues and 60 to 80 mole % residues of at least one modifying glycol; 25 to 40 mole % 1,4-cyclohexanedimethanol residues and 60 to 75 mole % residues of at least one modifying glycol; 30 to 40 mole % 1,4-cyclohexanedimethanol residues and 60 to 70 mole % residues of at least one modifying glycol; 35 to 40 mole % 1,4-cyclohexanedimethanol residues and 60 to 65 mole % residues of at least one modifying glycol.

In other aspects of the invention, the glycol component for the polyesters useful in the invention include but are not limited to at least one of the following ranges: 0.01 to 35 mole % 1,4-cyclohexanedimethanol residues and 65 to 99.99 mole % residues of at least one modifying glycol; 1 to 35 mole % 1,4-cyclohexanedimethanol residues and 65 to 99 mole % residues of at least one modifying glycol; 5 to 35 mole % 1,4-cyclohexanedimethanol residues and 65 to 95 mole % residues of at least one modifying glycol; 10 to 35 mole % 1,4-cyclohexanedimethanol residues and 65 to 90 mole % residues of at least one modifying glycol; 15 to 35 mole % 1,4-cyclohexanedimethanol residues and 65 to 85 mole % residues of at least one modifying glycol; 20 to 35 mole % 1,4-cyclohexanedimethanol residues and 65 to 80 mole % residues of at least one modifying glycol; 25 to 35 mole % 1,4-cyclohexanedimethanol residues and 65 to 75 mole % residues of at least one modifying glycol; 30 to 35 mole % 1,4-cyclohexanedimethanol residues and 65 to 70 mole % residues of at least one modifying glycol.

In other aspects of the invention, the glycol component for the polyesters useful in the invention include but are not limited to at least one of the following ranges: 0.01 to 30 mole % 1,4-cyclohexanedimethanol residues and 70 to 99.99 mole % mole % residues of at least one modifying glycol; 1 to 30 mole % 1,4-cyclohexanedimethanol residues and 70 to 99 mole % residues of at least one modifying glycol; 5 to 30 mole % 1,4-cyclohexanedimethanol residues and 70 to 95 mole % residues of at least one modifying glycol; 10 to 30 mole % 1,4-cyclohexanedimethanol residues and 70 to 90 mole % residues of at least one modifying glycol; 15 to 30 mole % 1,4-cyclohexanedimethanol residues and 70 to 85 mole % residues of at least one modifying glycol; 20 to 30 mole % 1,4-cyclohexanedimethanol residues and 70 to 80 mole % residues of at least one modifying glycol; 25 to 30 mole % 1,4-cyclohexanedimethanol residues and 70 to 75 mole % residues of at least one modifying glycol.

In other aspects of the invention, the glycol component for the polyesters useful in the invention include but are not limited to at least one of the following ranges: 0.01 to 25 mole % 1,4-cyclohexanedimethanol residues and 75 to 99.99 mole % residues of at least one modifying glycol; 1 to 25 mole % 1,4-cyclohexanedimethanol residues and 75 to 99 mole % residues of at least one modifying glycol; 5 to 25 mole % 1,4-cyclohexanedimethanol residues and 75 to 95 mole % residues of at least one modifying glycol; 10 to 25 mole % 1,4-cyclohexanedimethanol residues and 75 to 90 mole % residues of at least one modifying glycol; 15 to 25 mole % 1,4-cyclohexanedimethanol residues and 75 to 85 mole % residues of at least one modifying glycol; 20 to 25 mole % 1,4-cyclohexanedimethanol residues and 75 to 80 mole % residues of at least one modifying glycol.

In other aspects of the invention, the glycol component for the polyesters useful in the invention include but are not limited to at least one of the following ranges: 0.01 to 20 mole % 1,4-cyclohexanedimethanol residues and 80 to 99.99 mole % residues of at least one modifying glycol; 1 to 20 mole % 1,4-cyclohexanedimethanol residues and 80 to 99 mole % residues of at least one modifying glycol; 5 to 20 mole % 1,4-cyclohexanedimethanol residues and 80 to 95 mole % residues of at least one modifying glycol; 10 to 20 mole % 1,4-cyclohexanedimethanol residues and 80 to 90 mole % residues of at least one modifying glycol; and 15 to 20 mole % 1,4-cyclohexanedimethanol residues and 80 to 85 mole % residues of at least one modifying glycol.

In other aspects of the invention, the glycol component for the polyesters useful in the invention include but are not limited to at least one of the following ranges: 0.01 to 15 mole % 1,4-cyclohexanedimethanol residues and 85 to 99.99 mole % residues of at least one modifying glycol; 1 to 15 mole % 1,4-cyclohexanedimethanol residues and 85 to 99 mole % residues of at least one modifying glycol; 5 to 15 mole % 1,4-cyclohexanedimethanol residues and 85 to 95 mole % residues of at least one modifying glycol; and 10 to 15 mole % 1,4-cyclohexanedimethanol residues and 85 to 90 mole % residues of at least one modifying glycol.

In other aspects of the invention, the glycol component for the polyesters useful in the invention include but are not limited to at least one of the following ranges: 0.01 to 10 mole % 1,4-cyclohexanedimethanol residues and 90 to 99.99 mole % residues of at least one modifying glycol; 1 to 10 mole % 1,4-cyclohexanedimethanol residues and 90 to 99 mole % residues of at least one modifying glycol; 5 to 10 mole % 1,4-cyclohexanedimethanol residues and 90 to 95 mole % residues of at least one modifying glycol; 0.01 to 5 mole % 1,4-cyclohexanedimethanol residues and 95 to 99.99 mole % residues of at least one modifying glycol and 1 to 5 mole % 1,4-cyclohexanedimethanol residues and 95 to 99 mole % residues of at least one modifying glycol.

In other aspects of the invention, the glycol component for the polyesters useful in the invention include but are not limited to at least one of the following ranges: 0.01 to 99 mole % 1,4-cyclohexanedimethanol residues and 1 to 99.99 mole % ethylene glycol residues; 1 to 99 mole % 1,4-cyclohexanedimethanol residues and 1 to 99 mole % ethylene glycol residues; 5 to 99 mole % 1,4-cyclohexanedimethanol residues and 1 to 95 mole % ethylene glycol residues; 10 to 99 mole % 1,4-cyclohexanedimethanol residues and 1 to 90 mole % ethylene glycol residues; 15 to 99 mole % 1,4-cyclohexanedimethanol residues and 1 to 85 mole % ethylene glycol residues; 20 to 99 mole % 1,4-cyclohexanedimethanol residues and 1 to 80 mole % ethylene glycol residues; 25 to 99 mole % 1,4-cyclohexanedimethanol residues and 1 to 75 mole % ethylene glycol residues; 30 to 99 mole % 1,4-cyclohexanedimethanol residues and 1 to 70 mole % ethylene glycol residues; 35 to 99 mole % 1,4-cyclohexanedimethanol residues and 1 to 65 mole % ethylene glycol residues; 40 to 99 mole % 1,4-cyclohexanedimethanol residues and 1 to 60 mole % ethylene glycol residues; 45 to 99 mole % 1,4-cyclohexanedimethanol residues and 1 to 55 mole % ethylene glycol residues; 50 to 99 mole % 1,4-cyclohexanedimethanol residues and 1 to 50 mole % ethylene glycol residues; 55 to 99 mole % 1,4-cyclohexanedimethanol residues and 1 to 45 mole % ethylene glycol residues; 60 to 99 mole % 1,4-cyclohexanedimethanol residues and 1 to 40 mole % ethylene glycol residues; 65 to 99 mole % 1,4-cyclohexanedimethanol residues and 1 to 35 mole % ethylene glycol residues; 70 to 99 mole % 1,4-cyclohexanedimethanol residues and 1 to 30 mole % ethylene glycol residues; 75 to 99 mole % 1,4-cyclohexanedimethanol residues and 1 to 25 mole % ethylene glycol residues; 80 to 99 mole % 1,4-cyclohexanedimethanol residues and 1 to 20 mole % ethylene glycol residues; 85 to 99 mole % 1,4-cyclohexanedimethanol residues and 1 to 15 mole % ethylene glycol residues; 90 to 99 mole % 1,4-cyclohexanedimethanol residues and 1 to 10 mole % ethylene glycol residues.

In other aspects of the invention, the glycol component for the polyesters useful in the invention include but are not limited to at least one of the following ranges: 0.01 to 95 mole % 1,4-cyclohexanedimethanol residues and 5 to 99.99 mole % ethylene glycol residues; 1 to 95 mole % 1,4-cyclohexanedimethanol residues and 5 to 99 mole % ethylene glycol residues; 5 to 95 mole % 1,4-cyclohexanedimethanol residues and 5 to 95 mole % ethylene glycol residues; 10 to 95 mole % 1,4-cyclohexanedimethanol residues and 5 to 90 mole % ethylene glycol residues; 15 to 95 mole % 1,4-cyclohexanedimethanol residues and 5 to 85 mole % ethylene glycol residues; 20 to 95 mole % 1,4-cyclohexanedimethanol residues and 5 to 80 mole % ethylene glycol residues; 25 to 95 mole % 1,4-cyclohexanedimethanol residues and 5 to 75 mole % ethylene glycol residues; 30 to 95 mole % 1,4-cyclohexanedimethanol residues and 5 to 70 mole % ethylene glycol residues; 35 to 95 mole % 1,4-cyclohexanedimethanol residues and 5 to 65 mole % ethylene glycol residues; 40 to 95 mole % 1,4-cyclohexanedimethanol residues and 5 to 60 mole % ethylene glycol residues; 45 to 95 mole % 1,4-cyclohexanedimethanol residues and 6 to 55 mole % ethylene glycol residues; 50 to 95 mole % 1,4-cyclohexanedimethanol residues and 5 to 50 mole % ethylene glycol residues; 55 to 95 mole % 1,4-cyclohexanedimethanol residues and 5 to 45 mole % ethylene glycol residues; 60 to 95 mole % 1,4-cyclohexanedimethanol residues and 5 to 40 mole % ethylene glycol residues; 65 to 95 mole % 1,4-cyclohexanedimethanol residues and 5 to 35 mole % ethylene glycol residues; 70 to 95 mole % 1,4-cyclohexanedimethanol residues and 5 to 30 mole % ethylene glycol residues; 75 to 95 mole % 1,4-cyclohexanedimethanol residues and 5 to 25 mole % ethylene glycol residues; 80 to 95 mole % 1,4-cyclohexanedimethanol residues and 5 to 20 mole % ethylene glycol residues; 85 to 95 mole % 1,4-cyclohexanedimethanol residues and 5 to 15 mole % ethylene glycol residues; 90 to 95 mole % 1,4-cyclohexanedimethanol residues and 5 to 10 mole % ethylene glycol residues.

In other aspects of the invention, the glycol component for the polyesters useful in the invention include but are not limited to at least one of the following ranges: 0.01 to 90 mole % 1,4-cyclohexanedimethanol residues and 10 to 99.99 mole % ethylene glycol residues; 1 to 90 mole % 1,4-cyclohexanedimethanol residues and 10 to 99 mole % ethylene glycol residues; 5 to 90 mole % 1,4-cyclohexanedimethanol residues and 10 to 95 mole % ethylene glycol residues; 10 to 90 mole % 1,4-cyclohexanedimethanol residues and 10 to 90 mole % ethylene glycol residues; 15 to 90 mole % 1,4-cyclohexanedimethanol residues and 10 to 85 mole % ethylene glycol residues; 20 to 90 mole % 1,4-cyclohexanedimethanol residues and 10 to 80 mole % ethylene glycol residues, 25 to 90 mole % 1,4-cyclohexanedimethanol residues and 10 to 75 mole % ethylene glycol residues; 30 to 90 mole % 1,4-cyclohexanedimethanol residues and 10 to 70 mole % ethylene glycol residues; 35 to 90 mole % 1,4-cyclohexanedimethanol residues and 10 to 65 mole % ethylene glycol residues; 40 to 90 mole % 1,4-cyclohexanedimethanol residues and 10 to 60 mole % ethylene glycol residues; 45 to 90 mole % 1,4-cyclohexanedimethanol residues and 10 to 55 mole % ethylene glycol residues; 50 to 90 mole % 1,4-cyclohexanedimethanol residues and 10 to 50 mole % ethylene glycol residues.

In other aspects of the invention, the glycol component for the polyesters useful in the invention include but are not limited to at least one of the following ranges: 55 to 90 mole % 1,4-cyclohexanedimethanol residues and 10 to 45 mole % ethylene glycol residues; 60 to 90 mole % 1,4-cyclohexanedimethanol residues and 10 to 40 mole % ethylene glycol residues; 65 to 90 mole % 1,4-cyclohexanedimethanol residues and 10 to 35 mole % ethylene glycol residues; 70 to 90 mole % 1,4-cyclohexanedimethanol residues and 10 to 30 mole % ethylene glycol residues; 75 to 90 mole % 1,4-cyclohexanedimethanol residues and 10 to 25 mole % ethylene glycol residues; 80 to 90 mole % 1,4-cyclohexanedimethanol residues and 10 to 20 mole % ethylene glycol residues; 85 to 90 mole % 1,4-cyclohexanedimethanol residues and 10 to 15 mole % ethylene glycol residues.

In other aspects of the invention, the glycol component for the polyesters useful in the invention include but are not limited to at least one of the following ranges: 0.01 to 85 mole % 1,4-cyclohexanedimethanol residues and 15 to 99.99 mole % ethylene glycol residues; 1 to 85 mole % 1,4-cyclohexanedimethanol residues and 15 to 99 mole % ethylene glycol residues; 5 to 85 mole % 1,4-cyclohexanedimethanol residues and 15 to 95 mole % ethylene glycol residues; 10 to 85 mole % 1,4-cyclohexanedimethanol residues and 15 to 90 mole % ethylene glycol residues; 15 to 85 mole % 1,4-cyclohexanedimethanol residues and 15 to 85 mole % ethylene glycol residues; 20 to 85 mole % 1,4-cyclohexanedimethanol residues and 15 to 80 mole % ethylene glycol residues; 25 to 85 mole % 1,4-cyclohexanedimethanol residues and 15 to 75 mole % ethylene glycol residues; 30 to 85 mole % 1,4-cyclohexanedimethanol residues and 15 to 70 mole % ethylene glycol residues; 35 to 85 mole % 1,4-cyclohexanedimethanol residues and 15 to 65 mole % ethylene glycol residues; 40 to 85 mole % 1,4-cyclohexanedimethanol residues and 15 to 60 mole % ethylene glycol residues; 45 to 85 mole % 1,4-cyclohexanedimethanol residues 15 to 55 mole % ethylene glycol residues; 50 to 85 mole % 1,4-cyclohexanedimethanol residues and 15 to 50 mole % ethylene glycol residues.

In other aspects of the invention, the glycol component for the polyesters useful in the invention include but are not limited to at least one of the following ranges: 55 to 85 mole % 1,4-cyclohexanedimethanol residues and 15 to 45 mole % ethylene glycol residues; 60 to 85 mole % 1,4-cyclohexanedimethanol residues and 15 to 40 mole % ethylene glycol residues; 65 to 85 mole % 1,4-cyclohexanedimethanol residues and 15 to 35 mole % ethylene glycol residues; 70 to 85 mole % 1,4-cyclohexanedimethanol residues and 15 to 30 mole % ethylene glycol residues; 75 to 85 mole % 1,4-cyclohexanedimethanol residues and 15 to 25 mole % ethylene glycol residues; 80 to 85 mole % 1,4-cyclohexanedimethanol residues and 15 to 20 mole % ethylene glycol residues.

In other aspects of the invention, the glycol component for the polyesters useful in the invention include but are not limited to at least one of the following ranges: 0.01 to 80 mole % 1,4-cyclohexanedimethanol residues and 20 to 99.99 mole % ethylene glycol residues; 1 to 80 mole % 1,4-cyclohexanedimethanol residues and 20 to 99 mole % ethylene glycol residues; 5 to 80 mole % 1,4-cyclohexanedimethanol residues and 20 to 95 mole % ethylene glycol residues; 10 to 80 mole % 1,4-cyclohexanedimethanol residues and 20 to 90 mole % ethylene glycol residues; 15 to 80 mole % 1,4-cyclohexanedimethanol residues and 20 to 85 mole % ethylene glycol residues; 20 to 80 mole % 1,4-cyclohexanedimethanol residues and 20 to 80 mole % ethylene glycol residues; 25 to 80 mole % 1,4-cyclohexanedimethanol residues and 20 to 75 mole % ethylene glycol residues; 30 to 80 mole % 1,4-cyclohexanedimethanol residues and 20 to 70 mole % ethylene glycol residues; 35 to 80 mole % 1,4-cyclohexanedimethanol residues and 20 to 65 mole % ethylene glycol residues; 40 to 80 mole % 1,4-cyclohexanedimethanol residues and 20 to 60 mole % ethylene glycol residues; 45 to 80 mole % 1,4-cyclohexanedimethanol residues and 20 to 55 mole % ethylene glycol residues; 50 to 80 mole % 1,4-cyclohexanedimethanol residues and 20 to 50 mole % ethylene glycol residues; 55 to 80 mole % 1,4-cyclohexanedimethanol residues and 20 to 45 mole % ethylene glycol residues; 60 to 80 mole % 1,4-cyclohexanedimethanol residues and 20 to 40 mole % ethylene glycol residues; 65 to 80 mole % 1,4-cyclohexanedimethanol residues and 20 to 35 mole % ethylene glycol residues; 70 to 80 mole % 1,4-cyclohexanedimethanol residues and 20 to 30 mole % ethylene glycol residues; and 75 to 80 mole % 1,4-cyclohexanedimethanol residues and 20 to 25 mole % ethylene glycol residues.

In other aspects of the invention, the glycol component for the polyesters useful in the invention include but are not limited to at least one of the following ranges: 0.01 to 75 mole % 1,4-cyclohexanedimethanol residues and 25 to 99.99 mole % ethylene glycol residues; 1 to 75 mole % 1,4-cyclohexanedimethanol residues and 25 to 99 mole % ethylene glycol residues; 5 to 75 mole % 1,4-cyclohexanedimethanol residues and 25 to 95 mole % ethylene glycol residues; 10 to 75 mole % 1,4-cyclohexanedimethanol residues and 25 to 90 mole % ethylene glycol residues; 15 to 75 mole % 1,4-cyclohexanedimethanol residues and 25 to 85 mole % ethylene glycol residues; 20 to 75 mole % 1,4-cyclohexanedimethanol residues and 25 to 80 mole % ethylene glycol residues; 25 to 75 mole % 1,4-cyclohexanedimethanol residues and 25 to 75 mole % ethylene glycol residues; 30 to 75 mole % 1,4-cyclohexanedimethanol residues and 25 to 70 mole % ethylene glycol residues; 35 to 75 mole % 1,4-cyclohexanedimethanol residues and 25 to 65 mole % ethylene glycol residues; 40 to 75 mole % 1,4-cyclohexanedimethanol residues and 25 to 60 mole % ethylene glycol residues; 45 to 75 mole % 1,4-cyclohexanedimethanol residues and 25 to 55 mole % ethylene glycol residues; 50 to 75 mole % 1,4-cyclohexanedimethanol residues and 25 to 50 mole % ethylene glycol residues; 55 to 75 mole % 1,4-cyclohexanedimethanol residues and 25 to 45 mole % ethylene glycol residues; 60 to 75 mole % 1,4-cyclohexanedimethanol residues and 25 to 40 mole % ethylene glycol residues; 65 to 75 mole % 1,4-cyclohexanedimethanol residues and 25 to 35 mole % ethylene glycol residues; and 70 to 75 mole % 1,4-cyclohexanedimethanol residues and 25 to 30 mole % ethylene glycol residues.

In other aspects of the invention, the glycol component for the polyesters useful in the invention include but are not limited to at least one of the following ranges: 0.01 to 70 mole % 1,4-cyclohexanedimethanol residues and 30 to 99.99 mole % ethylene glycol residues; 1 to 70 mole % 1,4-cyclohexanedimethanol residues and 30 to 99 mole % ethylene glycol residues; 5 to 70 mole % 1,4-cyclohexanedimethanol residues and 30 to 95 mole % ethylene glycol residues; 10 to 70 mole % 1,4-cyclohexanedimethanol residues and 30 to 90 mole % ethylene glycol residues; 15 to 70 mole % 1,4-cyclohexanedimethanol residues and 30 to 85 mole % ethylene glycol residues; 20 to 70 mole % 1,4-cyclohexanedimethanol residues and 30 to 80 mole % ethylene glycol residues; 25 to 70 mole % 1,4-cyclohexanedimethanol residues and 30 to 75 mole % ethylene glycol residues; 30 to 70 mole % 1,4-cyclohexanedimethanol residues and 30 to 70 mole % ethylene glycol residues; 35 to 70 mole % 1,4-cyclohexanedimethanol residues and 30 to 65 mole % ethylene glycol residues; 40 to 70 mole % 1,4-cyclohexanedimethanol residues and 30 to 60 mole % ethylene glycol residues; 45 to 70 mole % 1,4-cyclohexanedimethanol residues and 30 to 55 mole % ethylene glycol residues; 50 to 70 mole % 1,4-cyclohexanedimethanol residues and 30 to 50 mole % ethylene glycol residues; 55 to 70 mole % 1,4-cyclohexanedimethanol residues and 30 to 45 mole % ethylene glycol residues; 60 to 70 mole % 1,4-cyclohexanedimethanol residues and 30 to 40 mole % ethylene glycol residues; and 65 to 70 mole % 1,4-cyclohexanedimethanol residues and 30 to 35 mole % ethylene glycol residues.

In other aspects of the invention, the glycol component for the polyesters useful in the invention include but are not limited to at least one of the following ranges: 0.01 to 65 mole % 1,4-cyclohexanedimethanol residues and 35 to 99.99 mole % ethylene glycol residues; 1 to 65 mole % 1,4-cyclohexanedimethanol residues and 35 to 99 mole % ethylene glycol residues; 5 to 65 mole % 1,4-cyclohexanedimethanol residues and 35 to 95 mole % ethylene glycol residues; 10 to 65 mole % 1,4-cyclohexanedimethanol residues and 35 to 90 mole % ethylene glycol residues; 15 to 65 mole % 1,4-cyclohexanedimethanol residues and 35 to 85 mole % ethylene glycol residues; 20 to 65 mole % 1,4-cyclohexanedimethanol residues and 35 to 80 mole % ethylene glycol residues, 25 to 65 mole % 1,4-cyclohexanedimethanol residues and 35 to 75 mole % ethylene glycol residues; 30 to 65 mole % 1,4-cyclohexanedimethanol residues and 35 to 70 mole % ethylene glycol residues; 35 to 65 mole % 1,4-cyclohexanedimethanol residues and 35 to 65 mole % ethylene glycol residues; 40 to 65 mole % 1,4-cyclohexanedimethanol residues and 35 to 60 mole % ethylene glycol residues; 45 to 65 mole % 1,4-cyclohexanedimethanol residues and 35 to 55 mole % ethylene glycol residues; 50 to 65 mole % 1,4-cyclohexanedimethanol residues and 35 to 50 mole % ethylene glycol residues; 55 to 65 mole % 1,4-cyclohexanedimethanol residues and 35 to 45 mole % ethylene glycol residues; and 60 to 65 mole % 1,4-cyclohexanedimethanol residues and 35 to 40 mole % ethylene glycol residues.

In other aspects of the invention, the glycol component for the polyesters useful in the invention include but are not limited to at least one of the following ranges: 0.01 to 60 mole % 1,4-cyclohexanedimethanol residues and 40 to 99.99 mole % ethylene glycol residues; 1 to 60 mole % 1,4-cyclohexanedimethanol residues and 40 to 99 mole % ethylene glycol residues; 5 to 60 mole % 1,4-cyclohexanedimethanol residues and 40 to 95 mole % ethylene glycol residues; 10 to 60 mole % 1,4-cyclohexanedimethanol residues and 40 to 90 mole % ethylene glycol residues; 15 to 60 mole % 1,4-cyclohexanedimethanol residues and 40 to 85 mole % ethylene glycol residues; 20 to 60 mole % 1,4-cyclohexanedimethanol residues and 40 to 80 mole % ethylene glycol residues; 25 to 60 mole % 1,4-cyclohexanedimethanol residues and 40 to 75 mole % ethylene glycol residues; 30 to 60 mole % 1,4-cyclohexanedimethanol residues and 40 to 70 mole % ethylene glycol residues; 35 to 60 mole % 1,4-cyclohexanedimethanol residues and 40 to 65 mole % ethylene glycol residues; 40 to 60 mole % 1,4-cyclohexanedimethanol residues and 40 to 60 mole % ethylene glycol residues; 45 to 60 mole % 1,4-cyclohexanedimethanol residues and 40 to 55 mole % ethylene glycol residues; 50 to 60 mole % 1,4-cyclohexanedimethanol residues and 40 to 50 mole % ethylene glycol residues; 55 to 60 mole % 1,4-cyclohexanedimethanol residues and 40 to 45 mole % ethylene glycol residues.

In other aspects of the invention, the glycol component for the polyesters useful in the invention include but are not limited to at least one of the following ranges: 0.01 to 55 mole % 1,4-cyclohexanedimethanol residues and 45 to 99.99 mole % ethylene glycol residues; 1 to 55 mole % 1,4-cyclohexanedimethanol residues and 45 to 99 mole % ethylene glycol residues; 5 to 55 mole % 1,4-cyclohexanedimethanol residues and 45 to 95 mole % ethylene glycol residues; 10 to 55 mole % 1,4-cyclohexanedimethanol residues and 45 to 90 mole % ethylene glycol residues; 15 to 55 mole % 1,4-cyclohexanedimethanol residues and 45 to 85 mole % ethylene glycol residues; 20 to 55 mole % 1,4-cyclohexanedimethanol residues and 45 to 80 mole % ethylene glycol residues; 25 to 55 mole % 1,4-cyclohexanedimethanol residues and 45 to 75 mole % ethylene glycol residues; 30 to 55 mole % 1,4-cyclohexanedimethanol residues and 45 to 70 mole % ethylene glycol residues; 35 to 55 mole % 1,4-cyclohexanedimethanol residues and 45 to 65 mole % ethylene glycol residues; 40 to 55 mole % 1,4-cyclohexanedimethanol residues and 45 to 60 mole % ethylene glycol residues; 45 to 55 mole % 1,4-cyclohexanedimethanol residues and 45 to 55 mole % ethylene glycol residues; and 50 to 55 mole % 1,4-cyclohexanedimethanol residues and 45 to 50 mole % ethylene glycol residues.

In other aspects of the invention, the glycol component for the polyesters useful in the invention include but are not limited to at least one of the following ranges: 0.01 to 50 mole % 1,4-cyclohexanedimethanol residues and 50 to 99.99 mole % ethylene glycol residues; 1 to 50 mole % 1,4-cyclohexanedimethanol residues and 50 to 99 mole % ethylene glycol residues; 5 to 50 mole % 1,4-cyclohexanedimethanol residues and 50 to 95 mole % ethylene glycol residues; 10 to 50 mole % 1,4-cyclohexanedimethanol residues and 50 to 90 mole % ethylene glycol residues; 15 to 50 mole % 1,4-cyclohexanedimethanol residues and 50 to 85 mole % ethylene glycol residues; 20 to 50 mole % 1,4-cyclohexanedimethanol residues and 50 to 80 mole % ethylene glycol residues 25 to 50 mole % 1,4-cyclohexanedimethanol residues and 50 to 75 mole % ethylene glycol residues; 30 to 50 mole % 1,4-cyclohexanedimethanol residues and 50 to 70 mole % ethylene glycol residues; 35 to 50 mole % 1,4-cyclohexanedimethanol residues and 50 to 65 mole % ethylene glycol residues; 40 to 50 mole % 1,4-cyclohexanedimethanol residues and 50 to 60 mole % ethylene glycol residues; and 45 to 50 mole % 1,4-cyclohexanedimethanol residues and 50 to 55 mole % ethylene glycol residues.

In other aspects of the invention, the glycol component for the polyesters useful in the invention include but are not limited to at least one of the following ranges: 0.01 to 45 mole % 1,4-cyclohexanedimethanol residues and 55 to 99.99 mole % ethylene glycol residues; 1 to 45 mole % 1,4-cyclohexanedimethanol residues and 55 to 99 mole % ethylene glycol residues; 5 to 45 mole % 1,4-cyclohexanedimethanol residues and 50 to 95 mole % ethylene glycol residues; 10 to 45 and 55 to 95 mole % ethylene glycol residues mole % 1,4-cyclohexanedimethanol residues; 15 to 45 mole % 1,4-cyclohexanedimethanol residues and 55 to 85 mole % ethylene glycol residues; 20 to 45 mole % 1,4-cyclohexanedimethanol residues and 55 to 80 mole % ethylene glycol residues; 25 to 45 mole % 1,4-cyclohexanedimethanol residues and 55 to 75 mole % ethylene glycol residues; 30 to 45 mole % 1,4-cyclohexanedimethanol residues and 55 to 65 mole % ethylene glycol residues; 35 to 45 mole % 1,4-cyclohexanedimethanol residues and 55 to 65 mole % ethylene glycol residues; 40 to 45 mole % 1,4-cyclohexanedimethanol residues and 55 to 60 mole % ethylene glycol residues.

In other aspects of the invention, the glycol component for the polyesters useful in the invention include but are not limited to at least one of the following ranges: 0.01 to 40 mole % 1,4-cyclohexanedimethanol residues and 60 to 99.99 mole % ethylene glycol residues; 1 to 40 mole % 1,4-cyclohexanedimethanol residues and 60 to 99 mole % ethylene glycol residues; 5 to 40 mole % 1,4-cyclohexanedimethanol residues and 60 to 95 mole % ethylene glycol residues; 10 to 40 mole % 1,4-cyclohexanedimethanol residues and 60 to 90 mole % ethylene glycol residues; 15 to 40 mole % 1,4-cyclohexanedimethanol residues and 60 to 85 mole % ethylene glycol residues; 20 to 40 mole % 1,4-cyclohexanedimethanol residues and 60 to 80 mole % ethylene glycol residues; 25 to 40 mole % 1,4-cyclohexanedimethanol residues and 60 to 75 mole % ethylene glycol residues; 30 to 40 mole % 1,4-cyclohexanedimethanol residues and 60 to 70 mole % ethylene glycol residues; 35 to 40 mole % 1,4-cyclohexanedimethanol residues and 60 to 65 mole % ethylene glycol residues.

In other aspects of the invention, the glycol component for the polyesters useful in the invention include but are not limited to at least one of the following ranges: 0.01 to 35 mole % 1,4-cyclohexanedimethanol residues and 65 to 99.99 mole % ethylene glycol residues; 1 to 35 mole % 1,4-cyclohexanedimethanol residues and 65 to 99 mole % ethylene glycol residues; 5 to 35 mole % 1,4-cyclohexanedimethanol residues and 65 to 95 mole % ethylene glycol residues; 10 to 35 mole % 1,4-cyclohexanedimethanol residues and 65 to 90 mole % ethylene glycol residues; 15 to 35 mole % 1,4-cyclohexanedimethanol residues and 65 to 85 mole % ethylene glycol residues; 20 to 35 mole % 1,4-cyclohexanedimethanol residues and 65 to 80 mole % ethylene glycol residues; 25 to 35 mole % 1,4-cyclohexanedimethanol residues and 65 to 75 mole % ethylene glycol residues; 30 to 35 mole % 1,4-cyclohexanedimethanol residues and 65 to 70 mole % ethylene glycol residues.

In other aspects of the invention, the glycol component for the polyesters useful in the invention include but are not limited to at least one of the following ranges: 0.01 to 30 mole % 1,4-cyclohexanedimethanol residues and 70 to 99.99 mole % mole % ethylene glycol residues; 1 to 30 mole % 1,4-cyclohexanedimethanol residues and 70 to 99 mole % ethylene glycol residues; 5 to 30 mole % 1,4-cyclohexanedimethanol residues and 70 to 95 mole % ethylene glycol residues; 10 to 30 mole % 1,4-cyclohexanedimethanol residues and 70 to 90 mole % ethylene glycol residues; 15 to 30 mole % 1,4-cyclohexanedimethanol residues and 70 to 85 mole % ethylene glycol residues; 20 to 30 mole % 1,4-cyclohexanedimethanol residues and 70 to 80 mole % ethylene glycol residues; 25 to 30 mole % 1,4-cyclohexanedimethanol residues and 70 to 75 mole % ethylene glycol residues.

In other aspects of the invention, the glycol component for the polyesters useful in the invention include but are not limited to at least one of the following ranges: 0.01 to 25 mole % 1,4-cyclohexanedimethanol residues and 75 to 99.99 mole % ethylene glycol residues; 1 to 25 mole % 1,4-cyclohexanedimethanol residues and 75 to 99 mole % ethylene glycol residues; 5 to 25 mole % 1,4-cyclohexanedimethanol residues and 75 to 95 mole % ethylene glycol residues; 10 to 25 mole % 1,4-cyclohexanedimethanol residues and 75 to 90 mole % ethylene glycol residues; 15 to 25 mole % 1,4-cyclohexanedimethanol residues and 75 to 85 mole % ethylene glycol residues; 20 to 25 mole % 1,4-cyclohexanedimethanol residues and 75 to 80 mole % ethylene glycol residues.

In other aspects of the invention, the glycol component for the polyesters useful in the invention include but are not limited to at least one of the following ranges: 0.01 to 20 mole % 1,4-cyclohexanedimethanol residues and 80 to 99.99 mole % ethylene glycol residues; 1 to 20 mole % 1,4-cyclohexanedimethanol residues and 80 to 99 mole % ethylene glycol residues; 5 to 20 mole % 1,4-cyclohexanedimethanol residues and 80 to 95 mole % ethylene glycol residues; 10 to 20 mole % 1,4-cyclohexanedimethanol residues and 80 to 90 mole % ethylene glycol residues; and 15 to 20 mole % 1,4-cyclohexanedimethanol residues and 80 to 85 mole % ethylene glycol residues.

In other aspects of the invention, the glycol component for the polyesters useful in the invention include but are not limited to at least one of the following ranges: 0.01 to 15 mole % 1,4-cyclohexanedimethanol residues and 85 to 99.99 mole % ethylene glycol residues; 1 to 15 mole %

1,4-cyclohexanedimethanol residues and 85 to 99 mole % ethylene glycol residues; 5 to 15 mole % 1,4-cyclohexanedimethanol residues and 85 to 95 mole % ethylene glycol residues; and 10 to 15 mole % 1,4-cyclohexanedimethanol residues and 85 to 90 mole % ethylene glycol residues.

In other aspects of the invention, the glycol component for the polyesters useful in the invention include but are not limited to at least one of the following ranges: 0.01 to 10 mole % 1,4-cyclohexanedimethanol residues and 90 to 99.99 mole % ethylene glycol residues; 1 to 10 mole % 1,4-cyclohexanedimethanol residues and 90 to 99 mole % ethylene glycol residues; 5 to 10 mole % 1,4-cyclohexanedimethanol residues and 90 to 95 mole % ethylene glycol residues; 0.01 to 5 mole % 1,4-cyclohexanedimethanol residues and 95 to 99.99 mole % ethylene glycol residues and 1 to 5 mole % 1,4-cyclohexanedimethanol residues and 95 to 99 mole % ethylene glycol residues.

In other aspects of the invention, the glycol component for the polyesters useful in the invention include but are not limited to at least one of the following combinations of ranges: 10 to 99 mole % 2,2,4,4-tetramethyl-1,3-cyclobutanediol residues and 1 to 90 mole % 1,4-cyclohexanedimethanol residues; 10 to 95 mole % 2,2,4,4-tetramethyl-1,3-cyclobutanediol residues and 5 to 90 mole % 1,4-cyclohexanedimethanol residues; 10 to 90 mole % 2,2,4,4-tetramethyl-1,3-cyclobutanediol residues and 10 to 90 mole % 1,4-cyclohexanedimethanol residues; 10 to 85 mole % 2,2,4,4-tetramethyl-1,3-cyclobutanediol residues and 15 to 90 mole % 1,4-cyclohexanedimethanol residues; 10 to 80 mole % 2,2,4,4-tetramethyl-1,3-cyclobutanediol residues and 20 to 90 mole % 1,4-cyclohexanedimethanol residues, 10 to 75 mole % 2,2,4,4-tetramethyl-1,3-cyclobutanediol residues and 25 to 90 mole % 1,4-cyclohexanedimethanol residues; 10 to 70 mole % 2,2,4,4-tetramethyl-1,3-cyclobutanediol residues and 30 to 90 mole % 1,4-cyclohexanedimethanol residues; 10 to 65 mole % 2,2,4,4-tetramethyl-1,3-cyclobutanediol residues and 35 to 90 mole % 1,4-cyclohexanedimethanol residues; 10 to 60 mole % 2,2,4,4-tetramethyl-1,3-cyclobutanediol residues and 40 to 90 mole % 1,4-cyclohexanedimethanol residues; 10 to 55 mole % 2,2,4,4-tetramethyl-1,3-cyclobutanediol residues and 45 to 90 mole % 1,4-cyclohexanedimethanol residues; 10 to 50 mole % 2,2,4,4-tetramethyl-1,3-cyclobutanediol residues and 50 to 90 mole % 1,4-cyclohexanedimethanol residues; 10 to less than 50 mole % 2,2,4,4-tetramethyl-1,3-cyclobutanediol residues and greater than 50 to 90 mole % 1,4-cyclohexanedimethanol residues; 10 to 45 mole % 2,2,4,4-tetramethyl-1,3-cyclobutanediol residues and 55 to 90 mole % 1,4-cyclohexanedimethanol residues; 10 to 40 mole % 2,2,4,4-tetramethyl-1,3-cyclobutanediol residues and 60 to 90 mole % 1,4-cyclohexanedimethanol residues; 10 to 35 mole % 2,2,4,4-tetramethyl-1,3-cyclobutanediol residues and 65 to 90 mole % 1,4-cyclohexanedimethanol residues; 10 to less than 35 mole % 2,2,4,4-tetramethyl-1,3-cyclobutanediol residues and greater than 65 up to 90 mole % 1,4-cyclohexanedimethanol residues; 10 to 30 mole % 2,2,4,4-tetramethyl-1,3-cyclobutanediol residues and 70 to 90 mole % 1,4-cyclohexanedimethanol residues; 10 to 25 mole % 2,2,4,4-tetramethyl-1,3-cyclobutanediol residues and greater than 75 to 90 mole % 1,4-cyclohexanedimethanol residues; 11 to 25 mole % 2,2,4,4-tetramethyl-1,3-cyclobutanediol residues and 75 to 89 mole % 1,4-cyclohexanedimethanol residues; 12 to 25 mole % 2,2,4,4-tetramethyl-1,3-cyclobutanediol residues and 75 to 88 mole % 1,4-cyclohexanedimethanol residues; and 13 to 25 mole % 2,2,4,4-tetramethyl-1,3-cyclobutanediol residues and 75 to 87 mole % 1,4-cyclohexanedimethanol residues;

In other aspects of the invention, the glycol component for the polyesters useful in the invention include but are not limited to at least one of the following combinations of ranges: 15 to 99 mole % 2,2,4,4-tetramethyl-1,3-cyclobutanediol residues and 1 to 85 mole % 1,4-cyclohexanedimethanol residues; 15 to 95 mole % 2,2,4,4-tetramethyl-1,3-cyclobutanediol residues and 5 to 85 mole % 1,4-cyclohexanedimethanol residues; 15 to 90 mole % 2,2,4,4-tetramethyl-1,3-cyclobutanediol residues and 10 to 85 mole % 1,4-cyclohexanedimethanol residues; 15 to 85 mole % 2,2,4,4-tetramethyl-1,3-cyclobutanediol residues and 15 to 85 mole % 1,4-cyclohexanedimethanol residues; 15 to 80 mole % 2,2,4,4-tetramethyl-1,3-cyclobutanediol residues and 20 to 85 mole % 1,4-cyclohexanedimethanol residues, 15 to 75 mole % 2,2,4,4-tetramethyl-1,3-cyclobutanediol residues and 25 to 85 mole % 1,4-cyclohexanedimethanol residues; 15 to 70 mole % 2,2,4,4-tetramethyl-1,3-cyclobutanediol residues and 30 to 85 mole % 1,4-cyclohexanedimethanol residues; 15 to 65 mole % 2,2,4,4-tetramethyl-1,3-cyclobutanediol residues and 35 to 85 mole % 1,4-cyclohexanedimethanol residues; 15 to 60 mole % 2,2,4,4-tetramethyl-1,3-cyclobutanediol residues and 40 to 85 mole % 1,4-cyclohexanedimethanol residues; 15 to 55 mole % 2,2,4,4-tetramethyl-1,3-cyclobutanediol residues and 45 to 85 mole % 1,4-cyclohexanedimethanol residues; and 15 to 50 mole % 2,2,4,4-tetramethyl-1,3-cyclobutanediol residues and 50 to 85 mole % 1,4-cyclohexanedimethanol residues.

In other aspects of the invention, the glycol component for the polyesters useful in the invention include but are not limited to at least one of the following combinations of ranges: 15 to less than 50 mole % 2,2,4,4-tetramethyl-1,3-cyclobutanediol residues and greater than 50 up to 85 mole % 1,4-cyclohexanedimethanol residues; 15 to 45 mole % 2,2,4,4-tetramethyl-1,3-cyclobutanediol residues and 55 to 85 mole % 1,4-cyclohexanedimethanol residues; 15 to 40 mole % 2,2,4,4-tetramethyl-1,3-cyclobutanediol residues and 60 to 85 mole % 1,4-cyclohexanedimethanol residues; 15 to 35 mole % 2,2,4,4-tetramethyl-1,3-cyclobutanediol residues and 65 to 85 mole % 1,4-cyclohexanedimethanol residues; 15 to 30 mole % 2,2,4,4-tetramethyl-1,3-cyclobutanediol residues and 70 to 85 mole % 1,4-cyclohexanedimethanol residues; 15 to 25 mole % 2,2,4,4-tetramethyl-1, 3-cyclobutanediol residues and 75 to 85 mole % 1,4-cyclohexanedimethanol residues; 15 to 20 mole % 2,2,4,4-tetramethyl-1,3-cyclobutanediol residues and 75 to 80 mole % 1,4-cyclohexanedimethanol residues; and 17 to 23 mole % 2,2,4,4-tetramethyl-1,3-cyclobutanediol residues and 77 to 83 mole % 1,4-cyclohexanedimethanol residues.

In other aspects of the invention, the glycol component for the polyesters useful in the invention include but are not limited to at least one of the following combinations of ranges: 20 to 99 mole % 2,2,4,4-tetramethyl-1,3-cyclobutanediol residues and 1 to 80 mole % 1,4-cyclohexanedimethanol residues; 20 to 95 mole % 2,2,4,4-tetramethyl-1, 3-cyclobutanediol residues and 5 to 80 mole % 1,4-cyclohexanedimethanol residues; 20 to 90 mole % 2,2,4,4-tetramethyl-1,3-cyclobutanediol residues and 10 to 80 mole % 1,4-cyclohexanedimethanol residues; 20 to 85 mole % 2,2,4,4-tetramethyl-1,3-cyclobutanediol residues and 15 to 80 mole % 1,4-cyclohexanedimethanol residues; 20 to 80 mole % 2,2,4,4-tetramethyl-1,3-cyclobutanediol residues and 20 to 80 mole % 1,4-cyclohexanedimethanol residues, 20 to 75 mole % 2,2,4,4-tetramethyl-1,3-cyclobutanediol residues and 25 to 80 mole % 1,4-cyclohexanedimethanol residues; 20 to 70 mole % 2,2,4,4-tetramethyl-1,3-cyclobutanediol residues and 30 to 80 mole % 1,4-cyclohexanedimethanol residues; 20 to 65 mole % 2,2,4,4-tetramethyl-1, 3-cyclobutanediol residues and 35 to 80 mole % 1,4-cyclohexanedimethanol residues; 20 to 60 mole % 2,2,4,4-tetramethyl-1,3-cyclobutanediol residues and 40 to 80 mole % 1,4-cyclohexanedimethanol residues; 20 to 55 mole % 2,2,4,4-tetramethyl-1,3-cyclobutanediol residues and 45 to 80 mole % 1,4-cyclohexanedimethanol residues; 20 to 50 mole % 2,2,4,4-tetramethyl-1,3-cyclobutanediol residues and 50 to 80 mole % 1,4-cyclohexanedimethanol residues; 20 to 45 mole % 2,2,4,4-tetramethyl-1,3-cyclobutanediol residues and 55 to 80 mole % 1,4-cyclohexanedimethanol residues; 20 to 40 mole % 2,2,4,4-tetramethyl-1,3-cyclobutanediol residues and 60 to 80 mole % 1,4-cyclohexanedimethanol residues; 20 to 35 mole % 2,2,4,4-tetramethyl-1,3-cyclobutanediol residues and 65 to 80 mole % 1,4-cyclohexanedimethanol residues; 20 to 30 mole % 2,2,4,4-tetramethyl-1,3-cyclobutanediol residues and 70 to 80 mole % 1,4-cyclohexanedimethanol residues; and 20 to 25 mole % 2,2,4,4-tetramethyl-1,3-cyclobutanediol residues and 75 to 80 mole % 1,4-cyclohexanedimethanol residues.

In other aspects of the invention, the glycol component for the polyesters useful in the invention include but are not limited to at least one of the following combinations of ranges: 25 to 99 mole % 2,2,4,4-tetramethyl-1,3-cyclobutanediol residues and 1 to 75 mole % 1,4-cyclohexanedimethanol residues; 25 to 95 mole % 2,2,4,4-tetramethyl-1,3-cyclobutanediol residues and 5 to 75 mole % 1,4-cyclohexanedimethanol residues; 25 to 90 mole % 2,2,4,4-tetramethyl-1,3-cyclobutanediol residues and 10 to 75 mole % 1,4-cyclohexanedimethanol residues; 25 to 85 mole % 2,2,4,4-tetramethyl-1,3-cyclobutanediol residues and 15 to 75 mole % 1,4-cyclohexanedimethanol residues; 25 to 80 mole % 2,2,4,4-tetramethyl-1,3-cyclobutanediol residues and 20 to 75 mole % 1,4-cyclohexanedimethanol residues, 25 to 75 mole % 2,2,4,4-tetramethyl-1,3-cyclobutanediol residues and 25 to 75 mole % 1,4-cyclohexanedimethanol residues; 25 to 70 mole % 2,2,4,4-tetramethyl-1,3-cyclobutanediol residues and 30 to 75 mole % 1,4-cyclohexanedimethanol residues; 25 to 65 mole % 2,2,4,4-tetramethyl-1,3-cyclobutanediol residues and 35 to 75 mole % 1,4-cyclohexanedimethanol residues; 25 to 60 mole % 2,2,4,4-tetramethyl-1,3-cyclobutanediol residues and 40 to 75 mole % 1,4-cyclohexanedimethanol residues; 25 to 55 mole % 2,2,4,4-tetramethyl-1,3-cyclobutanediol residues and 45 to 75 mole % 1,4-cyclohexanedimethanol residues; 25 to 50 mole % 2,2,4,4-tetramethyl-1,3-cyclobutanediol residues and 50 to 75 mole % 1,4-cyclohexanedimethanol residues; 25 to 45 mole % 2,2,4,4-tetramethyl-1,3-cyclobutanediol residues and 55 to 75 mole % 1,4-cyclohexanedimethanol residues; 25 to 40 mole % 2,2,4,4-tetramethyl-1,3-cyclobutanediol residues and 60 to 75 mole % 1,4-cyclohexanedimethanol residues; 25 to 35 mole % 2,2,4,4-tetramethyl-1,3-cyclobutanediol residues and 65 to 75 mole % 1,4-cyclohexanedimethanol residues; and 25 to 30 mole % 2,2,4,4-tetramethyl-1,3-cyclobutanediol residues and 70 to 75 mole % 1,4-cyclohexanedimethanol residues.

In other aspects of the invention, the glycol component for the polyesters useful in the invention include but are not limited to at least one of the following combinations of ranges: 30 to 99 mole % 2,2,4,4-tetramethyl-1,3-cyclobutanediol residues and 1 to 70 mole % 1,4-cyclohexanedimethanol residues; 30 to 95 mole % 2,2,4,4-tetramethyl-1,3-cyclobutanediol residues and 5 to 70 mole % 1,4-cyclohexanedimethanol residues; 30 to 90 mole % 2,2,4,4-tetramethyl-1,3-cyclobutanediol residues and 10 to 70 mole % 1,4-cyclohexanedimethanol residues; 30 to 85 mole % 2,2,4,4-tetramethyl-1,3-cyclobutanediol residues and 15 to 70 mole % 1,4-cyclohexanedimethanol residues; 30 to 80 mole % 2,2,4,4-tetramethyl-1,3-cyclobutanediol residues and 20 to 70 mole % 1,4-cyclohexanedimethanol residues, 30 to 75 mole % 2,2,4,4-tetramethyl-1,3-cyclobutanediol residues and 25 to 70 mole % 1,4-cyclohexanedimethanol residues; 30 to 70 mole % 2,2,4,4-tetramethyl-1,3-cyclobutanediol residues and 30 to 70 mole % 1,4-cyclohexanedimethanol residues; 30 to 65 mole % 2,2,4,4-tetramethyl-1,3-cyclobutanediol residues and 35 to 70 mole % 1,4-cyclohexanedimethanol residues; 30 to 60 mole % 2,2,4,4-tetramethyl-1,3-cyclobutanediol residues and 40 to 70 mole % 1,4-cyclohexanedimethanol residues; 30 to 55 mole % 2,2,4,4-tetramethyl-1,3-cyclobutanediol residues and 45 to 70 mole % 1,4-cyclohexanedimethanol residues; 30 to 50 mole % 2,2,4,4-tetramethyl-1,3-cyclobutanediol residues and 50 to 70 mole % 1,4-cyclohexanedimethanol residues; 30 to less than 50 mole % 2,2,4,4-tetramethyl-1,3-cyclobutanediol residues and greater than 50 to 70 mole % 1,4-cyclohexanedimethanol residues; 30 to 45 mole % 2,2,4,4-tetramethyl-1,3-cyclobutanediol residues and 55 to 70 mole % 1,4-cyclohexanedimethanol residues; 30 to 40 mole % 2,2,4,4-tetramethyl-1,3-cyclobutanediol residues and 60 to 70 mole % 1,4-cyclohexanedimethanol residues; 30 to 35 mole % 2,2,4,4-tetramethyl-1,3-cyclobutanediol residues and 65 to 70 mole % 1,4-cyclohexanedimethanol residues.

In other aspects of the invention, the glycol component for the polyesters useful in the of the invention include but are not limited to at least one of the following combinations of ranges: 35 to 99 mole % 2,2,4,4-tetramethyl-1,3-cyclobutanediol residues and 1 to 65 mole % 1,4-cyclohexanedimethanol residues; 35 to 95 mole % 2,2,4,4-tetramethyl-1,3-cyclobutanediol residues and 5 to 65 mole % 1,4-cyclohexanedimethanol residues; 35 to 90 mole % 2,2,4,4-tetramethyl-1,3-cyclobutanediol residues and 10 to 65 mole % 1,4-cyclohexanedimethanol residues; 35 to 85 mole % 2,2,4,4-tetramethyl-1,3-cyclobutanediol residues and 15 to 65 mole % 1,4-cyclohexanedimethanol residues; 35 to 80 mole % 2,2,4,4-tetramethyl-1,3-cyclobutanediol residues and 20 to 65 mole % 1,4-cyclohexanedimethanol residues, 35 to 75 mole % 2,2,4,4-tetramethyl-1,3-cyclobutanediol residues and 25 to 65 mole % 1,4-cyclohexanedimethanol residues; 35 to 70 mole % 2,2,4,4-tetramethyl-1,3-cyclobutanediol residues and 30 to 65 mole % 1,4-cyclohexanedimethanol residues; 35 to 65 mole % 2,2,4,4-tetramethyl-1,3-cyclobutanediol residues and 35 to 65 mole % 1,4-cyclohexanedimethanol residues; 35 to 60 mole % 2,2,4,4-tetramethyl-1,3-cyclobutanediol residues and 40 to 65 mole % 1,4-cyclohexanedimethanol residues; 35 to 55 mole % 2,2,4,4-tetramethyl-1,3-cyclobutanediol residues and 45 to 65 mole % 1,4-cyclohexanedimethanol residues; 35 to 50 mole % 2,2,4,4-tetramethyl-1,3-cyclobutanediol residues and 50 to 65 mole % 1,4-cyclohexanedimethanol residues; 35 to less than 50 mole % 2,2,4,4-tetramethyl-1,3-cyclobutanediol residues and greater than 50 to 65 mole % 1,4-cyclohexanedimethanol residues; 35 to 45 mole % 2,2,4,4-tetramethyl-1,3-cyclobutanediol residues and 55 to 65 mole % 1,4-cyclohexanedimethanol residues; 35 to 40 mole % 2,2,4,4-tetramethyl-1,3-cyclobutanediol residues and 60 to 65 mole % 1,4-cyclohexanedimethanol residues.

In other aspects of the invention, the glycol component for the polyesters useful in the invention include but are not limited to at least one of the following combinations of ranges: 40 to 99 mole % 2,2,4,4-tetramethyl-1,3-cyclobutanediol residues and 1 to 60 mole % 1,4-cyclohexanedimethanol residues; 40 to 95 mole % 2,2,4,4-tetramethyl-1,3-cyclobutanediol residues and 5 to 60 mole % 1,4-cyclohexanedimethanol residues; 40 to 90 mole % 2,2,4,4-tetramethyl-1,3-cyclobutanediol residues and 10 to 60 mole % 1,4-cyclohexanedimethanol residues; 40 to 85 mole % 2,2,4,4-tetramethyl-1,3-cyclobutanediol residues and 15 to 60 mole % 1,4-cyclohexanedimethanol residues; 40 to 80 mole % 2,2,4,4-tetramethyl-1,3-cyclobutanediol residues and 20 to 60 mole % 1,4-cyclohexanedimethanol residues, 40 to 75 mole % 2,2,4,4-tetramethyl-1,3-cyclobutanediol residues and 25 to 60 mole % 1,4-cyclohexanedimethanol residues; 40 to 70 mole % 2,2,4,4-tetramethyl-1,3-cyclobutanediol residues and 30 to 60 mole % 1,4-cyclohexanedimethanol residues; 40 to 65 mole % 2,2,4,4-tetramethyl-1,3-cyclobutanediol residues and 35 to 60 mole % 1,4-cyclohexanedimethanol residues; 40 to 60 mole % 2,2,4,4-tetramethyl-1,3-cyclobutanediol residues and 40 to 60 mole % 1,4-cyclohexanedimethanol residues; 40 to 55 mole % 2,2,4,4-tetramethyl-1,3-cyclobutanediol residues and 45 to 60 mole % 1,4-cyclohexanedimethanol residues; 40 to less than 50 mole % 2,2,4,4-tetramethyl-1,3-cyclobutanediol residues and greater than 50 to 60 mole % 1,4-cyclohexanedimethanol residues; 40 to 50 mole % 2,2,4,4-tetramethyl-1,3-cyclobutanediol residues and 50 to 60 mole % 1,4-cyclohexanedimethanol residues; and 40 to 45 mole % 2,2,4,4-tetramethyl-1,3-cyclobutanediol residues and 55 to 60 mole % 1,4-cyclohexanedimethanol residues.

In other aspects of the invention, the glycol component for the polyesters useful in the invention include but are not limited to at least one of the following combinations of ranges: 45 to 99 mole % 2,2,4,4-tetramethyl-1,3-cyclobutanediol residues and 1 to 55 mole % 1,4-cyclohexanedimethanol residues; 45 to 95 mole % 2,2,4,4-tetramethyl-1,3-cyclobutanediol residues and 5 to 55 mole % 1,4-cyclohexanedimethanol residues; 45 to 90 mole % 2,2,4,4-tetramethyl-1,3-cyclobutanediol residues and 10 to 55 mole % 1,4-cyclohexanedimethanol residues; 45 to 85 mole % 2,2,4,4-tetramethyl-1,3-cyclobutanediol residues and 15 to 55 mole % 1,4-cyclohexanedimethanol residues; 45 to 80 mole % 2,2,4,4-tetramethyl-1,3-cyclobutanediol residues and 20 to 55 mole % 1,4-cyclohexanedimethanol residues, 45 to 75 mole % 2,2,4,4-tetramethyl-1,3-cyclobutanediol residues and 25 to 55 mole % 1,4-cyclohexanedimethanol residues; 45 to 70 mole % 2,2,4,4-tetramethyl-1,3-cyclobutanediol residues and 30 to 55 mole % 1,4-cyclohexanedimethanol residues; 45 to 65 mole % 2,2,4,4-tetramethyl-1,3-cyclobutanediol residues and 35 to 55 mole % 1,4-cyclohexanedimethanol residues; 45 to 60 mole % 2,2,4,4-tetramethyl-1,3-cyclobutanediol residues and 40 to 55 mole % 1,4-cyclohexanedimethanol residues; greater than 45 to 55 mole % 2,2,4,4-tetramethyl-1,3-cyclobutanediol residues and 45 to less than 55 mole % 1,4-cyclohexanedimethanol residues; 45 to 55 mole % 2,2,4,4-tetramethyl-1,3-cyclobutanediol residues and 45 to 55 mole % 1,4-cyclohexanedimethanol residues; and 45 to 50 mole % 2,2,4,4-tetramethyl-1,3-cyclobutanediol residues and 50 to 55 mole % 1,4-cyclohexanedimethanol residues.

For certain embodiments of the invention, the polyesters useful in the invention may exhibit at least one of the following inherent viscosities as determined in 60/40 (wt/wt) phenol tetrachloroethane at a concentration of 0.5 g/100 ml at 25° C.: 0.45 to 1.2 dL/g; 0.45 to 1.1 dL/g; 0.45 to 1 dL/g; 0.45 to 0.98 dL/g; 0.45 to 0.95 dL/g; 0.45 to 0.90 dL/g; 0.45 to 0.85 dL/g; 0.45 to 0.80 dL/g; 0.45 to 0.75 dL/g; 0.45 to less than 0.75 dL/g; 0.45 to 0.72 dL/g; 0.45 to 0.70 dL/g; 0.45 to less than 0.70 dL/g; 0.45 to 0.68 dL/g; 0.45 to less than 0.68 dL/g; 0.45 to 0.65 dL/g; 0.50 to 1.2 dL/g; 0.50 to 1.1 dL/g; 0.50 to 1 dL/g; 0.50 to less than 1 dL/g; 0.50 to 0.98 dL/g; 0.50 to 0.95 dL/g; 0.50 to 0.90 dL/g; 0.50 to 0.85 dL/g; 0.50 to 0.80 dL/g; 0.50 to 0.75 dL/g; 0.50 to less than 0.75 dL/g; 0.50 to 0.72 dL/g; 0.50 to 0.70 dL/g; 0.50 to less than 0.70 dL/g; 0.50 to 0.68 dL/g; 0.50 to less than 0.68 dL/g; 0.50 to 0.65 dL/g; 0.55 to 1.2 dL/g; 0.55 to 1.1 dL/g; 0.55 to 1 dL/g; 0.55 to less than 1 dL/g; 0.55 to 0.98 dL/g; 0.55 to 0.95 dL/g; 0.55 to 0.90 dL/g; 0.55 to 0.85 dL/g; 0.55 to 0.80 dL/g; 0.55 to 0.75 dL/g; 0.55 to less than 0.75 dL/g; 0.55 to 0.72 dL/g; 0.55 to 0.70 dL/g; 0.55 to less than 0.70 dL/g; 0.55 to 0.68 dL/g; 0.55 to less than 0.68 dL/g; 0.55 to 0.65 dL/g; 0.58 to 1.2 dL/g; 0.58 to 1.1 dL/g; 0.58 to 1 dL/g; 0.58 to less than 1 dL/g; 0.58 to 0.98 dL/g; 0.58 to 0.95 dL/g; 0.58 to 0.90 dL/g; 0.58 to 0.85 dL/g; 0.58 to 0.80 dL/g; 0.58 to 0.75 dL/g; 0.58 to less than 0.75 dL/g; 0.58 to 0.72 dL/g; 0.58 to 0.70 dL/g; 0.58 to less than 0.70 dL/g; 0.58 to 0.68 dL/g; 0.58 to less than 0.68 dL/g; 0.58 to 0.65 dL/g; 0.60 to 1.2 dL/g; 0.60 to 1.1 dL/g; 0.60 to 1 dL/g; 0.60 to less than 1 dL/g; 0.60 to 0.98 dL/g; 0.60 to 0.95 dL/g; 0.60 to 0.90 dL/g; 0.60 to 0.85 dL/g; 0.60 to 0.80 dL/g; 0.60 to 0.75 dL/g; 0.60 to less than 0.75 dL/g; 0.60 to 0.72 dL/g; 0.60 to 0.70 dL/g; 0.60 to less than 0.70 dL/g; 0.60 to 0.68 dL/g; 0.60 to less than 0.68 dL/g; 0.60 to 0.65 dL/g; 0.65 to 1.2 dL/g; 0.65 to 1.1 dL/g; 0.65 to 1 dL/g; 0.65 to less than 1 dL/g; 0.65 to 0.98 dL/g; 0.65 to 0.95 dL/g; 0.65 to 0.90 dL/g; 0.65 to 0.85 dL/g; 0.65 to 0.80 dL/g; 0.65 to 0.75 dL/g; 0.65 to less than 0.75 dL/g; 0.65 to 0.72 dL/g; 0.65 to 0.70 dL/g; 0.65 to less than 0.70 dL/g; 0.68 to 1.2 dL/g; 0.68 to 1.1 dL/g; 0.68 to 1 dL/g; 0.68 to less than 1 dL/g; 0.68 to 0.98 dL/g; 0.68 to 0.95 dL/g; 0.68 to 0.90 dL/g; 0.68 to 0.85 dL/g; 0.68 to 0.80 dL/g; 0.68 to 0.75 dL/g; 0.68 to less than 0.75 dL/g; 0.68 to 0.72 dL/g; greater than 0.76 dL/g to 1.2 dL/g It is contemplated that polyesters useful in the invention can possess at least one of the inherent viscosity ranges described herein and at least one of the monomer ranges for the compositions described herein unless otherwise stated. It is also contemplated that polyesters useful in the the invention can possess at least one of the Tg ranges described herein and at least one of the monomer ranges for the compositions described herein unless otherwise stated. Further, it is contemplated that polyesters useful in the invention can possess at least one of the Tg ranges described herein, at least one of the inherent viscosity ranges described herein, and at least one of the monomer ranges for the compositions described herein unless otherwise stated.

For the desired polyester, the molar ratio of cis/trans 2,2,4,4-tetramethyl-1,3-cyclobutanediol residues can vary from the pure form of each or mixtures thereof. In certain embodiments, the molar percentages for cis and/or trans 2,2,4,4,-tetramethyl-1,3-cyclobutanediol residues are greater than 50 mole % cis and less than 50 mole % trans; or greater than 55 mole % cis and less than 45 mole % trans; or 30 to 70 mole % cis and 70 to 30% trans; or 40 to 60 mole % cis and 60 to 40 mole % trans; or 50 to 70 mole % trans and 50 to 30% cis or 50 to 70 mole % cis and 50 to 30% trans; or 60 to 70 mole % cis and 30 to 40 mole % trans; or greater than 70 mole cis and less than 30 mole % trans; wherein the total sum of the mole percentages for cis- and trans-2,2,4,4-tetramethyl-1,3-cyclobutanediol residues is equal to 100 mole %. The molar ratio of cis/trans 1,4-cyclohexandimethanol can vary within the range of 50/50 to 0/100, such as between 40/60 to 20/80.

In certain embodiments, terephthalic acid or an ester thereof, such as, for example, dimethyl terephthalate, or a mixture of terephthalic acid and an ester thereof, makes up most or all of the dicarboxylic acid component used to form the polyesters useful in the invention. In certain embodiments, terephthalic acid residues can make up a portion or all of the dicarboxylic acid component used to form the present polyester at a concentration of at least 70 mole %, such as at least 80 mole %, at least 90 mole %, at least 95 mole %, at least 99 mole %, or 100 mole %. In certain embodiments, higher amounts of terephthalic acid can be used in order to produce a higher impact strength polyester. In one embodiment, dimethyl terephthalate is part or all of the dicarboxylic acid component used to make the polyesters useful in the present invention. For the purposes of this disclosure, the terms "terephthalic acid" and "dimethyl terephthalate" are used interchangeably herein. In all embodiments, any amount of terephthalic acid may be used, for example, ranges of from 50 to 100 mole %, 55 to 100 mole %, 60 to 100 mole %, 65 to 100 mole %, 70 to 100 mole %; or 80 to 100 mole %; or 90 to 100 mole %; or 99 to 100 mole %; or 100 mole % terephthalic acid and/or dimethyl terephthalate and/or mixtures thereof may be used.

In addition to terephthalic acid, the dicarboxylic acid component of the polyester useful in the invention can comprise up to 50 mole %, up to 45 mole %, up to 40 mole %, up to 35 mole %, up to 30 mole %, up to 25 mole %, up to 20 mole %, up to 15 mole %, up to 10 mole %, up to 5 mole %, or up to 1 mole % of one or more modifying aromatic dicarboxylic acids. Yet another embodiment contains 0 mole % modifying aromatic dicarboxylic acids. Thus, if present, it is contemplated that the amount of one or more modifying aromatic dicarboxylic acids can range from any of these preceding endpoint values including, for example, from 0.01 to 50 mole %, 0.01 to 45 mole %, 0.01 to 40 mole %, 0.01 to 35 mole %, 0.01 to 30 mole %, 0.01 to 25 mole %, 0.01 to 20 mole %, 0.01 to 15 mole % from 0.01 to 10 mole %, from 0.01 to 5 mole % and from 0.01 to 1 mole. In one embodiment, modifying aromatic dicarboxylic acids that may be used in the present invention include but are not limited to those having up to 20 carbon atoms, and which can be linear, para-oriented, or symmetrical. Examples of modifying aromatic dicarboxylic acids which may be used in this invention include, but are not limited to, isophthalic acid, 4,4'-biphenyldicarboxylic acid, 1,4-, 1,5-, 2,6-, 2,7-naphthalenedicarboxylic acid, and trans-4,4'-stilbenedicarboxylic acid, and esters thereof. In one embodiment, the modifying aromatic dicarboxylic acid is isophthalic acid.

The carboxylic acid component of the polyesters useful in the invention can be further modified with up to 10 mole %, such as up to 5 mole % or up to 1 mole % of one or more aliphatic dicarboxylic acids containing 2-16 carbon atoms, such as, for example, malonic, succinic, glutaric, adipic, pimelic, suberic, azelaic and dodecanedioic dicarboxylic acids. Certain embodiments can also comprise 0.01 or more mole %, such as 0.1 or more mole %, 1 or more mole %, 5 or more mole %, or 10 or more mole % of one or more modifying aliphatic dicarboxylic acids. Yet another embodiment contains 0 mole % modifying aliphatic dicarboxylic acids. Thus, if present, it is contemplated that the amount of one or more modifying aliphatic dicarboxylic acids can range from any of these preceding endpoint values including, for example, from 0.01 to 10 mole % and from 0.1 to 10 mole %. The total mole % of the dicarboxylic acid component is 100 mole %.

Esters of terephthalic acid and the other modifying dicarboxylic acids or their corresponding esters and/or salts may be used instead of the dicarboxylic acids. Suitable examples of dicarboxylic acid esters include, but are not limited to, the dimethyl, diethyl, dipropyl, diisopropyl, dibutyl, and diphenyl esters. In one embodiment, the esters are chosen from at least one of the following: methyl, ethyl, propyl, isopropyl, and phenyl esters.

The 1,4-cyclohexanedimethanol residues may be cis, trans, or a mixture thereof, for example a cis/trans ratio of 60:40 to 40:60. In another embodiment, the trans-1,4-cyclohexanedimethanol residues can be present in an amount of 60 to 80 mole %.

In one embodiment, the glycol component of the polyester portion of the polyester composition useful in the invention can contain 25 mole % or less of one or more modifying glycols which are not 2,2,4,4-tetramethyl-1,3-cyclobutanediol residues or 1,4-cyclohexanedimethanol residues; in one embodiment, the polyesters useful in the invention may contain less than 15 mole % of one or more modifying glycols. In another embodiment, the polyesters useful in the invention can contain 10 mole % or less of one or more modifying glycols. In another embodiment, the polyesters useful in the invention can contain 5 mole % or less of one or more modifying glycols. In another embodiment, the polyesters useful in the invention can contain 3 mole % or less of one or more modifying glycols. In another embodiment, the polyesters useful in the invention can contain 0 mole % modifying glycols. Certain embodiments can also contain 0.01 or more mole %, such as 0.1 or more mole %, 1 or more mole %, 5 or more mole %, or 10 or more mole % of one or more modifying glycols. Thus, if present, it is contemplated that the amount of one or more modifying glycols can range from any of these preceding endpoint values including, for example, from 0.01 to 15 mole % and from 0.1 to 10 mole %.

Modifying glycols useful in the polyesters useful in the invention refer to diols other than ones described in the polyesters useful in the invention herein as a required glycol and may contain 2 to 16 carbon atoms. Examples of suitable modifying glycols include, but are not limited to, ethylene glycol residues, 1,2-propanediol, 1,3-propanediol, neopentyl glycol, 2,2,4,4-tetramethyl-1,3-cyclobutanediol, ethylene glycol, 1,4-butanediol, 1,5-pentanediol, 1,6-hexanediol, p-xylene glycol or mixtures thereof. In one embodiment, the modifying glycol is ethylene glycol. In another embodiment, ethylene glycol is excluded as a modifying diol. In one embodiment, the modifying glycol is 2,2,4,4-tetramethyl-1,3-cyclobutanediol. In another embodiment, the modifying glycols are 1,3-propanediol and/or 1,4-butanediol.

The polyesters useful in the polyesters compositions of the invention can comprise from 0 to 10 mole percent, for example, from 0.01 to 5 mole percent, from 0.01 to 1 mole percent, from 0.05 to 5 mole percent, from 0.05 to 1 mole percent, or from 0.1 to 0.7 mole percent, based the total mole percentages of either the diol or diacid residues; respectively, of one or more residues of a branching monomer, also referred to herein as a branching agent, having 3 or more carboxyl substituents, hydroxyl substituents, or a combination thereof. In certain embodiments, the branching monomer or agent may be added prior to and/or during and/or after the polymerization of the polyester. The polyester(s) useful in the invention can thus be linear or branched. The polycarbonate can also be linear or branched. In certain embodiments, the branching monomer or agent may be added prior to and/or during and/or after the polymerization of the polycarbonate.

Examples of branching monomers include, but are not limited to, multifunctional acids or multifunctional alcohols such as trimellitic acid, trimellitic anhydride, pyromellitic dianhydride, trimethylolpropane, glycerol, pentaerythritol, citric acid, tartaric acid, 3-hydroxyglutaric acid and the like. In one embodiment, the branching monomer residues can comprise 0.1 to 0.7 mole percent of one or more residues chosen from at least one of the following: trimellitic anhydride, pyromellitic dianhydride, glycerol, sorbitol, 1,2,6-hexanetriol, pentaerythritol, trimethylolethane, and/or trimesic acid. The branching monomer may be added to the polyester reaction mixture or blended with the polyester in the form of a concentrate as described, for example, in U.S. Pat. Nos. 5,654,347 and 5,696,176, whose disclosure regarding branching monomers is incorporated herein by reference.

The glass transition temperature (Tg) of the polyesters useful in the invention was determined using a TA DSC 2920 from Thermal Analyst Instrument at a scan rate of 20° C./min.

In one embodiment, certain polyesters useful in this invention are visually clear. The term "visually clear" is defined herein as an appreciable absence of cloudiness, haziness, and/or muddiness, when inspected visually.

In one embodiment, polyesters of this invention exhibit superior notched toughness in thick sections. Notched Izod impact strength, as described in ASTM D256, is a common method of measuring toughness.

The polyesters useful in the invention can possess one or more of the following properties. In one embodiment, the polyesters useful in the invention exhibit a notched Izod impact strength of at least 150 J/m (3 ft-lb/in) at 23° C. with a 10-mil notch in a 3.2 mm (⅛-inch) thick bar determined according to ASTM D256; in one embodiment, the polyesters useful in the invention exhibit a notched Izod impact strength of at least (400 J/m) 7.5 ft-lb/in at 23° C. with a 10-mil notch in a 3.2 mm (⅛-inch) thick bar determined according to ASTM D256; in one embodiment, the polyesters useful in the invention exhibit a notched Izod impact strength of at least (10 ft-lb/in) at 23° C. with a 10-mil notch in a 3.2 mm (⅛-inch) thick bar determined according to ASTM D256. In one embodiment, the polyesters useful in the invention exhibit a notched Izod impact strength of at least 1000 J/m (18 ft-lb/in) at 23° C. with a 10-mil notch in a 3.2 mm (⅛-inch) thick bar determined according to ASTM D256. In one embodiment, the polyesters useful in the invention exhibit a notched Izod impact strength of at least 150 J/m (3 ft-lb/in) at 23° C. with a 10-mil notch in a 6.4 mm (¼-inch) thick bar determined according to ASTM D256; in one embodiment, the polyesters useful in the invention exhibit a notched Izod impact strength of at least (400 J/m) 7.5 ft-lb/in at 23° C. with a 10-mil notch in a 6.4 mm (¼-inch) thick bar determined according to ASTM D256; in one embodiment, the polyesters useful in the invention exhibit a notched Izod impact strength of at least 1000 J/m (18 ft-lb/in) at 23° C. with a 10-mil notch in a 6.4 mm (¼-inch) thick bar determined according to ASTM D256.

In one embodiment, the polyesters useful in the invention and/or the polyester compositions of the invention in combination with the fluoroalkyl derivatives useful in the invention, with or without toners, can have color values L*, a* and b*, which can be determined using a Hunter Lab Ultrascan Spectra Colorimeter manufactured by Hunter Associates Lab Inc., Reston, Va. The color determinations are averages of values measured on either pellets of the polyesters or plaques or other items injection molded or extruded from them. They are determined by the L*a*b* color system of the CIE (International Commission on Illumination) (translated), wherein L* represents the lightness coordinate, a* represents the red/green coordinate, and b* represents the yellow/blue coordinate. In certain embodiments, the b* values for the polyesters useful in the invention can be from −10 to less than 10 and the L* values can be from 50 to 90. In other embodiments, the b* values for the polyesters useful in the invention can be present in one of the following ranges: −10 to 9; −10 to 8; −10 to 7; −10 to 6; −10 to 5; −10 to 4; −10 to 3; −10 to 2; from −5 to 9; −5 to 8; −5 to 7; −5 to 6; −5 to 5; −5 to 4; −5 to 3; −5 to 2; 0 to 9; 0 to 8; 0 to 7; 0 to 6; 0 to 5; 0 to 4; 0 to 3; 0 to 2; 1 to 10; 1 to 9; 1 to 8; 1 to 7; 1 to 6; 1 to 5; 1 to 4; 1 to 3; and 1 to 2. In other embodiments, the L* value for the polyesters useful in the invention can be present in one of the following ranges: 50 to 60; 50 to 70; 50 to 80; 50 to 90; 60 to 70; 60 to 80; 60 to 90; 70 to 80; 79 to 90.

Reduced Fibrinogen Adsorption

Medical devices that come into contact with blood often require plastics which are designed or engineered to reduce or minimize thrombosis or blood clotting properties. Other than the blood itself and the flow rate, the device material is one of the most important variables affecting blood coagulation. Fibrinogen is the principal protein in vertebrates that is involved in the formation of blood clots.

It is well known that a material's surface properties can affect the initial events of blood protein adsorption and platelet adhesion. When most foreign surfaces are exposed to blood, proteins from the blood adsorb onto them almost immediately, depending on the materials' surface properties. Due to the complexity of blood compatibility, it is difficult to correlate surface properties directly with blood response in order to predict device performance. However, the amount of adsorbed plasma proteins, such as fibrinogen, on a material's surface is very meaningful for regulating platelet adhesion, migration of cellular components, and subsequent blood clotting. The measurement of protein adsorption can predict levels of platelet adhesion, and thus provide valuable information to evaluate regional thrombus formation.

To evaluate the blood-clotting properties of plastics, an enzyme-linked immunosorbent assay (ELISA) has been developed to detect the presence of fibrinogen adsorbed on a sample. Generally, the fibrinogen ELISA procedure involves attaching the protein to the surface of the sample in a disposable microtiter plate, and then applying an antibody over the surface to bind to the protein. The degree of antibody binding is determined by activity of the enzyme that is conjugated to the antibody. Detection of that activity is typically through the use of a chromogenic substrate for the enzyme. The extent of color change is proportional to the amount of adsorbed protein present and is typically measured spectrophotometrically using a plate reader.

In one embodiment, the fibrinogen ELISA procedure/protocol includes the following steps: (1) incubating the polymer sample in flexural bar form in a phosphate-buffered saline solution containing 0.5 mg/mL of fibrinogen and 2% of bovine serum albumin (w/v) for 5 minutes; (2) removing unbound fibrinogen from the sample bar by washing the bar with phosphate-buffered saline having a pH of 7.3 three times; (3) incubating the sample bar in a non-animal protein blocking agent for 30 minutes at 37° C.; (4) incubating the bar in a 1 µg/mL solution of an anti-fibrinogen horseradish peroxidase antibody-conjugate in a non-animal protein-blocked microtiter plate for 60 minutes at 37° C.; (5) washing the bar four times with a diluted TBST buffer to remove excess non-specific binding of the antibody-conjugate; (6) incubating the bar with an enzyme substrate 3,3',5,5'-tetramethylbenzidine for 60 minutes; (7) removing the bar from the microplate containing the enzyme substrate; and (8) measuring the absorbance of the enzyme substrate in the microplate well using a microplate spectrophotometer at 630 nanometers to detect conversion of the enzyme substrate to the blue product.

In one embodiment, the fibrinogen ELISA procedure/protocol includes the following steps: (1) incubating the polymer sample in flexural bar form in a phosphate-buffered saline solution containing 0.5 mg/mL of fibrinogen and 2% of bovine serum albumin (w/v) for 5 minutes; (2) removing unbound fibrinogen from the sample bar by washing the bar with phosphate-buffered saline (PBS) three times; (3) incubating the sample bar in a non-animal protein blocking agent (NAP-Blocker™) for 30 minutes at 37° C. to block unoccupied binding sites on the bar; (4) incubating the bar in a 1 μg/mL solution of an anti-fibrinogen horseradish peroxidase (HRP) antibody-conjugate in a NAP-blocked microtiter plate for 60 minutes at 37° C.; (5) washing the bar in a diluted TBST buffer (mixture of Tris-Buffered Saline and Tween® 20) (pH=7.5) four times to remove excess non-specific binding of the antibody-conjugate; (6) incubating the bar with an enzyme substrate (3,3',5,5'-tetramethylbenzidine) for 60 minutes; (7) removing the bar from the microplate containing the enzyme substrate; and (8) measuring the absorbance of the enzyme substrate in the microplate well using a microplate spectrophotometer at 630 nm to detect conversion of the enzyme substrate to the blue product.

The PBS is a 0.01 M phosphate-buffered solution containing 0.0027 M of potassium chloride and 0.137 M of sodium chloride with a pH of 7.4 at 25° C.

As used herein, "TBST buffer" refers to a mixture of 90.11 wt % of deionized water, 8.77 wt % of sodium chloride, 1.12 wt % of Tris, and 0.002 wt % of Tween® 20 (which is polysorbate 20). "Diluted TBST buffer" refers to TBST buffer that has been diluted 10 times (10×) with deionized water.

Preferably, the compositions according to the invention adsorb at least 5% less fibrinogen than the polyester alone (i.e., without the fluoroalkyl additive) according to the fibrinogen ELISA protocol. In certain embodiments, the compositions according to the invention adsorb at least 10% less, at least 15% less, at least 20% less, at least 25% less, at least 30% less, at least 35% less, at least 40% less, or at least 45% less fibrinogen than the polyester alone according to the fibrinogen ELISA protocol. In other embodiments, the compositions according to the invention adsorb 5 to 50% less fibrinogen, 10 to 50% less fibrinogen, 15 to 50% less fibrinogen, 20 to 50% less fibrinogen, 25 to 50% less fibrinogen, 30 to 50% less fibrinogen, 35 to 50% less fibrinogen, or 40 to 50% less fibrinogen than the polyester alone according to the fibrinogen ELISA protocol. In yet other embodiments, the compositions according to the invention adsorb 5 to 45% less fibrinogen, 10 to 45% less fibrinogen, 15 to 45% less fibrinogen, 20 to 45% less fibrinogen, 25 to 45% less fibrinogen, 30 to 45% less fibrinogen, 35 to 45% less fibrinogen, or 40 to 45% less fibrinogen than the polyester alone according to the fibrinogen ELISA protocol. In yet other embodiments, the compositions according to the invention adsorb 5 to 40% less fibrinogen, 10 to 40% less fibrinogen, 15 to 40% less fibrinogen, 20 to 40% less fibrinogen, 25 to 40% less fibrinogen, 30 to 40% less fibrinogen, or 35 to 40% less fibrinogen than the polyester alone according to the fibrinogen ELISA protocol. In yet other embodiments, the compositions according to the invention adsorb 5 to 35% less fibrinogen, 10 to 35% less fibrinogen, 15 to 35% less fibrinogen, 20 to 35% less fibrinogen, 25 to 35% less fibrinogen, or 30 to 35% less fibrinogen than the polyester alone according to the fibrinogen ELISA protocol. In yet other embodiments, the compositions according to the invention adsorb 5 to 30% less fibrinogen, 10 to 30% less fibrinogen, 15 to 30% less fibrinogen, 20 to 30% less fibrinogen, or 25 to 30% less fibrinogen than the polyester alone according to the fibrinogen ELISA protocol.

In certain embodiments, the compositions according to the invention have a coefficient of friction (COF) of less than 0.50, of less than 0.40, of less than 0.35, of less than 0.30, of less than 0.25, of less than 0.24, of less than 0.23, of less than 0.22, of less than 0.21, of less than 0.20, of less than 0.19, of less than 0.18, or of less than 0.17. In other embodiments, the compositions according to the invention have a COF of 0.15 to 0.50, 0.16 to 0.50, 0.17 to 0.50, 0.18 to 0.50, 0.19 to 0.50, 0.20 to 0.50, 0.21 to 0.50, 0.22 to 0.50, 0.23 to 0.50, 0.24 to 0.50, 0.25 to 0.50, or 0.30 to 0.50. In yet other embodiments, the compositions according to the invention have a COF of 0.15 to 0.40, 0.16 to 0.40, 0.17 to 0.40, 0.18 to 0.40, 0.19 to 0.40, 0.20 to 0.40, 0.21 to 0.40, 0.22 to 0.40, 0.23 to 0.40, 0.24 to 0.40, 0.25 to 0.40, or 0.30 to 0.40. In yet other embodiments, the compositions according to the invention have a COF of 0.15 to 0.35, 0.16 to 0.35, 0.17 to 0.35, 0.18 to 0.35, 0.19 to 0.35, 0.20 to 0.35, 0.21 to 0.35, 0.22 to 0.35, 0.23 to 0.35, 0.24 to 0.35, 0.25 to 0.35, or 0.30 to 0.35.

The COF may be measured with a Bruker™ tribometer using a 1"×1"×0.125" plaque on a 4"×4"×0.125" plaque under a 3 N normal load at 1.2 mm/second.

In one embodiment, the polyesters useful in the invention exhibit a ductile-to-brittle transition temperature of less than 0° C. based on a 10-mil notch in a ⅛-inch thick bar as defined by ASTM D256.

In one embodiment, the articles of manufacture of the invention can be any device known in the art in which one or more of the physical characteristics of any of the polyester compositions of the invention described herein are useful including but not limited to devices, containers, bottles, film and/or sheet, etc.

In one embodiment, any of these articles of manufacture can be used for the medical industry, health care industry, pharmaceutical industry, food industry, bioprocessing industry, or any other industry in which the properties of the polymer compositions of the invention can be useful.

Specific potential articles of manufacture and/or packaging can include, for example, medical packaging and/or articles and/or devices, pharmaceutical packaging and/or articles and/or devices, other health care packaging and/or articles and/or devices, packaging and/or articles and/or devices for bioprocessing, food packaging and/or articles and/or devices made therefrom, for example, medical devices for such as thermoformed trays, sterile or non-sterile packaging, steam sterilization bags or pouches, blood bags, tubing, catheters, blood therapy tubes, medical laboratory devices, medical or health diagnostic devices, oxygenators, glucose sensor strips. By "medical", veterinarian applications are contemplated as well applications for the benefit of humans.

The medical devices can include but are not limited to components for infusion and intravenous systems, extracorporeal oxygenators, renal dialyzers, catheters, and heart assist devices.

In one embodiment, the medical device can be an intravenous device or component.

"Intravenous component," as used herein, refers to components made from a polymeric material used for administering fluids (e.g., medicaments, nutrients) to the bloodstream of a patient (human and/or animal). In one embodiment, the intravenous component is a rigid component.

In one embodiment, two-port, three-port and four-port stopcocks are contemplated.

In one embodiment, the intravenous device or component can be a stopcock. In one embodiment, a stopcock can be an externally operated valve regulating the flow of a liquid or gas through a pipe or tube. In one embodiment, a stopcock can regulate the flow of intravenous fluids into a human being or into an animal.

Exemplary intravenous components include y-site connector assemblies, luer components, filters, stopcocks, manifolds, and valves. A y-site connector has a "Y" shape including a first arm having a first passage, a second arm having a second passage, and a third arm connected with said first and second arms and having a third passage communicating with said first and second passages. Luer components can include luer locks, connections, and valves.

In one embodiment, the medical device, for example, an intravenous component, can withstand sterilization treatments, such as high pressure steam sterilization, ethylene oxide gas sterilization, radiation sterilization, and dry-heating sterilization. In one embodiment, the medical device, for example, an intravenous component, has at least one property chosen from toughness, good optical clarity, good chemical resistance, good lubricity (the capacity to reduce friction and/or properties of a lubricant) such as having a low coefficient of friction (COF), good anti-protein binding properties, reduced fibrinogen adsorption, good heat resistance, and good hydrolytic stability.

Other medical devices are also contemplated which may come into contact with bodily fluids and/or blood components and/or any specimen of tissue, bone, organ, cartilage, etc. that can be removed from the human body. For certain of these medical devices, compatibility with blood and/or other bodily fluids and/or other biological material is an important characteristic.

Methods of making the articles of manufacture and/or devices of the invention include but are not limited to: injection blow molding, injection molding, compression, extrusion, extrusion blow molding, casting, etc. or any other method known to one of ordinary skill in the art Intravenous component(s) can include, for example, injection blow molded intravenous component(s), compression molded intravenous components, and injection molded intravenous component(s).

The polyester portion of the polyester compositions useful in the invention can be made by processes known from the literature such as, for example, by processes in homogenous solution, by transesterification processes in the melt, and by two phase interfacial processes. Suitable methods include, but are not limited to, the steps of reacting one or more dicarboxylic acids with one or more glycols at a temperature of 100° C. to 315° C. at a pressure of 0.1 to 760 mm Hg for a time sufficient to form a polyester. See U.S. Pat. No. 3,772,405 for methods of producing polyesters, the disclosure regarding such methods is hereby incorporated herein by reference.

The fluoroalkyl derivatives of this invention include but are not limited to ones having the general formula:

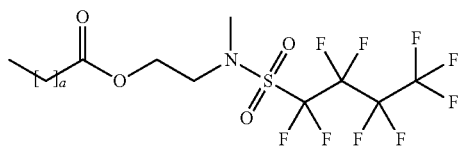

wherein n=an integer from 8 to 30.

In one embodiment of the invention, the fluoroalkyl derivative can be PM-870 additive commercially available from 3M, St. Paul, Minn. This PM-870 additive is believed to contain mixtures of the above described structure. In particular, PM-870 is believed to contain 88-90 wt % of the fluoroalkyl derivatives, 10-12 wt % of polyethylene (CAS No. 9002-88-4), <2 wt % of carboxylic acid(s), and <0.5 wt % of 1,1,2,2,3,3,4,4,4-nonafluoro-N-(2-hydroxyethyl)-N-1-methyl-1-butanesulfonamide (CAS No. 34454-97-2). Thus, in one embodiment, the fluoroalkyl derivatives useful in this invention may be mixed with polyethylene (e.g., 10-12 wt %) and optionally one or more carboxylic acids and 1,1,2, 2,3,3,4,4,4-nonafluoro-N-(2-hydroxyethyl)-N-1-methyl-1-butanesulfonamide before incorporation into the polyester.

In the polymer compositions of the invention, the fluoroalkyl derivative(s) described herein may be present in an amount of 0.01 to 99 weight % or 0.01 to 95 weight % or 0.01 to 90 weight % or 0.01 to 85 weight % or 0.01 to 80 weight % or 0.01 to 75 weight % or 0.01 to 70 weight % or 0.01 to 65 weight % or 0.01 to 60 weight % or 0.01 to 55 weight % or 0.01 to 50 weight % or 0.01 to 45 weight % or 0.01 to 40 weight % or 0.01 to 35 weight % or 0.01 to 30 weight % or 0.01 to 25 weight % or 0.01 to 20 weight % or 0.01 to 15 weight % or 0.01 to 10 weight % or 0.01 to 5 weight %, or 0.01 to 4 weight %, or 0.01 to 3 weight %, or 0.01 to 2 weight %, or 0.01 to 1 weight %, or 0.01 to 3 weight %, based on the total weight percentage of the polyester and the fluoroalkyl additive in the final polymer composition equaling 100 weight %.

In the polymer compositions of the invention, the fluoroalkyl derivative(s) described herein may be present in an amount of 0.01 to 99 weight % or 0.01 to 95 weight % or 0.5 to 90 weight % or 0.5 to 85 weight % or 0.5 to 80 weight % or 0.5 to 75 weight % or 0.5 to 70 weight % or 0.5 to 65 weight % or 0.5 to 60 weight % or 0.5 to 55 weight % or 0.5 to 50 weight % or 0.5 to 45 weight % or 0.5 to 40 weight % or 0.5 to 35 weight % or 0.5 to 30 weight % or 0.5 to 25 weight % or 0.5 to 20 weight % or 0.5 to 15 weight % or 0.5 to 10 weight % or 0.5 to 9 weight % or 0.5 to 8 weight %, or 0.5 to 7 weight %, or 0.5 to 6 weight % or 0.5 to 5 weight %, or 0.5 to 4 weight % or 0.5 to 3 weight % or 0.5 to 2 weight % or 0.5 to 1 weight %, based on the total weight percentage of the polyester and the fluoroalkyl additive in the final polymer composition equaling 100 weight %.

In the polymer compositions of the invention, the fluoroalkyl derivative(s) described herein may be present in an amount of 1 to 99 weight % or 1 to 95 weight % or 1 to 90 weight % or 1 to 85 weight % or 1 to 80 weight % or 1 to 75 weight % or 1 to 70 weight % or 1 to 65 weight % or 1 to 60 weight % or 1 to 55 weight % or 1 to 50 weight % or 1 to 45 weight % or 1 to 40 weight % or 1 to 35 weight % or 1 to 30 weight % or 1 to 25 weight % or 1 to 20 weight % or 1 to 15 weight % or 1 to 10 weight % or 1 to 9 weight % or 1 to 8 weight %, or 1 to 7 weight %, or 1 to 6 weight %, or 1 to 5 weight %, or 1 to 4 weight %, or 1 to 3 weight % or 1 to 2 weight %, or 1 to 1 weight %, based on the total weight percentage of the polyester and the fluoroalkyl additive in the final polymer composition equaling 100 weight %.

In the polymer compositions of the invention, the fluoroalkyl derivative(s) described herein may be present in an amount of 2 to 99 weight % or 2 to 95 weight % or 2 to 90 weight % or 2 to 85 weight % or 2 to 80 weight % or 2 to 75 weight % or 2 to 70 weight % or 2 to 65 weight % or 2 to 60 weight % or 2 to 55 weight % or 2 to 50 weight % or 2 to 45 weight % or 2 to 40 weight % or 2 to 35 weight % or 2 to 30 weight % or 2 to 25 weight % or 2 to 20 weight % or 2 to 15 weight % or 2 to 10 weight % or 2 to 9 weight % or 2 to 8 weight %, or 2 to 7 weight %, or 2 to 6 weight %, or 2 to 5 weight %, or 2 to 4 weight %, or 2 to 3 weight %, based on the total weight percentage of the polyester and the fluoroalkyl additive in the final polymer composition equaling 100 weight %.

In the polymer compositions of the invention, the fluoroalkyl derivative(s) described herein may be present in an amount of 5 to 99 weight % or 5 to 95 weight % or 5 to 90 weight % or 5 to 85 weight % or 5 to 80 weight % or 5 to 75 weight % or 5 to 70 weight % or 5 to 65 weight % or 5 to 60 weight % or 5 to 55 weight % or 5 to 50 weight % or 5 to 45 weight % or 5 to 40 weight % or 5 to 35 weight % or 5 to 30 weight % or 5 to 25 weight % or 5 to 20 weight % or 5 to 15 weight % or 5 to 10 weight %, In the polymer blend of the invention, the fluoroalkyl derivative(s) described herein may be present in an amount of 10 to 99 weight % or 10 to 95 weight % or 10 to 90 weight % or 10 to 85 weight % or 10 to 80 weight % or 10 to 75 weight % or 10 to 70 weight % or 10 to 65 weight % or 10 to 60 weight % or 10 to 55 weight % or 10 to 50 weight % or 10 to 45 weight % or 10 to 40 weight % or 10 to 35 weight % or 10 to 30 weight % or 10 to 25 weight % or 10 to 20 weight % or 10 to 15 weight %, based on the total weight percentage of the polyester and the fluoroalkyl additive in the final polymer composition equaling 100 weight %.

In the polymer compositions of the invention, the fluoroalkyl derivative(s) described herein may be present in an amount of 15 to 99 weight % or 15 to 95 weight % or 15 to 90 weight % or 15 to 85 weight % or 15 to 80 weight % or 15 to 75 weight % or 15 to 70 weight % or 15 to 65 weight % or 15 to 60 weight % or 15 to 55 weight % or 15 to 50 weight % or 15 to 45 weight % or 15 to 40 weight % or 15 to 35 weight % or 15 to 30 weight % or 15 to 25 weight %, based on the total weight percentage of the polyester and the fluoroalkyl additive in the final polymer composition equaling 100 weight %.

The invention further relates to the polyester compositions of the invention being blended with another polymer. The blend comprises:

(a) 5 to 99.99 weight % of at least one of the polyesters described herein; and (b) 0.01 to 95 weight % of at least one fluoroalkyl derivative;

(c) optionally, another polymer component which is not the at least one polyester described in (a).

The invention further relates to the a blend comprising:

(a) 5 to 99.98 weight % of at least one of the polyesters described herein; and (b) 0.01 to 95 weight % of at least one fluoroalkyl derivative; and (c) 0.01 to 95 weight % optionally, another polymer component which is not the at least one polyester described in (a), based on the total weight percentage of the polyester(s) useful in the invention, any other polymers, and the fluoroalkyl additive in the final polymer composition equaling 100 weight %.

Suitable examples of other polymeric components than can be present in the polyester compositions of the invention include, but are not limited to, nylon, polyesters different from those described herein, polyethylene, polypropylene, polyamides such as ZYTEL® from DuPont; polystyrene, polystyrene copolymers, styrene acrylonitrile copolymers, acrylonitrile butadiene styrene copolymers, poly(methylmethacrylate), acrylic copolymers, poly(ether-imides) such as ULTEM® (a poly(ether-imide) from General Electric); polyphenylene oxides such as poly(2,6-dimethylphenylene oxide) or poly(phenylene oxide)/polystyrene blends such as NORYL 1000® (a blend of poly(2,6-dimethylphenylene oxide) and polystyrene resins from General Electric); polyphenylene sulfides; polyphenylene sulfidesulfones; poly(ester-carbonates); polycarbonates such as LEXAN® (a polycarbonate from General Electric); polysulfones; polysulfone ethers; and poly(ether-ketones) of aromatic dihydroxy compounds; or mixtures of any of the other foregoing polymers. The blends can be prepared by conventional processing techniques known in the art, such as melt blending or solution blending. However, the polyester blends useful in the invention can either contain polycarbonate or not. In one embodiment, polycarbonate is not present in the polyester blends of the invention.

The polycarbonates useful in the polyester compositions of the invention also may be copolyestercarbonates such as those described in U.S. Pat. Nos. 3,169,121; 3,207,814; 4,194,038; 4,156,069; 4,430,484, 4,465,820, and 4,981,898, the disclosure regarding copolyestercarbonates from each of the U.S. patents is incorporated by reference herein.

Copolyestercarbonates useful in this invention can be available commercially and/or can be prepared by known methods in the art. For example, they can be typically obtained by the reaction of at least one dihydroxyaromatic compound with a mixture of phosgene and at least one dicarboxylic acid chloride, especially isophthaloyl chloride, terephthaloyl chloride, or both.

In addition, the polymer compositions in this invention may also contain from 0.01 to 25% by weight of the overall composition common additives such as colorants, dyes, mold release agents, flame retardants, plasticizers, nucleating agents, stabilizers, including but not limited to, UV stabilizers, thermal stabilizers and/or reaction products thereof, fillers, and impact modifiers.

In addition, the polymer compositions in this invention can also contain additives common in the applicable industry, for example, antimicrobial additives for the medical industry and/or health care industry and/or pharmaceutical industry.

The polymer compositions of the invention can include mold release agents that are commonly used in the art, including but not limited to, calcium stearate, stearic acid, and zinc stearate. While any amount of mold release agent can be used, in some embodiments, amounts of 0.10 to 5 weight % or 0.25 to 1 weight %, of the mold release agent can be used where the mold release agent and the polymer composition equal a total of 100 weight %.

Examples of typical commercially available impact modifiers well known in the art and useful in this invention include, but are not limited to, ethylene/propylene terpolymers; functionalized polyolefins, such as those containing methyl acrylate and/or glycidyl methacrylate; styrene-based block copolymeric impact modifiers, and various acrylic core/shell type impact modifiers. Residues of such additives are also contemplated as part of the polyester composition.

The polyester compositions of the invention can comprise at least one chain extender. Suitable chain extenders include, but are not limited to, multifunctional (including, but not limited to, bifunctional) isocyanates, multifunctional epoxides, including for example, epoxylated novolacs, and phenoxy resins. In certain embodiments, chain extenders may be added at the end of the polymerization process or after the polymerization process. If added after the polymerization process, chain extenders can be incorporated by compounding or by addition during conversion processes such as injection molding or extrusion. The amount of chain extender used can vary depending on the specific monomer composition used and the physical properties desired but is generally about 0.1 percent by weight to about 10 percent by weight, preferably about 0.1 to about 5 percent by weight, based on the total weigh of the polyester.

Thermal stabilizers are compounds that stabilize polyesters during polyester manufacture and/or post polymerization, including, but not limited to, phosphorous compounds, including, but not limited to, phosphoric acid, phosphorous acid, phosphonic acid, phosphinic acid, phosphonous acid, and various esters and salts thereof. The esters can be alkyl, branched alkyl, substituted alkyl, difunctional alkyl, alkyl ethers, aryl, and substituted aryl. In one embodiment, the number of ester groups present in the particular phosphorous compound can vary from zero up to the maximum allowable based on the number of hydroxyl groups present on the thermal stabilizer used. The term "thermal stabilizer" is intended to include the reaction product(s) thereof. The term "reaction product" as used in connection with the thermal stabilizers of the invention refers to any product of a polycondensation or esterification reaction between the thermal stabilizer and any of the monomers used in making the polyester as well as the product of a polycondensation or esterification reaction between the catalyst and any other type of additive. These can be present in the polyester compositions useful in the invention.

Reinforcing materials may be useful in the compositions of this invention. The reinforcing materials may include, but are not limited to, carbon filaments, silicates, mica, clay, talc, titanium dioxide, Wollastonite, glass flakes, glass beads and fibers, and polymeric fibers and combinations thereof. In one embodiment, the reinforcing materials are glass, such as, fibrous glass filaments, mixtures of glass and talc, glass and mica, and glass and polymeric fibers.

The following examples further illustrate how polyester compositions of the invention can be made and evaluated, and are intended to be purely exemplary of the invention and are not intended to limit the scope thereof.

EXAMPLES

Unless indicated otherwise, parts are parts by weight, temperature is in degrees Celsius (° C.) or is at room temperature, and pressure is at or near atmospheric pressure.

The inherent viscosity (IV) of the polyesters was determined in a 60/40 (wt/wt) phenol/tetrachloroethane solution at a concentration of 0.5 g/100 mL at 25° C.

As used herein, the abbreviation "wt" means "weight."

Unless stated otherwise, the glass transition temperature ($T_g$) was determined using a TA DSC 2920 instrument from Thermal Analyst Instruments at a scan rate of 20° C./min according to ASTM D3418.

The glycol content and the cis/trans ratio of the polyesters were determined by proton nuclear magnetic resonance (NMR) spectroscopy.

Unless otherwise specified, the cis/trans ratio of 1,4-cyclohexanedimethanol in the following polyesters was approximately 30/70, and could range from 35/65 to 25/75. Unless otherwise specified, the cis/trans ratio of 2,2,4,4-tetramethyl-1,3-cyclobutanediol in the following polyesters was approximately 50/50.

ASTM D638 procedure was used to determine the tensile properties. Tensile properties include tensile strength at yield, tensile strength at break (ultimate tensile strength), tensile modulus (Young's modulus), and elongation at yield and break. Tensile strength at yield is the maximum stress at which permanent, non-elastic deformation begins. Yield point is the point (load) at which the material yields, i.e., increase in strain occurs without an increase in stress. Ultimate tensile strength is the maximum stress a material can withstand before failing. Elongation at yield is the strain that the material undergoes at the yield point, or the percent change in length that occurs while the material is stressed to its yield point. Elongation at break is the strain at failure, or the percent change in length at failure. Tensile (or Young's) modulus, is the ratio of stress to strain within the elastic region of the stress-strain curve (prior to the yield point).

ASTM D790 procedure was used to determine the flexural properties.

ASTM D256 procedure was used to determine the Izod impact strength (notched) at 23° C.

ASTM D1003 procedure was used to determine the total transmittance and haze. The measurements were made on injection molded plaques having dimensions of 4"×4"×0.125".

L*, a*, and b* color coordinates were measured on transparent injection molded plaques having dimensions of 4"×4"×0.125" using a HunterLab UltraScan XE® spectrophotometer. The spectrophotometer was operated using a D65 illuminant light source with a 10° observation angle and integrating sphere geometry. The spectrophotometer was zeroed, standardized, UV calibrated, and verified in control. The color measurement was made in the total transition (TTRAN) mode. The L* value indicates the transmission/opacity of the sample. The a* value indicates the redness (+)/greenness (−) of the sample. The b* value indicates the yellowness (+)/blueness (−) of the sample.

Table 1 below lists the materials that were used in the following examples, their abbreviations, and main ingredient.

TABLE 1

| Material | Abbreviation | Main Ingredient |
|---|---|---|
| Fluoroalkyl Additive | A1 | Mixture of fluoroalkyl derivatives of the general formula: 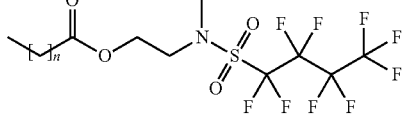 where n = 8 to 30. (Commercially available, e.g., from 3M under product name Repellent Polymer Melt Additive PM-870.) |
| Base Polymer | P1 | Copolyester comprising: 100 mole % TPA residues; 22 mole % TMCD residues; 78 mole % CHDM residues; and IV = 0.63 dL/g. |
| Base Polymer | P2 | Copolyester comprising: 35 mole % IPA residues; 65 mole % TPA residues; 100 mole % CHDM residues; and IV = 0.72 dL/g. |
| Base Polymer | P3 | Copolyester comprising: 100 mole % TPA residues; 69 mole % EG residules 31 mole % CHDM residues; and IV = 0.75 dL/g. |
| Base Polymer | P4 | Copolyester comprising: 100 mole % of TPA residues; 38 mole % EG residues; 62 mole % CHDM residues; and IV = 0.73 dL/g. |

As used herein, "TPA" refers to terephthalic acid, "TMCD" refers to 2,2,4,4-tetramethyl-1,3-cyclobutanediol, "CHDM" refers to 1,4-cyclohexanedimethanol, "IPA" refers to isophthalic acid, and "EG" refers to ethylene glycol.

Example 1

A1 was compounded with P1 in a twin-screw extruder to form a concentrate containing 8 wt % of A1 and pelletized after extrusion.

The 8 wt % concentrate was blended with additional P1 to form mixtures containing 0.5 wt %, 1 wt %, 2 wt %, 3 wt %, 4 wt %, and 5 wt % of A1 before injection molding.

The blends of P1 containing 0.5 to 5 wt % of A1 along with a control made of 100 wt % of P1 were injection molded into flexural bars with a Toyo 90 injection molding machine following the manufacturer's recommended processing conditions.

The flexural bars were subjected to a fibrinogen ELISA (enzyme-linked immunosorbent assay) to evaluate their fibrinogen binding behavior. The testing protocol is described below.

General Test Description

ELISA is an immunological assay used to detect the presence of a biomolecule, such as a protein, in a sample. In practice, proteins are physically adsorbed onto the flexural bar surface when the bars are inserted into a disposable microtiter plate. Then, in a separate microtiter plate, an antibody is applied over the same surface and allowed to bind to the protein. The degree of antibody binding is determined by the amount of the enzyme that is conjugated to the antibody. Detection of that enzyme amount is typically through the use of a chromogenic substrate for the enzyme. The extent of color change is proportional to the amount of adsorbed protein present and is typically measured spectrophotometrically using a plate reader.

Test Fixture

The fibrinogen ELISA experimental setup was designed and developed specifically for ELISA of flexural bars. The testing was used to evaluate the degree of protein adsorption of each substrate. A fixture was developed to allow consistent and convenient testing of polymer flexural bars with the dimensions of 5"×½"×⅛" (length×width×thickness in inches). The polymer bars were mounted in the fixture prior to testing. Unlike a typical ELISA where a series of reagents are successively added and removed from a microwell plate, this method allowed the simultaneous movement of 24 bars held in the fixture through a series of microwell plates that contained the various ELISA reagents.

The fixture 10 is shown in the FIGURE. The fixture 10 was made of two aluminum plates 12 and 14, which were connected at the corners with four metal rods 16. Each plate 12, 14 contained 24 holes corresponding to the well positions of a standard 24-well microtiter plate (not shown). The upper plate 12 held the polymer bars 19 in recesses 13 on the underside of the plate 12. When mounted, the bars protruded through the lower plate holes 18 and into the microplate wells (not shown). The lower plate 14 was constructed with a recessed well (not shown) that acts as a base resting on the testing microplate (not shown). A base plate 20 holds the testing microplate (now shown) and connects with the lower plate 14 via four short metal rods 21.

Fibrinogen ELISA Sample Preparation

Prior to ELISA, all sample bars were wiped with a lint-free tissue, moistened with sterile, deionized water, and re-dried with tissue. The cleaned test bars were then seated completely into the recesses of the test fixture and allowed to remain in place throughout the assay as the fixture was moved from one reagent to another in separate plates.

ELISA Procedure

The ELISA protocol was designed for the specific detection of fibrinogen adsorption to solid polymer substrates. The ELISA was initiated by incubating the polymer sample bars in an aqueous solution of fibrinogen (0.5 mg/mL in a 2% bovine serum albumin (w/v) phosphate-buffered saline solution prepared in a blocked tube) for five minutes at 37° C. The unbound fibrinogen was removed by three successive washes in phosphate-buffered saline (PBS). The sample bars were then incubated in a non-animal protein blocking agent (NAP) for 30 minutes at 37° C. to block unoccupied binding sites on the substrate. The sample bars were then incubated for one hour at 37° C. in the presence of an anti-fibrinogen, horseradish peroxidase antibody-conjugate (1 µg/mL) in a NAP blocked microtiter plate. After that, successive washes of the bars in a diluted TBST buffer were used to remove excess non-specific binding of the antibody-conjugate. In the final step of the ELISA procedure, the sample bars were incubated with the enzyme substrate (3,3',5,5'-tetramethylbenzidine). After 1 hour, the test fixture and the sample bars were removed from the microplate containing the enzyme substrate. Using a microplate spectrophotometer, absorbance measurements of the enzyme substrate wells were made at 630 nm to detect conversion of the enzyme substrate to the blue product. Fibrinogen binding values of various polymers were then inferred from the amount of enzyme substrate conversion and calculated relative to the polymer without additive after subtracting the background absorbance readings.

Each individual test included four replicate bars for each polymer sample. P1 without A1 was used as the universal control sample for all studies.

With regard to data interpretation, higher initial fibrinogen protein adsorption would indicate that the sample is more likely to induce higher level of platelet adhesion and platelet activation, which subsequently lead to thrombus and blood coagulation. Meanwhile, a polymer substrate with lower initial fibrinogen adsorption is expected to exhibit better hemocompatibility.

The fibrinogen ELISA data was analyzed using Dunnett's test to determine the statistical significance, when compared to the P1 control. (C. W. Dunnett, "A Multiple Comparison Procedure for Comparing Several Treatments with a Control," J. Am. Statistical Assoc., Vol. 50, p. 1096 (1955).)

In statistics, when performing a hypothesis test, a p-value helps to determine the significance of the results. Hypothesis tests are used to test the validity of a claim that is made about a population. The claim that is on trial is called the null hypothesis, and usually is a claim that there is no effect or difference in what is being tested. All hypothesis tests ultimately use a p-value to weigh the strength of the evidence (i.e., what the data are saying about the population). The p-value is a number between 0 and 1. A small p-value (typically ≤0.05) indicates strong evidence against the null hypothesis, so the null hypothesis can be rejected. A large p-value (>0.05) indicates weak evidence against the null hypothesis, so the null hypothesis cannot be rejected. A p-value very close to the cutoff (0.05) is considered to be marginal.

In data analysis, most authors refer to a p-value of <0.05 as being statistically significant, meaning the risk of incorrectly concluding there is a difference is less than 1 in 20 (or a 95% confidence in the conclusion). Thus, in this example, a p-value of <0.05 indicates a statistically significant difference between the treated sample and the control.

The results of the ELISA study are reported in Table 2.

TABLE 2

Percentage of Fibrinogen Adsorption Reduction

| | Weight Percentage of A1 in P1 | | | | | |
|---|---|---|---|---|---|---|
| | 0.5 | 1 | 2 | 3 | 4 | 5 |
| Test 1 | 26% (p: 0.0116) | 36% (p: 0.0018) | 11% (p: 0.3549) | 21% (p: 0.0608) | 30% (p: 0.0009) | 35% (p: 0.0003) |
| Test 2 | 30% (p: 0.0061) | 39% (p: 0.0013) | 24% (p: 0.03) | 31% (p: 0.008) | 45% (p: <0.0001) | 35% (p: 0.0002) |
| Test 3 | 12% (p: 0.3029) | 15% (p: 0.1735) | 32% (p: 0.002) | 24% (p: 0.0739) | 30% (p: 0.0278) | 38% (p: 0.0004) |
| Average | 23% | 30% | 22% | 25% | 35% | 36% |
| Standard Deviation | 9% | 13% | 11% | 5% | 9% | 2% |

As seen from Table 2, all of the A1 compounded samples showed positive fibrinogen adsorption reduction compared to the control P1 alone, and most results were statistically significant.

Example 2

The procedure of Example 1 was repeated except that P1 was replaced with P2, P3, and P4. A 5 wt % A1 concentrate was made with each polymer, which was then diluted with their respective base polymers to form samples with A1 at loading levels ranging from 0.5 to 5 wt %. The blends were then injection molded into flexural bars and subjected to fibrinogen ELISA. The control for each sample tested was the base polymer for that sample without A1.

The results of the ELISA study are reported in Table 3.

TABLE 3

Percentage of Fibrinogen Adsorption Reduction

| Sample | Fibrinogen Adsorption Reduction | P-Value |
|---|---|---|
| P2 + 0.5 wt % A1 | 15% ± 12% | 0.0885 |
| P2 + 1 wt % A1 | 26% ± 8% | 0.0043 |
| P2 + 1.5 wt % A1 | 38% ± 11% | 0.0002 |
| P2 + 2 wt % A1 | 32% ± 10% | 0.0071 |
| P2 + 5 wt % A1 | 31% ± 12% | 0.0078 |
| P3 + 1 wt % A1 | 15% ± 19% | 0.4076 |
| P3 + 2 wt % A1 | 23% ± 19% | 0.1726 |
| P4 + 0.5 wt % A1 | 6% ± 16% | 0.744 |
| P4 + 1 wt % A1 | 17% ± 4% | 0.0943 |
| P4 + 1.5 wt % A1 | 17% ± 6% | 0.1006 |

As seen from Table 3, all A1 compounded samples showed positive fibrinogen adsorption reduction compared to the control sample of P2, P3, or P4 alone. Samples of P2 with 1-5 wt % of A1 yielded statistically significant fibrinogen reduction relative to their control.

Example 3

The blends of P1 with various loadings of A1 prepared in Example 1 were formed into 1"×1"×0.125" (length×width×depth in inches) and 4"×4"×0.125" plaques. For each A1 loading level, the plaques were loaded into a Bruker™ tribometer and tested for their coefficient of friction (COF). The plaques were placed under a load of 3 N, and the 1"×1"×0.125" plaque was moved at a rate of 1.2 mm/sec across the surface of the 4"×4"×0.125" plaque. Each A1 loading level was run in triplicate with new plaques in each test.

The COF results are reported in Table 4.

TABLE 4

| Amount of A1 in P1 | Coefficient of Friction | Standard Deviation |
|---|---|---|
| 0 (control) | 0.694 | 0.273 |
| 0.5 wt % | 0.308 | 0.055 |
| 1 wt % | 0.242 | 0.036 |
| 2 wt % | 0.234 | 0.046 |
| 3 wt % | 0.216 | 0.087 |
| 4 wt % | 0.180 | 0.058 |
| 5 wt % | 0.166 | 0.057 |

As seen from Table 4, adding A1 lowered the COF of P1.

Example 4

An injection-molded sample of P1 containing 2 wt % of A1 was Gamma sterilized (50 kGy) and then submitted for three tests under the ISO 10993 series of standards for biocompatibility evaluation: (1) cytotoxicity test; (2) intracutaneous injection test; and (3) Kligman maximization test. The injection-molded sample passed all three tests.

Example 5

The IV and Tg of P1 alone and of P1 with A1 at several compounding levels were measured. The results are reported in Table 5.

TABLE 5

| Amount of A1 in P1 | IV (dL/g) | $T_g$ (° C.) |
|---|---|---|
| 0 wt % | $0.607^a$ | $103.4^a$ |
| 0.5 wt % | — | $102.9^a$ |
| 1 wt % | $0.596^a$ | $100.7^a$ |
| 2 wt % | $0.591^a$ | $96.3^a$ |
| 3 wt % | — | $94.3^a$ |
| 4 wt % | — | $89.5^a$ |
| 5 wt % | $0.574^a$ | $83.3^a$ |
| 8 wt % | $0.553^a/0.565^b$ | $77.7^a$ |

$^a$flexural bar (dimensions - 5 in. × 0.5 in. × 0.125 in.)
$^b$pellet

As seen from Table 5, at low loading levels of A1, the IVs of the injected molded samples were very similar. Moreover, the IV of the pellet at 8 wt % of A1 was very similar to that of the injection molded flexural bar at the same loading level. Furthermore, the Tg of the samples decreased as the concentration of A1 increased.

Example 6

The tensile properties of P1, P2, P3, and P4 alone and of these polymers with A1 at several compounding levels were determined. The results are reported in Table 6.

TABLE 6

| Sample | Tensile Properties | | | | |
|---|---|---|---|---|---|
| | Break Strength (MPa) | Elongation @ Break (%) | Yield Strength (MPa) | Elongation @ Yield (%) | Modulus (MPa) |
| P1 (control) | 52 | 210 | 43.2 | 7 | 1575 |
| P1 + 0.5 wt % A1 | 50.1 ± 1.4 | 155.4 ± 13.7 | 44.6 ± 0.05 | 5.3 ± 0.03 | 1564 ± 3.9 |
| P1 + 1 wt % A1 | 48 ± 1.3 | 143.9 ± 8.96 | 45.6 ± 0.05 | 5 ± 0.02 | 1620 ± 5.8 |
| P1 + 2 wt % A1 | 50.4 ± 0.5 | 161.3 ± 16.2 | 46.6 ± 0.09 | 4.9 ± 0.01 | 1625 ± 12.3 |
| P1 + 3 wt % A1 | 48.8 ± 1.5 | 147.8 ± 14.3 | 48.1 ± 0.03 | 4.6 ± 0.01 | 1670 ± 7.5 |
| P1 + 4 wt % A1 | 45 ± 5.4 | 126.5 ± 27.1 | 49.5 ± 0.02 | 4.5 ± 0.02 | 1702 ± 6.2 |
| P1 + 5 wt % A1 | 45.4 ± 6.0 | 129.7 ± 30.5 | 50.4 ± 0.06 | 4.4 ± 0.02 | 1725 ± 11.4 |
| P1 + 8 wt % A1 | 34.4 ± 3.1 | 84.2 ± 40.8 | 52.8 ± 0.22 | 4.4 ± 0.02 | 1770 ± 8.7 |
| P2 (control) | 51.0 | 300.0 | 47.0 | 5.0 | 1815 |
| P2 + 0.5 wt % A1 | 32.1 ± 1.4 | 239.4 ± 8.2 | 49.5 ± 0.07 | 4 ± 0.01 | 1807 ± 3 |
| P2 + 1 wt % A1 | 31.9 ± 1.6 | 242.4 ± 10.9 | 50.1 ± 0.06 | 4 ± 0.02 | 1804 ± 4 |
| P2 + 1.5 wt % A1 | 31.4 ± 1.8 | 234.2 ± 13.3 | 50.7 ± 0.1 | 4.1 ± 0.01 | 1792 ± 5 |
| P2 + 2 wt % A1 | 30.6 ± 0.9 | 239.6 ± 12.8 | 51.3 ± 0.11 | 4.1 ± 0.01 | 1779 ± 7 |
| P2 + 5 wt % A1 | 30.6 ± 1.5 | 171.3 ± 10 | 54 ± 0.07 | 4.4 ± 0.01 | 1714 ± 3 |
| P3 (control) | 28.0 | 110.0 | 50.0 | 4.3 | 1873 |
| P3 + 1 wt % A1 | 25.1 ± 0.7 | 219.8 ± 13 | 50.3 ± 0.05 | 3.9 ± 0.02 | 1922 ± 5 |
| P3 + 2 wt % A1 | 30.9 ± 4.9 | 299.3 ± 67.3 | 51.3 ± 0.08 | 4 ± 0.02 | 1932 ± 16 |
| P4 (control) | 52.0 | 330.0 | 45.0 | 5.0 | 1800 |
| P4 + 0.5 wt % A1 | 34 ± 2.6 | 235.1 ± 20.1 | 49.4 ± 0.14 | 4 ± 0.00 | 1859 ± 29 |
| P4 + 1 wt % A1 | 32.4 ± 1.7 | 231.7 ± 8.2 | 49.9 ± 0.08 | 4 ± 0.01 | 1791 ± 13 |
| P4 + 1.5 wt % A1 | 31.6 ± 0.3 | 234.9 ± 3.0 | 50.1 ± 0.08 | 4 ± 0.01 | 1796 ± 6 |

Example 7

The Izod impact strength of P1, P2, P3, and P4 alone and of these polymers with A1 at several compounding levels were determined. The results are reported in Table 7.

TABLE 7

| Sample | Izod Impact Strength (J/m) | No Break Percentage |
|---|---|---|
| P1 (control) | 860 | 100 |
| P1 + 0.5 wt % A1 | 889.9 | 100 |
| P1 + 1 wt % A1 | 930.3 | 100 |
| P1 + 2 wt % A1 | 964.2 | 100 |
| P1 + 3 wt % A1 | 1006.9 | 100 |
| P1 + 4 wt % A1 | 1029.4 | 100 |
| P1 + 5 wt % A1 | 95.3 | 0 |
| P1 + 8 wt % A1 | 72.0 | 0 |
| P2 (control) | 80.0 | 0 |
| P2 + 0.5 wt % A1 | 84.4 | 0 |
| P2 + 1 wt % A1 | 66.3 | 0 |
| P2 + 1.5 wt % A1 | 65.4 | 0 |
| P2 + 2 wt % A1 | 59.4 | 0 |
| P2 + 5 wt % A1 | 31.0 | 0 |
| P3 (control) | 101.0 | 50 |
| P3 + 1 wt % A1 | 77.2 | 0 |
| P3 + 2 wt % A1 | 55.3 | 0 |
| P4 (control) | no break | 100 |
| P4 + 0.5 wt % A1 | 76.2 | 0 |
| P4 + 1 wt % A1 | 78.1 | 0 |
| P4 + 1.5 wt % A1 | 67.9 | 0 |

As seen from Table 7, there was minimal change in the Izod impact strength of polymer P1 compounded with A1 at concentrations up to 4 wt %. The Izod impact strength of polymers P2, P3 and P4 compounded with A1 decreased as the concentration of A1 increased.

Example 8

The flexural strength of P1 alone and of P1 with A1 at several compounding levels were determined. The results are reported in Table 8.

TABLE 8

| Amount of A1 in P1 | Flexural Properties | | |
|---|---|---|---|
| | Elongation @ Break (%) | Break Strength (MPa) | Modulus (MPa) |
| 0.5 wt % | 7.004 | 72.706 | 1703.5 |
| 1 wt % | 7.006 | 74.201 | 1751.5 |
| 2 wt % | 7.005 | 75.129 | 1823.9 |
| 5 wt % | 7.003 | 77.437 | 1919.2 |
| 8 wt % | 7.004 | 74.727 | 1951.9 |

Example 9

The haze, transmittance, and color values of P1 alone and of P1 with A1 at several compounding levels were determined. The results are reported in Table 9.

TABLE 9

| Amount of A1 in P1 | L* | a* | b* | Haze (%) | Transmittance (%) |
|---|---|---|---|---|---|
| 0 wt % | 95.54 | −0.16 | 0.63 | 0.51 | 90.9 |
| 0.5 wt % | 95.71 | −0.26 | 0.82 | 0.45 | 91.7 |
| 1 wt % | 95.69 | −0.34 | 1.1 | 0.51 | 91.7 |
| 2 wt % | 95.51 | −0.44 | 1.86 | 0.56 | 91.2 |
| 3 wt % | 94.96 | −0.75 | 3.67 | 9.12 | 90 |
| 4 wt % | 94.7 | −0.92 | 4.81 | 6.29 | 89.3 |
| 5 wt % | 94.76 | −0.7 | 3.9 | 3.89 | 90 |
| 8 wt % | 81.66 | 0.38 | 16.09 | 41 | 64.4 |

As seen from Table 9, the samples maintained low haze, b* values, and transmittance up to about 2 wt % loading of A1.

The invention has been described in detail with reference to the embodiments disclosed herein, but it will be understood that variations and modifications can be effected within the spirit and scope of the invention.

What is claimed is:

1. A polymer composition comprising:
   (I) at least one polyester which comprises:
      (a) a dicarboxylic acid component comprising:
         i) 50 to 100 mole % of terephthalic acid residues;
         ii) 0 to 50 mole % of aromatic dicarboxylic acid residues having up to 20 carbon atoms; and
         iii) 0 to 10 mole % of aliphatic dicarboxylic acid residues having up to 16 carbon atoms; and
      (b) a glycol component comprising 1,4-cyclohexanedimethanol residues,
   wherein the total mole % of the dicarboxylic acid component is 100 mole %, the total mole % of the glycol component is 100 mole %; and
   wherein the inherent viscosity of the polyester is from 0.1 to 1.2 dL/g as determined in 60/40 (wt/wt) phenol/tetrachloroethane at a concentration of 0.5 g/100 ml at 25° C.; and
   (II) at least one fluoroalkyl derivative having the general formula:

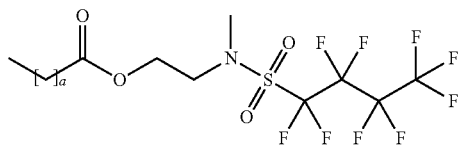

wherein n=an integer from 8 to 30.

2. The polymer composition of claim 1 comprising ethylene glycol residues.

3. The polymer composition of claim 2 wherein the glycol component comprises 20 to 40 mole % 1,4-cyclohexanedimethanol residues and 60 to 80 mole % ethylene glycol residues.

4. The polymer composition of claim 2 wherein the glycol component comprises 50 to 80 mole % 1,4-cyclohexanedimethanol residues and 20 to 50 mole % ethylene glycol residues.

5. The polymer composition of claim 1 or 2 wherein the glycol component comprises diethylene glycol.

6. The polymer composition of claim 1 wherein the acid component comprising isophthalic acid residues.

7. The polymer composition of claim 6 wherein the acid component comprises 25 to 45 mole % residues of isophthalic acid or an ester thereof.

8. The polymer composition of claim 1 or 2 wherein the acid component comprises 70 to 100 mole % residues of terephthalic acid or an ester thereof.

9. The polymer composition of claim 1 or 2 wherein said fluoroalkyl derivative is mixed with polyethylene.

10. The polymer composition of claim 1 or 2 wherein said fluoroalkyl derivative is present in the amount of 0.01 to 8 weight % based on the total weight percentage of said polyester and said fluroalkyl derivative.

11. The polymer composition of claim 1 or 2 wherein said fluoroalkyl derivative is present in the amount of 0.01 to 5 weight % based on the total weight percentage of said polyester and said fluroalkyl derivative.

12. The polymer composition of claim 1 or 2 which adsorbs at least 5% less fibrinogen compared to the polyester alone according to a fibrinogen ELISA protocol comprising the following steps: (1) incubating the polymer sample in flexural bar form in a phosphate-buffered saline solution containing 0.5 mg/mL of fibrinogen and 2% of bovine serum albumin (w/v) for 5 minutes; (2) removing unbound fibrinogen from the sample bar by washing the bar with phosphate-buffered saline having a pH of 7.3 three times; (3) incubating the sample bar in a non-animal protein blocking agent for 30 minutes at 37° C.; (4) incubating the bar in a 1 µg/mL solution of an anti-fibrinogen horseradish peroxidase antibody-conjugate in a non-animal protein-blocked microtiter plate for 60 minutes at 37° C.; (5) washing the bar four times with a diluted TBST buffer to remove excess non-specific binding of the antibody-conjugate; (6) incubating the bar with an enzyme substrate 3,3',5,5'-tetramethylbenzidine for 60 minutes; (7) removing the bar from the microplate containing the enzyme substrate; and (8) measuring the absorbance of the enzyme substrate in the microplate well using a microplate spectrophotometer at 630 nanometers to detect conversion of the enzyme substrate to the blue product.

13. The polymer composition of claim 2 which adsorbs from 15% to 45% less fibrinogen compared to the polyester alone.

14. The polymer composition of claim 6 which adsorbs from 5% to 20% less fibrinogen compared to the polyester alone.

15. The polymer compositions of claim 1 or 2 which have a coefficient of friction of less than 0.50 as measured with a Bruker™ tribometer using a 1"×1"×0.125" plaque on a 4"×4"×0.125" plaque under a 3 N normal load at 1.2 mm/second.

16. The polymer compositions of claim 1 or 2 which have a coefficient of friction (COF) of 0.10 to 0.50 as measured with a Bruker™ tribometer using a 1"×1"×0.125" plaque on a 4"×4"×0.125" plaque under a 3 N normal load at 1.2 mm/second.

17. An article of manufacture made with the polymer composition of claim 1 or 2.

18. The article of claim 17 which is selected from a medical article, pharmaceutical article, veterinarian article, bioprocessing article, or a food article.

19. The article of claim 17 which is a medical device.

20. The article of claim 19 which is an intravenous component.

* * * * *